(12) United States Patent
Salafsky

(10) Patent No.: US 10,768,174 B2
(45) Date of Patent: Sep. 8, 2020

(54) ATTACHMENT OF PROTEINS TO INTERFACES FOR USE IN NONLINEAR OPTICAL DETECTION

(71) Applicant: Bluelight Therapeutics, Inc., South San Francisco, CA (US)

(72) Inventor: Joshua Salafsky, San Francisco, CA (US)

(73) Assignee: BLUELIGHT THERAPEUTICS, INC., South San Francisco, CA (US)

(*) Notice: Subject to any disclaimer, the term of this patent is extended or adjusted under 35 U.S.C. 154(b) by 86 days.

(21) Appl. No.: 15/631,649

(22) Filed: Jun. 23, 2017

(65) Prior Publication Data

US 2017/0350883 A1    Dec. 7, 2017

Related U.S. Application Data

(63) Continuation of application No. PCT/US2015/067285, filed on Dec. 22, 2015.
(Continued)

(51) Int. Cl.
*G01N 21/63* (2006.01)
*G01N 33/543* (2006.01)
*G01N 33/487* (2006.01)

(52) U.S. Cl.
CPC ..... *G01N 33/54353* (2013.01); *G01N 33/487* (2013.01); *G01N 21/63* (2013.01)

(58) Field of Classification Search
CPC ..... G01N 33/543; G01N 33/487; G01N 21/63
See application file for complete search history.

(56) References Cited

U.S. PATENT DOCUMENTS 3,253,065 A    5/1966    Hansen
3,847,909 A    11/1974   Schickfluss et al.
(Continued)

FOREIGN PATENT DOCUMENTS

CA    2604099 C    2/2011
CN    1864066 A    11/2006
(Continued)

OTHER PUBLICATIONS

Nguyen et al. ("Connparsion of the Energetic of Avidin, Streptavidin, NeutrAvidin, and Anti-Bio Antibody Binding to Biotinylated Lipid Bilayer Examined by Second-Harmonic Generation". Anal. Chem., vol. 84, 201-208, published Nov. 28, 2011.) (Year: 2011).*
(Continued)

*Primary Examiner* — Tracy Vivlemore
*Assistant Examiner* — Nam P Nguyen
(74) *Attorney, Agent, or Firm* — Wilson Sonsini Goodrich & Rosati

(57) ABSTRACT

Methods are disclosed for tethering a biological entity to a substrate comprising: (a) forming a supported lipid bilayer on a surface of a substrate, wherein the supported lipid bilayer comprises an anchor molecule conjugated to a first affinity tag that is present in the lipid bilayer at a concentration greater than or equal to 5 mole percent; and (b) contacting the supported lipid bilayer with a biological entity, wherein the biological entity comprises an nonlinear-active label and a second affinity tag capable of binding to the first affinity tag, thereby tethering the biological entity to the supported lipid bilayer in an oriented fashion.

16 Claims, 15 Drawing Sheets

Related U.S. Application Data

(60) Provisional application No. 62/096,334, filed on Dec. 23, 2014.

(56) References Cited

U.S. PATENT DOCUMENTS

| | | |
|---|---|---|
| 4,619,879 A | 10/1986 | Kakuta et al. |
| 4,708,871 A | 11/1987 | Geysen |
| 4,739,044 A | 4/1988 | Stabinsky |
| 4,757,141 A | 7/1988 | Fung et al. |
| 4,775,637 A | 10/1988 | Sutherland et al. |
| 4,818,710 A | 4/1989 | Sutherland et al. |
| 4,833,092 A | 5/1989 | Geysen |
| 4,844,613 A | 7/1989 | Batchelder et al. |
| 4,978,503 A | 12/1990 | Shanks et al. |
| 4,997,928 A | 3/1991 | Hobbs, Jr. |
| 5,001,209 A | 3/1991 | Wreesmann et al. |
| 5,143,854 A | 9/1992 | Pirrung et al. |
| 5,145,790 A | 9/1992 | Mattingly et al. |
| 5,156,810 A | 10/1992 | Ribi |
| 5,215,899 A | 6/1993 | Dattagupta |
| 5,223,409 A | 6/1993 | Ladner et al. |
| 5,231,191 A | 7/1993 | Woo et al. |
| 5,236,826 A | 8/1993 | Marshall |
| 5,244,813 A | 9/1993 | Walt et al. |
| 5,250,264 A | 10/1993 | Walt et al. |
| 5,252,494 A | 10/1993 | Walt |
| 5,298,741 A | 3/1994 | Walt et al. |
| 5,320,814 A | 6/1994 | Walt et al. |
| 5,324,591 A | 6/1994 | Georger, Jr. et al. |
| 5,324,633 A | 6/1994 | Fodor et al. |
| 5,376,556 A | 12/1994 | Tarcha et al. |
| 5,389,482 A | 2/1995 | Okano et al. |
| 5,403,484 A | 4/1995 | Ladner et al. |
| 5,427,908 A | 6/1995 | Dower et al. |
| 5,432,018 A | 7/1995 | Dower et al. |
| 5,432,610 A | 7/1995 | King et al. |
| 5,485,277 A | 1/1996 | Foster |
| 5,498,530 A | 3/1996 | Schatz et al. |
| 5,498,538 A | 3/1996 | Kay et al. |
| 5,512,490 A | 4/1996 | Walt et al. |
| 5,521,289 A | 5/1996 | Hainfeld et al. |
| 5,556,762 A | 9/1996 | Pinilla et al. |
| 5,571,689 A | 11/1996 | Heuckeroth et al. |
| 5,580,717 A | 12/1996 | Dower et al. |
| 5,599,627 A | 2/1997 | Aoki et al. |
| 5,624,821 A | 4/1997 | Winter et al. |
| 5,627,024 A | 5/1997 | Maruyama et al. |
| 5,631,734 A | 5/1997 | Stern et al. |
| 5,633,724 A | 5/1997 | King et al. |
| 5,648,260 A | 7/1997 | Winter et al. |
| 5,652,060 A | 7/1997 | Uchida et al. |
| 5,663,143 A | 9/1997 | Ley et al. |
| 5,696,157 A | 12/1997 | Wang et al. |
| 5,698,426 A | 12/1997 | Huse |
| 5,723,286 A | 3/1998 | Dower et al. |
| 5,723,323 A | 3/1998 | Kauffman et al. |
| 5,734,018 A | 3/1998 | Rutter et al. |
| 5,738,825 A | 4/1998 | Rudigier et al. |
| 5,750,373 A | 5/1998 | Garrard et al. |
| 5,763,192 A | 6/1998 | Kauffman et al. |
| 5,766,905 A | 6/1998 | Studier et al. |
| 5,770,434 A | 6/1998 | Huse |
| 5,800,992 A | 9/1998 | Fodor et al. |
| 5,814,524 A | 9/1998 | Walt et al. |
| 5,821,060 A | 10/1998 | Arlinghaus et al. |
| 5,834,758 A | 11/1998 | Trulson et al. |
| 5,847,400 A | 12/1998 | Kain et al. |
| 5,962,248 A | 10/1999 | Tadano et al. |
| 6,023,540 A | 2/2000 | Walt et al. |
| 6,025,601 A | 2/2000 | Trulson et al. |
| 6,030,787 A | 2/2000 | Livak et al. |
| 6,040,586 A | 3/2000 | Slettnes |
| 6,055,051 A | 4/2000 | Eisenthal |
| 6,084,991 A | 7/2000 | Sampas |
| 6,095,555 A | 8/2000 | Becker et al. |
| 6,096,497 A | 8/2000 | Bauer |
| 6,110,426 A | 8/2000 | Shalon et al. |
| 6,121,983 A | 9/2000 | Fork et al. |
| 6,124,102 A | 9/2000 | Fodor et al. |
| 6,134,002 A | 10/2000 | Stimson et al. |
| 6,180,415 B1 | 1/2001 | Schultz et al. |
| 6,187,247 B1 | 2/2001 | Buzzell et al. |
| 6,194,222 B1 | 2/2001 | Buechler et al. |
| 6,204,067 B1 | 3/2001 | Simon et al. |
| 6,228,326 B1 | 5/2001 | Boxer et al. |
| 6,284,197 B1 | 9/2001 | Abbott et al. |
| 6,361,956 B1 | 3/2002 | Hanninen et al. |
| 6,410,245 B1 | 6/2002 | Northrop et al. |
| 6,455,303 B1 | 9/2002 | Orwar et al. |
| 6,456,423 B1 | 9/2002 | Nayfeh et al. |
| 6,576,478 B1 | 6/2003 | Wagner et al. |
| 6,680,377 B1 | 1/2004 | Stanton et al. |
| 6,682,942 B1 | 1/2004 | Wagner et al. |
| 6,699,719 B2 | 3/2004 | Yamazaki |
| 6,753,200 B2 | 6/2004 | Craighead et al. |
| 6,775,003 B2 | 8/2004 | Ivarsson |
| 6,780,584 B1 | 8/2004 | Edman et al. |
| 6,882,420 B2 | 4/2005 | Rassman et al. |
| 6,917,726 B2 | 7/2005 | Levene et al. |
| 6,953,694 B2 | 10/2005 | Salafsky et al. |
| 7,002,686 B2 | 2/2006 | Lieberman et al. |
| 7,013,054 B2 | 3/2006 | Levene et al. |
| 7,023,547 B2 | 4/2006 | Venkatasubbarao et al. |
| 7,033,764 B2 | 4/2006 | Korlach et al. |
| 7,045,337 B2 | 5/2006 | Schultz et al. |
| 7,052,847 B2 | 5/2006 | Korlach et al. |
| 7,056,661 B2 | 6/2006 | Korlach et al. |
| 7,056,676 B2 | 6/2006 | Korlach et al. |
| 7,105,310 B1 | 9/2006 | Gray et al. |
| 7,108,970 B2 | 9/2006 | Levinson |
| 7,126,688 B2 | 10/2006 | Rassman et al. |
| 7,181,122 B1 | 2/2007 | Levene et al. |
| 7,193,711 B2 | 3/2007 | Rassman et al. |
| 7,233,391 B2 | 6/2007 | Schermer et al. |
| 7,262,866 B2 | 8/2007 | Ivarsson |
| 7,282,514 B1 | 10/2007 | Belfield et al. |
| 7,292,742 B2 | 11/2007 | Levene et al. |
| 7,316,769 B2 | 1/2008 | Craighead et al. |
| 7,336,359 B1 | 2/2008 | Simpson et al. |
| 7,336,389 B2 | 2/2008 | Silverbrook et al. |
| 7,361,466 B2 | 4/2008 | Korlach et al. |
| 7,384,773 B1 | 6/2008 | Benson et al. |
| 7,406,222 B2 | 7/2008 | Kornilovich |
| 7,416,844 B2 | 8/2008 | Korlach et al. |
| 7,470,549 B2 | 12/2008 | Yamamoto et al. |
| 7,473,361 B2 | 1/2009 | Craighead et al. |
| 7,485,424 B2 | 2/2009 | Korlach et al. |
| 7,518,764 B2 | 4/2009 | Osborne et al. |
| 7,545,494 B2 | 6/2009 | Haiml et al. |
| 7,545,501 B2 | 6/2009 | Muraishi et al. |
| 7,563,624 B2 | 7/2009 | Ezoe et al. |
| 7,605,179 B2 | 10/2009 | Wischik et al. |
| 7,709,808 B2 | 5/2010 | Reel et al. |
| 7,833,398 B2 | 11/2010 | Craighead et al. |
| 7,943,305 B2 | 5/2011 | Korlach et al. |
| 7,943,307 B2 | 5/2011 | Korlach et al. |
| 8,039,270 B2 | 10/2011 | Dultz et al. |
| 8,062,900 B2 | 11/2011 | Modavis |
| 8,139,288 B2 | 3/2012 | Osborne et al. |
| 8,355,133 B2 | 1/2013 | Dultz et al. |
| 8,497,073 B2 | 7/2013 | Salafsky |
| 8,497,703 B2 | 7/2013 | Kim et al. |
| 8,932,822 B1 | 1/2015 | Salafsky |
| 9,182,406 B2 | 11/2015 | Salafsky |
| 9,383,361 B2 | 7/2016 | Salafsky |
| 9,395,358 B2 | 7/2016 | Salafsky |
| 9,428,789 B2 | 8/2016 | Salafsky et al. |
| 9,880,172 B2 | 1/2018 | Salafsky |
| 9,938,560 B2 | 4/2018 | Salafsky et al. |
| 9,989,534 B2 | 6/2018 | Salafsky et al. |
| 2002/0030894 A1 | 3/2002 | Volcker et al. |
| 2002/0037529 A1 | 3/2002 | Fesik et al. |
| 2002/0094520 A1 | 7/2002 | Salafsky et al. |
| 2002/0094528 A1 | 7/2002 | Salafsky |

(56) References Cited

U.S. PATENT DOCUMENTS

| | | |
|---|---|---|
| 2002/0127563 A1 | 9/2002 | Salafsky |
| 2003/0087239 A1 | 5/2003 | Stanton et al. |
| 2003/0129649 A1 | 7/2003 | Kobilka et al. |
| 2003/0148391 A1 | 8/2003 | Salafsky |
| 2003/0175160 A1 | 9/2003 | Archibald et al. |
| 2003/0205681 A1 | 11/2003 | Modlin |
| 2003/0224390 A1 | 12/2003 | Fowlkes et al. |
| 2004/0091955 A1 | 5/2004 | Forster et al. |
| 2004/0146460 A1 | 7/2004 | Salafsky |
| 2005/0107472 A1 | 5/2005 | Wischik et al. |
| 2005/0118731 A1 | 6/2005 | Salafsky |
| 2005/0148063 A1 | 7/2005 | Cracauer et al. |
| 2005/0259249 A1 | 11/2005 | Dombeck et al. |
| 2006/0046134 A1 | 3/2006 | Cho et al. |
| 2006/0228725 A1 | 10/2006 | Salafsky |
| 2007/0172947 A1 | 7/2007 | Shirwan |
| 2007/0178012 A1 | 8/2007 | Ferrante et al. |
| 2008/0038281 A1* | 2/2008 | Altin .................. A61K 9/1271 424/178.1 |
| 2009/0010894 A1 | 1/2009 | Langston |
| 2009/0032592 A1 | 2/2009 | Christensen |
| 2009/0035217 A1 | 2/2009 | Chilcote et al. |
| 2010/0068144 A1 | 3/2010 | Salafsky |
| 2010/0120164 A1 | 5/2010 | Salafsky |
| 2010/0323105 A1 | 12/2010 | Hosoe |
| 2011/0014612 A1 | 1/2011 | Hendricks et al. |
| 2012/0202296 A1 | 8/2012 | Eisenthal |
| 2012/0214164 A1 | 8/2012 | Densham |
| 2013/0108549 A1 | 5/2013 | Orser et al. |
| 2013/0129628 A1 | 5/2013 | Pantazis et al. |
| 2013/0288271 A1 | 10/2013 | Salafsky |
| 2014/0113312 A1 | 4/2014 | Salafsky et al. |
| 2014/0178896 A1 | 6/2014 | Salafsky |
| 2014/0178897 A1 | 6/2014 | Salafsky |
| 2014/0186854 A1 | 7/2014 | Salafsky |
| 2014/0187431 A1 | 7/2014 | Salafsky |
| 2014/0187432 A1 | 7/2014 | Salafsky |
| 2014/0187433 A1 | 7/2014 | Salafsky |
| 2015/0330990 A1 | 11/2015 | Salafsky et al. |
| 2015/0377900 A1 | 12/2015 | Salafsky et al. |
| 2016/0292354 A1 | 10/2016 | Salafsky |
| 2016/0356767 A1 | 12/2016 | Salafsky |
| 2016/0356768 A1 | 12/2016 | Salafsky |
| 2018/0217150 A1 | 8/2018 | Salafsky |
| 2018/0340940 A1 | 11/2018 | Salafsky et al. |
| 2019/0137510 A1 | 5/2019 | Salafsky et al. |

FOREIGN PATENT DOCUMENTS

| | | |
|---|---|---|
| CN | 1997892 A | 7/2007 |
| EP | 0740156 A1 | 10/1996 |
| EP | 0740156 B1 | 9/2001 |
| EP | 0873520 B1 | 10/2002 |
| EP | 0941474 B1 | 3/2006 |
| EP | 1702206 A1 | 9/2006 |
| EP | 1798555 A1 | 6/2007 |
| GB | 2520111 A | 5/2015 |
| JP | H11119270 A | 4/1999 |
| JP | 2000505798 A | 5/2000 |
| JP | 2004521323 A | 7/2004 |
| JP | 2004530105 A | 9/2004 |
| JP | 2008515385 A | 5/2008 |
| JP | 2012126722 A | 7/2012 |
| WO | WO-8403506 A1 | 9/1984 |
| WO | WO-8403564 A1 | 9/1984 |
| WO | WO-9005317 A1 | 5/1990 |
| WO | WO-9429351 A2 | 12/1994 |
| WO | WO-9534683 A1 | 12/1995 |
| WO | WO-9709446 A1 | 3/1997 |
| WO | WO-9715390 A1 | 5/1997 |
| WO | WO-9728189 A1 | 8/1997 |
| WO | WO-9735196 A1 | 9/1997 |
| WO | WO-9746251 A1 | 12/1997 |
| WO | WO-9747314 A1 | 12/1997 |
| WO | WO-9814277 A1 | 4/1998 |
| WO | WO-9815833 A1 | 4/1998 |
| WO | WO-9820036 A1 | 5/1998 |
| WO | WO-9820159 A1 | 5/1998 |
| WO | WO-9820169 A1 | 5/1998 |
| WO | WO-9851435 A1 | 11/1998 |
| WO | WO-9951642 A1 | 10/1999 |
| WO | WO-0000823 A1 | 1/2000 |
| WO | WO-0039585 A1 | 7/2000 |
| WO | WO-0244412 A1 | 6/2002 |
| WO | WO-0246764 A1 | 6/2002 |
| WO | WO-02054071 A1 | 7/2002 |
| WO | WO-02061415 A1 | 8/2002 |
| WO | WO-02095070 A2 | 11/2002 |
| WO | WO-03055379 A2 | 7/2003 |
| WO | WO-03064991 A2 | 8/2003 |
| WO | WO-03104851 A2 | 12/2003 |
| WO | WO-2004048929 A2 | 6/2004 |
| WO | WO-2008156560 A1 | 12/2008 |
| WO | WO-2010031185 A1 | 3/2010 |
| WO | WO-2010151609 A1 | 12/2010 |
| WO | WO-2011131747 A1 | 10/2011 |
| WO | WO-2011140030 A2 | 11/2011 |
| WO | WO-2012129347 A1 | 9/2012 |
| WO | WO-2013115867 A1 | 8/2013 |
| WO | WO2013115867 A1 * | 8/2013 |
| WO | WO-2013162654 A1 | 10/2013 |
| WO | WO-2014201435 A1 | 12/2014 |
| WO | WO-2016/003936 | 1/2016 |
| WO | WO-2016106286 A1 | 6/2016 |
| WO | WO-2016161386 A1 | 10/2016 |
| WO | WO-2017196891 A1 | 11/2017 |
| WO | WO-2018204135 A2 | 11/2018 |

OTHER PUBLICATIONS

Sly et al. (Anal. Chem. 2014, vol. 86, pp. 11045-11054, published Oct. 14, 2014) (Year: 2014).*

Cass et al. (Protein Expression and Purification 40 (2005) pp. 77-85, published Nov. 24, 2004) (Year: 2004).*

Cell Signaling Technology (<https://www.cellsignal.com/products/primary-antibodies/ras-antibody/3965>, print retrieved on Feb. 8, 2020) (Year: 2020).*

Abbyad, et al., Measurement of solvation responses at multiple sites in a globular protein. J Phys Chem B. Jul. 19, 2007;111(28):8269-76. Epub Jun. 26, 2007.

Abel, et al., Fiber-optic evanescent wave biosensor for the detection of oligonucleotides.. Anal., Chem. 1996; 68:2905-2912.

Abrams, et al., Mutant ras epitopes as targets for cancer vaccines. Semin Oncol. Feb. 1996; 23(1):118-34.

Achari, et al., 1.67-A X-ray structure of the B2 immunoglobulin-binding domain of streptococcal protein G and comparison to the NMR structure of the B1 domain. Biochemistry. Nov. 3, 1992;31(43)10449-57.

Aggarwal, et al., Contribution of the S4 segment to gating charge in the Shaker K+ channel. Neuron. Jun. 1996;16(6):1169-77.

Agrawal, et al., Site-specific functionalization of oligodeoxynucleotides for non-radioactive labelling. Tetrahedron Letters. 1990 31:1543-1546.

Antony, et al., A molecular beacon strategy for the thermodynamic characterization of triplex DNA: triplex formation at the promoter region of cyclin D1. Biochemistry. Aug. 7, 2001;40(31):9387-95.

Aplin, et al., Protein-derivatised glass coverslips for the study of cell-to substratum adhesion. Anal Biochem. May 1, 1981;113(1):144-8.

Arnold, et al., Identification of bone morphogenetic proteins and their receptors in human breast cancer cell lines: importance of BMP2. Cytokine. Dec. 1999;11(12):1031-7.

Arnold, Metal-affinity separations: a new dimension in protein processing. Biotechnology (NY). Feb. 1991; 9(2):151-156.

Arora, et al., Multiple Intermediates, Diverse Conformations, and Cooperative Conformational Changes Underlie the Catalytic Hydride Transfer Reaction of Dihydrofolate Reductase, Top Curr Chem., 2013, 337:165-87.

(56) References Cited

OTHER PUBLICATIONS

Sawaya, et al., Loop and Subdomain Movements in the Mechanism of *Escherichia coli* Dihydrofolate Reductase: Crystallographic Evidence, Biochemistry 1997, 36:586-603.
Bakhtiar, Peptide nucleic acids: deoxyribonucleic acid mimics with a peptide backbone. Biochem. Educ. 1998; 26:277-280.
Bar-Sagi, A Ras by any other name. Mol Cell Biol. Mar. 2001;21(5):1441-3.
Ben-Oren, et al., Infrared nonlinear optical measurements of membrane potential in photoreceptor cells. Biophys J. Sep. 1996; 71(3):1616-20.
Bentin, et al., Triplexes involving PNA. Triple Helix Form. Oligonucleotides. 1999; 245-255.
Berkovic, et al., Interference between second-harmonic generation from a substrate and from an adsorbate layer. Journal of the Optical Society of America B-Optical Physics. 1989; 6:205-208.
Bethea, Experimental technique of dc induced SHG in liquids: measurement of the nonlinearity of CH2I2. Applied Optics. 1975; 14:1447-1451.
Bier, et al., Real-time measurement of nucleic-acid hybridization using evanescent-wave sensors: steps towards the genosensor. Sens. Actuators B Chem. 1997; 38:78-82.
Bieri, et al., Micropatterned immobilization of a G protein-coupled receptor and direct detection of G protein activation. Nature Biotechnology. 1999; 17:1105-1108.
Blanchard, et al., High-density oglionucleotide arrays. Biosensors and Bioelectronics. 1996; 11:687-690.
Block, et al., Immobilized-metal affinity chromatography (IMAC): a review, Methods Enzymol, 2009, 463:439-73.
Bonnet, et al., Kinetics of conformational fluctuations in DNA hairpin-loops. Proc Natl Acad Sci U S A. Jul. 21, 1998; 95(15):8602-6.
Bonnet, et al., Thermodynamic basis of the enhanced specificity of structured DNA probes. Proc Natl Acad Sci U S A. May 25, 1999; 96(11):6171-6.
Bouevitch, et al., Probing membrane potential with nonlinear optics. Biophys J. Aug. 1993;65(2):672-9.
Boyd, et al., Local-field enhancement on rough surfaces with the use of optical 2nd-harmonic generation. Phys. Rev. B 1984; 30:519-526.
Brian, et al., Allogeneic Stimulation of Cyto-toxic T-cells by Supported Planar Membranes. PNAS-Biological Sciences. 1984; 81(19): 6159-6163.
Brown, et al., Exploring the new world of the genome with DNA microarrays. Nature Genet. 1999; 21 (Suppl.):33-37.
Brown, et al., Molecular beacons attached to glass beads fluoresce upon hybridisation to target DNA. Chemical Comm. 2000; 621-622.
Buchardt, et al., Peptide nucleic acids and their potential applications in biotechnology. Tibtech. 1993; 11:384-386.
Bucher, et al., Induced fit or conformational selection? The role of the semi-closed state in the maltose binding protein, Biochemistry 2011, 50(48):10530-9.
Campagnola, et al., High-resolution nonlinear optical imaging of live cells by second harmonic generation. Biophys J. Dec. 1999;77(6):3341-9.
Campagnola, et al., Three-dimensional high-resolution second-harmonic generation imaging of endogenous structural proteins in biological tissues. Biophysical Journal., 2002; 81:493-508.
Case-Green, et al., Analysing genetic information with DNA arrays. Curr Opin Chem Biol. Jun. 1998;2(3):404-10.
Cha, et al., Atomic Scale Movement of the Voltage-Sensing Region in a Potassium Channel Measureed via Spectroscopy. Nature. Dec. 16, 1999;402(6763):809-13.
Cha, et al., Characterizing voltage-dependent conformational changes in the Shaker K+ channel with fluorescence. Neuron. Nov. 1997;19(5):1127-40.
Chang, et al., Human genome contains four genes homologous to transforming genes of Harvey and Kirsten murine sarcoma viruses. Proc Natl Acad Sci U S A. Aug. 1982;79(16):4848-52.
Chen, et al., Detection of Molecular Monolayers by Optical Second-Harmonic Generation. Physical Review Letters. 1981; 46:1010-1012.
Chen, et al., Molecular beacons: a real-time polymerase chain reaction assay for detecting Salmonella. Anal Biochem. Apr. 10, 2000; 280(1):166-72.
Cheung, et al., Making and reading microarrays. Nature Genetics. 1999; 21:15-19.
Chin, et al., Calmodulin: a prototypical calcium sensor, Trends Cell Biol., 2000, 10(8):322-8.
Schnell, et al., Structure, dynamics and catalytic function of dihydrofolate reductase, Annu. Rev. Biophys. Biomol Struct, 2004, 33:119-40.
Chrisey, et al., Covalent Attachment of Synthetic DNA to Self-Assembled Monolayer Films. Nucleic Acids Research. 1996; 24:3031-3039.
Christopoulos. Allosteric binding sites on cell-surface receptors: novel targets for drug discovery. Nat Rev Drug Discov. Mar. 2002;1(3):198-210.
Chung, et al., Two-Dimensional Standing Wave Total Internal Reflection Fluorescence Microscopy: Superresolution Imaging of Single Molecular and Biological Specimens. Biophys J. Sep. 1, 2007; 93(5): 1747-1757.
Schweitzer, et al., Dihydrofolate reductase as a therapeutic target, FASEB J 1990, 4(8):2441-52.
Clackson, et al., Making antibody fragments using phage display libraries. Nature. Aug. 15, 1991; 352(6336):624-8.
Clark, et al., Second harmonic generation properties of fluorescent polymer-encapsulated gold nanoparticles. J. Am. Chem. Soc. 2000; 122:10234-10235.
Clarke, et al., Conformational changes of fibrinogen after adsorption. Journal of Physical Chemistry B. 2005; 109:22027-22035.
Clays, et al., Nonlinear optical properties of proteins measured by hyper-rayleigh scattering in solution. Science. Nov. 26, 1993;262(5138):1419-22.
Clayton, et al., K-ras point mutation detection in lung cancer: comparison of two approaches to somatic mutation detection using ARMS allele-specific amplification. Clin Chem. Dec. 2000; 46(12):1929-38.
Cohen, et al., A Fluorescent Probe Designed for Studying Protein Conformational Change. PNAS. 2005; 102(4):965-970.
Cohen, et al., Probing protein electrostatics with a synthetic fluorescent amino acid. Science. 2002; 296:1700-1703.
Conboy, et al., Studies of Alkane/water interfaces by total internal reflection second harmonic generation. J. Phys. Chem. 1994; 98:9688-9698.
Conway, et al., Fibrils formed in vitro from alpha-synuclein and two mutant forms linked to Parkinson's disease are typical amyloid. Biochemistry. Mar. 14, 2000;39(10):2552-63.
Corey. Peptide nucleic acids: expanding the scope of nucleic acid recognition. TIBTECH. 1997; 15:224-229.
Craighead, et al., Textured surfaces: optical storage and other applications. J. Vac. Sci. Technol. 1982; 20:316-319.
Craighead, et al., Textured thin-film Si solar selective adsorbers using reactive ion etching. Appl. Phys. Lett. 1980; 37:653-655.
Cwirla, et al., Peptides on phage: a vast library of peptides for identifying ligands. Proc Natl Acad Sci U S A. Aug. 1990; 87(16):6378-82.
De Baar, et al., One-tube real-time isothermal amplification assay to identify and distinguish human immunodeficiency virus type 1 subtypes A, B, and C and circulating recombinant forms AE and AG. Journal of Clinical Microbiology. 2001; 39(5):1895-1902.
De Baar, et al., Single rapid real-time monitored isothermal RNA amplification assay for quantification of human immunodeficiency virus type 1 isolates from groups M, N, and O. J Clin Microbiol. Apr. 2001; 39(4):1378-84.
De Ronde, et al., Establishment of new transmissible and drug-sensitive human immunodeficiency virus type 1 wild types due to transmission of nucleoside analogue-resistant virus. J Virol. Jan. 2001;75(2):595-602.
Delprincipe et al., Two Photo and UV-Laser Flash Photlysis of CA Cage Dimethoynitrophenyl-EGTA-4. Cell Calcium. 1999; 25:85-91.

(56) References Cited

OTHER PUBLICATIONS

Derrick, et al., Crystal structure of a streptococcal protein G domain bound to an Fab fragment. Nature. Oct. 22, 1999;359(6397):752-4.
Devor. Use of molecular beacons to verify that the serine hydroxymethyltransferase pseudogene SHMT-ps1 is unique to the order Primates. Genome Biol. 2001;2(2):RESEARCH0006. Epub Jan. 29, 2001.
Ditcham, et al., An immunosensor with potential for the detection of viral antigens in body fluids, based on surface second harmonic generation. Biosens Bioelectron. May 2001;16(3):221-4.
Ditlbacher, et al., Electromagnetic Interaction of Fluorophores with Designed Two-Dimensional Silver Nanoparticle Arrays. Applied Physics B .2001; 73;373-377.
Doring, et al., Enhanced internal dynamics of a membrane transport protein during substrate translocation. Protein Sci. Nov. 2000;9(11):2246-50.
Dracheva, et al., N-methyl-D-aspartic acid receptor expression in the dorsolateral prefrontal cortex of elderly patients with schizophrenia. Am J Psychiatry. Sep. 2001;158(9):1400-10.
Duan, et al., Crystal structures of the maltodextrin-maltose-binding protein complexed with reduced oligosaccharides: flexibility of tertiary structure and ligand binding, J. Mol. Biol. 2001, 306(5):1115-26.
Dubertret, et al., Single-mismatch detection using gold-quenched fluorescent oligonucleotides. Nat Biotechnol. Apr. 2001;19(4):365-70.
Dueholm, et al., Chemistry, properties, and applications of PNA (Peptide Nucleic Acid). New J. Chem.1997; 21:19-31.
Duggan, et al., Expression profiling using cDNA microarrays. Nat Genet. Jan. 1999;21(1 Suppl):10-4.
Duncan, et al., The binding site for C1q on IgG. Nature. Apr. 21, 1988; 332(6166):738-40.
Durand, et al., Use of molecular beacons to detect an antifolate resistance-associated mutation in Plasmodium falciparum. Antimicrob Agents Chemother. Dec. 2000; 44(12):3461-4.
Dustin, et al., Receptor signaling clusters in the immune synapse, Annu Rev Biophys., 2012, 41: 543-56.
Dworczak, et al., Electric field induced second harmonic generation (EFISH) experiments in the swivel cell: new aspects of an established method. Phys. Chem. Chem. Phys., 2000; 2:5057-5064.
Dwyer, et al., Periplasmic binding proteins: a versatile superfamily for protein engineering. Curr. Opin. Struct. Biol. 2004, 14(4):495-504.
Echo Qualified 1536—Well COC Source Microplate, Low Dead Volume, web page, 1 page.
Eckstein. Oligonucleotides and analogues. Oxford University Press. 1991.
Efimov, et al., Bacteriophage T4 as a surface display vector. Virus Genes. 1995;10(2):173-7.
Eisenthal, Photochemistry and photophysics of liquid interfaces by second harmonic spectroscopy. J. Phys. Chem. 1996; 100:12997-13006.
Ekins, et al., Microarrays: their origins and applications. Trends Biotechnol. Jun. 1999;17(6):217-8.
Eldrup, et al., Peptide nucleic acids: potential as antisense and antigene drugs. Adv. Amino Acid Mimetics Peptidomimetics. 1999; 2:221-245.
Elender, et al., Functionalisation of Si/SiO2 and glass surfaces with ultrathin dextran films and deposition of lipid bilayers. Biosens Bioelectron. 1996;11(6-7):565-77.
El-Hajj, et al., Detection of rifampin resistance in *Mycobacterium tuberculosis* in a single tube with molecular beacons. J Clin Microbiol. Nov. 2001;39(11):4131-7.
Emory, et al., Direct Observation of Size-Dependent Optical Enhancement in Single Metal Nanoparticles. J. Am. Chem. Soc. 1998; 120: 8009-8010.
Emory, et al., Screening and Enrichment of Metal Nanoparticles with Novel Optical Properties. J. Phys. Chem. B. 1998; 102:493-497.
England. Unnatural amino acid mutagenesis: A precise tool for probing protein structure and function. Biochemistry. 2004; 43(37):11623-11629.
Seo, et al., Protein conformational dynamics dictate the binding affinity for a ligand, Nat. Commun, 2014, 5:3724.
Eun, et al., Molecular beacons: a new approach to plant virus detection. Phytopathology. Mar. 2000; 90(3):269-75. doi: 10.1094/PHYTO.2000.90.3.269.
European search report dated Jan. 24, 2008 for EP Application No. 03736879.2.
European search report dated May 18, 2005 for EP Application No. 01995403.1.
European search report dated Dec. 3, 2004 for EP Application No. 01957166.0.
Evenas, et al., Ligand-induced structural changes to maltodextrin-binding protein as studied by solution, NMR spectroscopy, J. Mol. Biol. 2001, 309(4):961-74.
Falkiewicz. Peptide nucleic acids and their structural modifications. Acta Biochim Pol. 1999; 46(3):509-29.
Fang, et al., Using molecular beacons to probe molecular interactions between lactate dehydrogenase and single-stranded DNA. Anal Chem. Jul. 15, 2000;72(14):3280-5.
Fejer, et al., Quasi-Phase-Matched Second Harmonic Generation Tuning and Tolerances. IEEE Journal of Quantum Electronics. 1992; 28(11):2631-2654.
Felderhof, et al., Optical second-harmonic generation from adsorbate layers in total-reflection geometry. Journal of the Optical Society of America B-Optical Physics. 1993; 10:1824-1833.
Feller, et al., Investigation of surface-induced alignment liquid-crystal molecules by optical second-harmonic generation. Physical Review A. 1991; 43(12), 6778-6792.
Ferguson, et al., A fiber-optic DNA biosensor microarray for the analysis of gene expression. Nat Biotechnol. Dec. 1996;14(13):1681-4.
Fierke, et al., Construction and evaluation of the kinetic scheme associated with dihydrofolate, reductase from *Escherichia coli*, Biochemistry, 1987, 26(13):4085-92.
Finn, et al., Measurements of hyperpolarizabilities for some halogenated methanes. J. Chem. Phys. 1974; 60:454-458.
Fittinghoff, Collinear type II second-harmonic-generation frequency-resolved optical gating for use with high-numerical-aperature objectives, 1998, Opt Lett, 23(13), 1046-1048.
Fodor, et al., Light-directed Spatially-addressable Parallel Chemical Synthesis. Science. 1991; 251:767-773.
Fodor, Massively parallel genomics. Science. 1997; 277:393-395.
Fortin, et al., Use of real-time polymerase chain reaction and molecular beacons for the detection of *Escherichia coli* O157:H7. Anal Biochem. Feb. 15, 2001;289(2):281-8.
Frey, et al., Two-dimensional protein crystallization via metal-ion coordination by naturally occurring surface histidines. Proc Natl Acad Sci U S A. May 14, 1996;93(10):4937-41.
Fulton, et al., Advanced multiplexed analysis with the FlowMetrix system. Clin Chem. Sep. 1997; 43(9):1749-56.
Galletto, et al., Enhancement of second harmonic response by adsorbates on gold colloids: the effect of aggregation. J. Phys. Chem. B. 1999; 103:8706-8710.
Gao, et al., Messenger RNA release from ribosomes during 5'-translational blockage by consecutive low-usage arginine but not leucine codons in *Escherichia coli*. Mol Microbiol. Aug. 1997; 25(4):707-16.
Garcia-Pomar, et al., Experimental two-dimensional field mapping of total internal reflection lateral beam shift in a self-collimated photonic crystal, Appl. Phys. Lett. 94, 061121 (2009) http://dx.doi.org/10.1063/1.3085768.
Georger, et al., Coplanar Patterns of Self-assembled Monolayers for Selective Cell-adhesion and Outgrowth Thin Solid Films. 1992; 210(1-2): 716-719.
Gerry, et al., Universal DNA microarray method for multiplex detection of low abundance point mutations. J Mol Biol. Sep. 1999,17; 292(2):251-62.
Gether, et al., Fluorescent labeling of purified beta 2 adrenergic receptor. Evidence for ligand-specific conformational changes. Biol Chem. Nov. 24, 1995;270(47):28268-75.

(56) References Cited

OTHER PUBLICATIONS

Geysen, et al., Small peptides induce antibodies with a sequence and structural requirement for binding antigen comparable to antibodies raised against the native protein. Proc Natl Acad Sci U S A. Jan. 1985;82(1):178-82.
Geysen, et al., Strategies for epitope analysis using peptide synthesis. J Immunol Methods. Sep. 24, 1987;102(2):259-74.
Geysen, et al., The delineation of peptides able to mimic assembled epitopes. Ciba Found Symp. 1986;119:130-49.
Geysen, et al., Use of peptide synthesis to probe viral antigens for epitopes to a resolution of a single amino acid. Proc Natl Acad Sci U S A. Jul. 1984; 81(13):3998-4002.
Ghanouni, et al., Agonist-induced conformational changes in the G-protein-coupling domain of the beta 2 adrenergic receptor. Proc Natl Acad Sci U S A. May 22, 2001;98(11):5997-6002. Epub May 15, 2001.
Ghanouni, et al., Functionally Different Agonists Induce Distinct Conformations in the G Protein Coupling Domain of the B2 Adrenergic Receptor. Journal of Biological Chemistry. 2001; 276:24433-24436.
Giesendorf, et al., Molecular beacons: a new approach for semiautomated mutation analysis. Clin Chem. Mar. 1998;44(3):482-6.
Giusti, et al., Synthesis and characterization of 5'-fluorescent-dye-labeled oligonucleotides. PCR Methods Appl. Feb. 1993;2(3):223-7.
Glauner, et al., Spectroscopic Mapping of Voltage Sensor Movement in the Shaker Potassium Channel. Nature. 1999; 402:813-817.
Gliko, et al., Fast two-dimensional standing-wave total-internal-reflection fluorescence microscopy using acousto-optic deflectors. Optics Letters. 2009; 34(6):836-838.
Goddard, et al., Sequence dependent rigidity of single stranded DNA. Phys Rev Lett. Sep. 11, 2000; 85(11):2400-3.
Goh, et al., Absolute Orientation of Water-Molecules at the Neat Water-Surface. Journal of Physical Chemistry. 1988; 92:5074-5075.
Goh, et al., Conformational changes associated with protein-protein interactions, Curr. Opin. Struct. Biol. 2004, 14(1):104-9.
Gold, et al., The *Mycobacterium tuberculosis* IdeR is a dual functional regulator that controls transcription of genes involved in iron acquisition, iron storage and survival in macrophages. Mol Microbiol. Nov. 2001; 42(3):851-65.
Gonzalez, et al., Race-specific HIV-1 disease-modifying effects associated with CCR5 haplotypes. Proc Natl Acad Sci U S A. Oct. 12, 1999; 96(21):12004-9.
Goodey, et al., Allosteric regulation and catalysis emerge via a common route. Nat Chem Biol. Aug. 2008; 4(8):474-82. doi: 10.1038/nchembio.98.
Grabarek, Structure of a trapped intermediate of calmodulin: calcium regulation of EF-hand proteins from a new perspective, J Mol. Biol. 2005; 346(5):1351-66.
Greijer, et al., Multiplex real-time NASBA for monitoring expression dynamics of human cytomegalovirus encoded IE1 and pp67 RNA. J Clin Virol. Feb. 2002;24(1-2):57-66.
Gronenborn, et al., A novel, highly stable fold of the immunoglobulin binding domain of streptococcal protein G. Science. Aug. 9, 1991; 253(5020):657-61.
Groves, et al., Electrical manipulation of glycan-phosphatidyl inositol-tethered proteins in planar supported bilayers. Biophys J. Nov. 1996; 71(5):2716-23.
Groves, et al., Micropattern formation in supported lipid membranes. Acc Chem Res. Mar. 2002; 35(3):149-57.
Groves, et al.,Micropatterning fluid bilayers on solid supports. Science. 1997; 275:651-653.
Gunner, et al., Electrostatic Potentials in Rhodopseudomonas Viridis Reaction Centers: Implications for the Driving Force and Directionality of Electron Transfer. J. Phys. Chem. 1996; 100:4277-4291.
Gupta, et al., A general method for the synthesis of 3'-sulfhydryl and phosphate group containing oligonucleotides. Nucleic Acids Res. Jun. 11, 1991;19(11):3019-25.

Hall, et al., Syntheses and Photophysical Properties of Some 5(2)-Aryl-2(5)-(4-pyridy0oxazoles and Related Oxadiazoles and Furans. J. Heterocyclic Chem. 1992; 29,:1245-1273.
Hall, et al., The structural basis for the transition from Ras-GTP to Ras-GDP. Proc Natl Acad Sci U S A. Sep. 17, 2002; 99(19):12138-42. Epub Sep. 4, 2002.
Hammes-Schiffer, et al., Relating protein motion to catalysis, Annu. Rev. Biochem. 2006, 75:519-41.
Harrick, Internal reflection spectroscopy. Harrick Scientific Corporation. 2nd printing 1979.
Heath, et al., Covalent attachment of immunoglobulins to liposomes via glycosphingolipids. Biochim Biophys Acta. Jan. 8, 1981; 640(1):66-81.
Heil, et al., Betaine-homocysteine methyltransferase (BHMT): genomic sequencing and relevance to hyperhomocysteinemia and vascular disease in humans. Mol Genet Metab. Nov. 2000; 71(3):511-9.
Heinz, Determination of molecular orientation of monlayer adsorbates by optical second-harmonic generation. Physical Review A. 1991; 28(3):1883-1885.
Heinz, et al., Spectroscopy of Molecular Monolayers by Resonant Second-Harmonic Generation. Phys. Rev. Lett. 1982; 48, 478. DOI: http://dx.doi.org/10.1103/PhysRevLett.48.478.
Helmreich, et al., Structure and function of proteins in G-protein-coupled signal transfer. Biochim Biophys Acta. Oct. 29, 1996;1286(3):285-322.
Helps, et al., Use of real-time quantitative PCR to detect Chlamydophila felis infection. J Clin Microbiol. Jul. 2001; 39(7):2675-6.
Hicks, Studies of Chemical Processes in Liquids Using Short Laser Pulses: 1. The Dynamics of Photoisomerization of Polar Molecules in Solution 2. Studies of Liquid Surfaces by Second Harmonic Generation Ph.D. dissertation, Columbia University. 1986.
Hoffmann, et al., Low scale multiple array synthesis and DNA hybridization of peptide nucleic acids. Pept. Proc. Am. Pept. Symp. 15th. 1999; 233-234.
Huang, et al., Nonlinear optical properties of potential sensitive styryl dyes. Biophys J. May 1988; 53(5):665-70.
Hubbard, Autoregulatory mechanisms in protein-tyrosine kinases. Journal of Biological Chemistry. 1988; 273(20):11987-11990.
Hubbard, et al., Nonlinear optical studies of a fluorinated poled polyimide guest-host system. Applied Physics Letters. 1994; 65(3):265-267.
Huse, et al., The conformational plasticity of protein kinases. Cell. 2002; 109:275-282.
Hyrup, et al., Peptide Nucleic Acids (PNA): Synthesis, Properties and Potential Applications. Bioorg. Med. 1996; 4:5-23.
International Preliminary Report on Patentability dated Jun. 27, 2017 for PCT Application US 2015067285; International search report and written opinion dated Mar. 3, 2016 for PCT Application US 2015067285.
International search report and written opinion dated Oct. 6, 2015 for PCT Application No. US-201538375.
International search report dated Jan. 22, 2002 for PCT/US2001/022411.
International search report dated Feb. 10, 2006 for PCT Application No. PCT/US2003/017807.
International search report dated Mar. 23, 2006 for PCT/US2002/022681.
International search report dated Apr. 20, 2012 for PCT/US2012/030010.
International search report dated May 1, 2002 for PCT/US2001/046932.
International search report dated Oct. 20, 2001 for PCT/US2001/022412.
International search report dated Dec. 27, 2001 for PCT/US2001/022441.
Ishima, et al., Protein dynamics from NMR. Nature Structural Biology. 2000; 7:740-3.
Jager, et al., Comparison of quasi-phase-matching geometries for second harmonic generation in poled polymer channel waveguides at 1.5 mm,. Appl. Phys. Lett.1996; 68:1183-85.
Jiang, et al., Display of a PorA peptide from Neisseria meningitidis on the bacteriophage T4 capsid surface. Infect Immun. Nov. 1997; 65(11):4770-7.

(56) References Cited

OTHER PUBLICATIONS

Jordens, et al., Amplification with molecular beacon primers and reverse line blotting for the detection and typing of human papillomaviruses. J Virol Methods. Sep. 2000;89(1-2):29-37.
Joshi, et al., Metal-containing DNA hairpins as hybridization probes. Chem. Commun., 2001, 549-550.
Kaboev, et al., PCR hot start using primers with the structure of molecular beacons (hairpin-like structure). Nucleic Acids Res. Nov. 1, 2000;28(21):E94.
Kajikawa, et al., Second harmonic generation in disperse-red-labeled poly(methyl methacrylate) Langmuir Blodgett film. Appl. Phys. Letters. May 3, 1993; 62(18):2161-2163.
Kalb et al., Formation of Supported Planar Lipid Bilayers by Fusion of Vesicles to Supported Phospholipid Monolayers, Biochimica Biophysica Acta, 1992, 1103:307-16.
Kamat, et al., Picosecond Dynamics of Silver Nanoclusters. Photoejection of Electrons and Fragmentation. J. Phys. Chem. B. 1998; 102:3123-3128.
Kang, et al., Linkage of recognition and replication functions by assembling combinatorial antibody Fab libraries along phage surfaces. Proc Natl Acad Sci U S A. May 15, 1991;88(10):4363-6.
Kemnitz, et al., The Phase of 2nd-Harmonic Light Generated at an Interface and Its Relation to Absolute Molecular-Orientation. Chemical Physics Letters. 1986; 131:285-290.
Khatchatouriants, et al., GFP is a selective non-linear optical sensor of electrophysiological processes in Caenorhabditis elegans. Biophys J. Nov. 2000;79(5):2345-52.
Kleinfield, et al., Controlled outgrowth of dissociated neurons on patterned substrates. J Neurosci. Nov. 1988;8(11):4098-120.
Kleinjung, et al., Fibre-optic genosensor for specific determination of femtomolar DNA oligomers. Analytica Chimica Acta. 1997; 350:51-58.
Klerks, et al., Development of a multiplex AmpliDet RNA for the simultaneous detection of Potato leafroll virus and Potato virus Y in potato tubers. J Virol Methods. Apr. 2001;93(1-2):115-25.
Knighton, et al., Crystal structure of the catalytic subunit of cyclic adenosine monophosphate-dependent protein kinase. Science. Jul. 26, 1991;253(5018):407-14.
Knudsen, et al., Application of Peptide Nucleic Acid in Cancer Therapy. Anti-Cancer Drug. 1997; 8:113-118.
Kondo, et al., Free-energy landscapes of protein domain movements upon ligand binding. J Phys. Chem. B 2011, 115(23):7629-36.
Kostrikis, et al., Spectral genotyping of human alleles. Science. Feb. 20, 1998; 279(5354):1228-9.
Kota, et al., Detection of transgenes in crop plants using molecular beacon assays, Plant Mol Biology Rep. 1999; 17:363-370.
Kozarac, et al., Interaction of Proteins with Lipid Monolayers at the Air-Solution Interface Studied by Reflection Spectroscopy. Eur. Biophys. J. 1987; 15:193-196.
Kriech, et al., Using the intrinsic chirality of a molecule as a label-free probe to detect molecular adsorption to a surface by second harmonic generation. Applied Spectroscopy. 2005; 59:46-753.
Kuhner, et al., Lipid mono- and bilayer supported on polymer films: composite polymer-lipid films on solid substrates. Biophys J. Jul. 1994;67(1):217-26.
Kull, et al., Force generation by kinesin and myosin cytoskeletal motor proteins, J Cell Sci. 2013, 126: 9-19.
Kursula, Crystallographic snapshots of initial steps in the collapse of the calmodulin central helix, Acta Cryst, (2014), D70, 24-30.
Lamprecht, et al., Femtosecond decay-time measurement of electron-plasma oscillation in nanolithographically designed silver particles. Appl. Phys. B. 1997; 64:269-272.
Lanciotti, et al., Nucleic acid sequence-based amplification assays for rapid detection of West Nile and St. Louis encephalitis viruses. J Clin Microbiol. Dec. 2001;39(12):4506-13.
Landry, et al., Pulse simulations of a mirrored counterpropagating-QPM device. Optics Express. 1999; 5(8):176-187.
Lang, et al., Parkinson's disease. Second of two parts. N Engl J Med. Oct. 15, 1998; 339(16):1130-43.
Larsson, et al., Transmembrane movement of the shaker K+ channel S4. Neuron. Feb. 1996;16(2):387-97.
Lazurkin, Stability and specificity of triplexes formed by peptide nucleic acid with DNA. Molecular Biology. 1999; 33(1):79-83.
Leone, et al., Molecular beacon probes combined with amplification by NASBA enable homogeneous, real-time detection of RNA. Nucleic Acids Res. May 1, 1998;26(9):2150-5.
Levicky, et al., Using Self-Assembly to Control the Structure of DNA Monolayers on Gold: A Neutron Reflectivity Study. Journal of the American Chemical Society. 1998; 120:9787-9792.
Levine, Conjugated electron contributions to the second order hyperpolarizability of substituted benzene molecules J. Chem. Phys. 1975; 63:115-117.
Levine, et al., Absolute signs of hyperpolarizabilities in the liquid state. J. Chem. Phys. 1974; 60(10)3856-3858.
Levine, et al., Charge transfer complexes and hyperpolarizabilities. J. Chem. Phys. 1977; 66:1070-1074.
Levine, et al., Molecular hyperpolarizabilities determined from conjugated and nonconjugated organic liquids. Appl. Phys. Lett. 1974; 24:445-447.
Levine, et al., Second and third order hyperpolarizabilities of organic molecules. J. Chem. Phys. 1975; 63(6):2666-2682.
Levine, et al., Second Order Hyperpolarizability of a Polypeptide a-helix: Poly--y-benzyl-L-glutamate. J. Chem. Phys. 1976; 65(5):1989-1993.
Levine, et al., Ultraviolet dispersion of the donor-acceptor charge transfer contribution to the second order hyperpolarizability. J. Chem. Phys. 1978; 69(12): 5240-5245.
Lewin, et al., Use of real-time PCR and molecular beacons to detect virus replication in human immunodeficiency virus type 1-infected individuals on prolonged effective antiretroviral therapy. Virol. Jul. 1999; 73(7):6099-103.
Lewis, et al., Second Harmonic Generation of Biological Interfaces: Probing the Membrane Protein Bacteriorhodopsin and Imaging Membrane Potential Around GFP Molecules at Specific Sites in Neuronal Cells of C. elegans. Chemical Physics. 1999; 245:133-144.
Li, et al., Filamentous bacteriophage display of a bifunctional protein A::scFv fusion. Mol Biotechnol. Jun. 1998; 9(3):187-93.
Li, et al., Molecular beacon-based homogeneous fluorescence PCR assay for the diagnosis of infectious diseases. Analytical Sciences. 2000; 16:245-248.
Li, et al., Molecular Beacons: A Novel Approach to Detect Protein—DNA Interactions. Angew Chem Int Ed Engl. Mar. 2000;39(6):1049-1052.
Li, et al., Using molecular beacons as a sensitive fluorescence assay for enzymatic cleavage of single-stranded DNA. Nucleic Acids Res. Jun. 1, 2000; 28(11):E52.
Lindquist, et al., Characterization of the interaction between alphaCP(2) and the 3'- untranslated region of collagen alpha1(I) mRNA. Nucleic Acids Res. Nov. 1, 2000; 28(21):4306-16.
Liu, et al., A fiber-optic evanescent wave DNA biosensor based on novel molecular beacons. Anal Chem. Nov. 15, 1999; 71(22):5054-9.
Liu, et al., Molecular beacons for DNA biosensors with micrometer to submicrometer dimensions. Anal Biochem. Jul. 15, 2000;283(1):56-63.
Liu, et al., Probing the Electrostatics of Active Site Microenvironments along the Catalytic Cycle for *Escherichia coli* Dihydrofolate Reductase, J. Am. Chem. Soc. 2014, 136:10349-60.
Liu, et al., Real-time monitoring in vitro transcription using molecular beacons. Anal Biochem. Jan. 1, 2002; 300(1):40-5.
Liu, et al., Site-directed fluorescence labeling of P-glycoprotein on cysteine residues in the nucleotide binding domains. Biochemistry. Sep. 10, 1996;35(36):11865-73.
Lopez, et al., Convenient Methods for Patterning the Adhesion of Mammalian Cells to Surfaces Using Self-Assembled Monolayers of Alkanethiolates on Gold. J. Am. Chem. Soc. 1993; 115:5877-5878.
Lorber, et al., Flexible ligand docking using conformational ensembles. Protein Sci. Apr. 1998;7(4):938-50.
Lowman, et al., Selecting high-affinity binding proteins by monovalent phage display. Biochemistry. Nov. 12, 1991; 30(45):10832-8.

(56) References Cited

OTHER PUBLICATIONS

Macbeath, et al., Printing Proteins as Microarrays for High-Throughput Function Determination. Science. 2000; 289:1760-1763.

Magnuson, et al., The Raf-1 serine/threonine protein kinase.Semin Cancer Biol. Aug. 1994;5(4):247-53.

Majumdar, et al., Single-molecule FRET reveals sugar-induced conformational dynamics in LacY. Proc Natl Acad Sci U S A. Jul. 31, 2007;104(31):12640-5. Epub May 14, 2007.

Mallik, et al., Towards materials for the specific recognition and separation of proteins. New J. Chem. 1994; 18:299-304.

Manganelli, et al., Differential expression of 10 sigma factor genes in Mycobacterium tuberculosis. Mol Microbiol. Jan. 1999; 31(2):715-24.

Mannuzzu, et al., Direct physical measure of conformational rearrangement underlying potassium channel gating. Science. Jan. 12, 1996; 271(5246):213-6.

Manz, et al., T-cell triggering thresholds are modulated by the number of antigen within individual T-cell receptor clusters, PNAS, May 31, 2011, 108(22):9089-94.

Marks, et al., By-passing immunization. Human antibodies from V-gene libraries displayed on phage. J Mol Biol. Dec. 5, 1991;222(3):581-97.

Marlow, et al., The role of conformational entropy in molecular recognition by calmodulin, Nat. Chem. Biol. 2010, 6(5):352-8.

Marras, et al., Multiplex detection of single-nucleotide variations using molecular beacons. Genet Anal., Feb. 1999;14(5-6):151-6.

Marshall, et al., DNA chips: an array of possibilities. Nat Biotechnol. Jan. 1998;16(1):27-31.

Martin, et al., Immunospecific targeting of liposomes to cells: a novel and efficient method for covalent attachment of Fab' fragments via disulfide bonds. Biochemistry. Jul. 7, 1981; 20(14):4229-38.

Martin, et al., Irreversible coupling of immunoglobulin fragments to preformed vesicles. An improved method for liposome targeting. J Biol Chem. Jan. 10, 1982;257(1):286-8.

Martinson, et al., Global distribution of the CCR2-64I/CCR5-59653T HIV-1 disease-protective haplotype. AIDS. Mar. 31, 2000;14(5):483-9.

Matsu, in situ visualization of messenger RNA for basic fibroblast growth factor in living cells. Biochim Biophys Acta. Feb. 2, 1998;1379(2):178-84.

Matysiak, et al., Improved solid supports and spacer/linker systems for the synthesis of spatially addressable PNA-libraries. Nucleosides Nucleotides. 1999; 18:1289-1291.

McAllister, et al., DNA microarrays and genomic mismatch scanning: new genetic tools. Am. J. Hum. Genet. 1997; 61(4):1387.

McConnell, et al., Electronic and optical properties of chemically modified metal nanoparticles and molecularly bridged nanoparticle arrays. J. Phys. Chem. B. 2000; 104:8925-8930.

McHugh, et al., Construction, purification, and functional incorporation on tumor cells of glycolipid-anchored human B7-1 (CD80). Proc Natl Acad Sci U S A. Aug. 15, 1995;92(17):8059-63.

McKillip, et al., Molecular beacon polymerase chain reaction detection of *Escherichia coli* O157:H7 in milk. J Food Prot. Jul. 2000; 63(7):855-9.

Medintz, et al., Maltose-binding protein: a versatile platform for prototyping biosensing, Curr. Opin. Biotechnol, 2006, 17(1):17-27.

Menaa, et al., Favorable Influence of Hydrophobic Surfaces on Protein Structure in Porous Organically-modified Silica Glasses, Biomaterials, Jun. 2008, 29(18): 2710-8.

Menaa, et al., Protein Adsorption onto Organically Modified Silica Glass Leads to a Different Structure than Sol-Gel Encapsulation, Biophysical Journal: Biophysical Letters, 2008, L51-53.

Mesmaeker, et al., Backbone modifications in oligonucleotides and peptide nucleic acid systems. Curr. Opin. Struct. Biol. 1995; 5:343-355.

Metzner, et al., Effects of in vivo CD8(+) T cell depletion on virus replication in rhesus macaques immunized with a live, attenuated simian immunodeficiency virus vaccine. J Exp Med. Jun. 5, 2000; 191(11):1921-31.

Michael, et al., Randomly ordered addressable high-density optical sensor arrays. Anal Chem. Apr. 1, 1998; 70(7):1242-8.

Milosevic, et al., Extreme-ultraviolet harmonic generation near 13 nm with a two-color elliptically polarized laser field, 2000, Opt Lett, 25(20), 1532-1534.

Moreaux, et al., Membrane imaging by second harmonic generation microscopy. Journal of Optical Society of America B: Optical Physics. 2000; 17(10):1685-1694.

Moree, et al., Protein Conformational Changes Are Detected and Resolved Site Specifically by Second-Harmonic Generation. Biophys J. Aug. 18, 2015;109(4):806-15. doi: 10.1016/j.bpj.2015.07.016.

Mrksich, et al., Using self-assembled monolayers to understand the interactions of man-made surfaces with proteins and cells. Annu Rev Biophys Biomol Struct. 1996;25:55-78.

Mullah, et al., Efficient automated synthesis of molecular beacons. Nucleos Nucleot. 1999; 18:1311-1312.

Nagar, et al., Crystal structures of the kinase domain of c-Abl in complex with the small molecule inhibitors PD173955 and imatinib (STI-571). Cancer Research. 2002; 62:4236-4243.

Nazarenko, et al., A closed tube format for amplification and detection of DNA based on energy transfer. Nucleic Acids Res. Jun. 15, 1997;25(12):2516-21.

Needels, et al., Generation and screening of an oligonucleotide-encoded synthetic peptide library. Proc Natl Acad Sci U S A. Nov. 15, 1993;90(22):10700-4.

Nelson, et al., Bifunctional oligonucleotide probes synthesized using a novel CPG support are able to detect single base pair mutations. Nucleic Acids Res. Sep. 25, 1989;17(18):7187-94.

Neumann, et al., Functional immobilization of a ligand-activated G-protein-coupled receptor. Chembiochem. Oct. 4, 2002;3(10):993-8.

Nie, et al., Probing single molecules and single nanoparticles by surface-enhanced raman scattering. Science. 1997; 75:1102-1106.

Nielsen. Antisense Properties of Peptide Nucleic Acid. Handbook of Experimental Pharmacology. 1998; 131:545-560.

Nielsen. Applications of peptide nucleic acids. Curr Opin Biotechnol. 1999; 10:71-75.

Nielsen. Design of Sequence-Specific DNA-Binding Ligands. Chem. Eur. J. 1997; 3:505-508.

Nielsen, et al., Peptide nucleic acid (PNA). A DNA mimic with a pseudopeptide backbone. Chem. Soc. Rev. 1997; 73-78.

Nielsen, et al., Peptide nucleic acid (PNA), a new molecular tool. In Molecular Biology: Current Innovations and Future Trends, Part2. Horizon Scientific Press. 1995; 73-89.

Nielsen, et al., Peptide nucleic acids-(PNA): Oligonucleotide analogues with a polyamide backbone. Antisense Research and Applications. 1992; 363-372.

Nielsen, et al.,Peptide nucleic acids (PNAs): Potential Antisense and Anti-gene Agents. Anti-Cancer Drug Design. 1993; 8:53-63.

Nielsen, P. E. Dna analogues with nonphosphodiester backbonesAnnu Rev.Biomol.Struct. 24 (1995) 167-183.

Nielsen, P. E., Egholm, M. and Buchardt, 0. Peptide Nucleic Acid (PNA). A DNA mimic with a peptide backbone Bioconjugate Chemistry 5 (1994) 3-7.

Nielsen. Peptide nucleic acid (PNA): A lead for gene therapeutic drugs. Antisense Therapeutics. 1996; 4:76-84.

Nielsen. Peptide Nucleic Acids. Science and Medicine Planning. 1998; 48-55.

Nielsen. Sequence-specific recognition of double-stranded DNA by peptide nucleic acids. Advances in DNA Sequence-Specific Agents. 1998; 3:267-278.

Nielsen. Structural and Biological Properties of Peptide Nucleic Acid (PNA). Pure & Applied Chemistry. 1998; 70:105-110.

Noble, et al., Impact on Biophysical Parameters on the Biological Assessment of Peptide Nucleic Acids, Antisense Inhibitors of Gene Expression. Drug. Develop. Res. 1995; 34:184-195.

Noble, et al., Protein kinase inhibitors: insights into drug design from structure. Science. Mar. 19, 2004; 303(5665):1800-5.

(56) References Cited

OTHER PUBLICATIONS

Notice of allowance dated Apr. 11, 2016 for U.S. Appl. No. 14/396,494.
Notice of allowance dated Apr. 27, 2016 for U.S. Appl. No. 14/548,804.
Notice of allowance dated May 6, 2016 for U.S. Appl. No. 14/006,302.
Novak, et al., Assembly of Phenylacetylene-Bridged Silver and Gold 5 Nanoparticle Arrays. J. Am. Chem. Soc. 2000; 122:3979-3980.
Novak, et al., Nonlinear Optical Properties of Molecularly Bridged Gold Nanoparticle Arrays. J. Am. Chem. Soc. 2000; 122:12029-12030.
Nye, et al., Kinetic control of histidine-tagged protein surface density on supported lipid bilayers. Langmuir. Apr. 15, 2008;24(8):4145-9. doi: 10.1021/la703788h. Epub Feb. 28, 2008.
O'Donnell, et al., Thermodynamics and conformational change governing domain-domain interactions of calmodulin, Methods Enzymol, 2009, 466:503-26.
Office action dated Jan. 14, 2013 for U.S. Appl. No. 12/535,631.
Office action dated Jan. 30, 2015 for U.S. Appl. No. 13/834,521.
Office action dated Feb. 7, 2002 for U.S. Appl. No. 09/731,366.
Office action dated Feb. 16, 2011 for U.S. Appl. No. 12/571,342.
Office action dated Feb. 16, 2012 for U.S. Appl. No. 12/571,342.
Office action dated Feb. 23, 2004 for U.S. Appl. No. 09/731,366.
Office action dated Mar. 24, 2008 for U.S. Appl. No. 11/327,199.
Office action dated Mar. 30, 2009 for U.S. Appl. No. 11/327,199.
Office action dated Apr. 3, 2012 for U.S. Appl. No. 12/535,631.
Office action dated Apr. 14, 2015 for U.S. Appl. No. 13/834,809.
Office action dated Apr. 21, 2004 for U.S. Appl. No. 09/907,038.
Office action dated Apr. 21, 2015 for U.S. Appl. No. 13/838,340.
Office action dated Apr. 21, 2015 for U.S. Appl. No. 13/838,491.
Office action dated May 8, 2002 for U.S. Appl. No. 09/907,035.
Office action dated Jun. 18, 2007 for U.S. Appl. No. 11/327,199.
Office action dated Aug. 25, 2003 for U.S. Appl. No. 09/907,035.
Office action dated Sep. 10, 2004 for U.S. Appl. No. 09/731,366.
Office action dated Sep. 20, 2005 for U.S. Appl. No. 10/467,098.
Office action dated Oct. 2, 2012 for U.S. Appl. No. 12/571,342.
Office action dated Oct. 23, 2003 for U.S. Appl. No. 09/731,366.
Office action dated Oct. 28, 2002 for U.S. Appl. No. 09/731,366.
Office action dated Nov. 3, 2006 for U.S. Appl. No. 10/970,754.
Office action dated Nov. 8, 2016 for U.S. Appl. No. 13/834,521.
Office action dated Nov. 20, 2002 for U.S. Appl. No. 09/907,035.
Ong, et al., Polarization of water molecules at a charged interface: second harmonic studies of the silica/water interface. Chemical Physics Letters. 1992; 191:327-335.
Ortiz, et al., PNA molecular beacons for rapid detection of PCR amplicons. Mol Cell Probes. Aug. 1998;12(4):219-26.
Orum, et al., Peptide Nucleic Acid. Nucleic Acid Amplification Technologies: Application to Disease Diagnostics. 1997; 29-48.
Oudar, et al., Hyperpolarizabilities of the nitroanilines and their relations to the excited state dipole moment. J. Chem. Phys. 1977; 66. 2664-2668.
Oudar, et al., Optical nonlinearities of conjugated molecules. Stilbene derivatives and highly polar aromatic compounds. J. Chem. Phys. 1977; 67(2):446-457.
Paige, et al., Estrogen receptor (ER) modulators each induce distinct conformational changes in ER alpha and ER beta. Proc Natl Acad Sci U S A. Mar. 30, 1999;96(7):3999-4004.
Pantano, et al., Ordered nanowells arrays. Chem. Mater. 1996; 8:2832-2835.
Pargellis, et al., Inhibition of p38 MAP kinase by utilizing a novel allosteric binding site. Nat Struct Biol. Apr. 2002;9(4):268-72.
Park, et al., Rapid identification of Candida dubliniensis using a species-specific molecular beacon. J Clin Microbiol. Aug. 2000; 38(8):2829-36.
Paszti, et al., Sum frequency generation vibrational spectroscopy studies of protein adsorption on oxide-covered Ti surfaces. Journal of Physical Chemistry B. 2004; 108:7779-7787.

Peleg, et al., Nonlinear optical measurement of membrane potential around single molecules at selected cellular sites. Proc Natl Acad Sci U S A. Jun. 8, 1999;96(12):6700-4.
Perozo, et al., rearrangements underlying K+-channel activation gating. Science. Jul. 2, 1999; 285(5424):73-8.
Piatek, et al., Genotypic analysis of Mycobacterium tuberculosis in two distinct populations using molecular beacons: implications for rapid susceptibility testing. Antimicrob Agents Chemother. Jan. 2000; 44(1):103-10.
Piatek, et al., Molecular beacon sequence analysis for detecting drug resistance in Mycobacterium tuberculosis. Nat Biotechnol. Apr. 1998;16(4):359-63.
Pierce, et al., Real-time PCR using molecular beacons for accurate detection of the Y chromosome in single human blastomeres. Mol Hum Reprod. Dec. 2000; 6(12):1155-64.
Piunno, et al., Fiber-optic DNA sensor for fluorometric nucleic acid determination. Anal Chem. Aug. 1, 1995; 67(15):2635-43.
Poddar. Detection of adenovirus using PCR and molecular beacon. J Virol Methods. Sep. 1999; 82(1):19-26.
Poddar, Symmetric vs asymmetric PCR and molecular beacon probe in the detection of a target gene of adenovirus. Mol Cell Probes. Feb. 2000;14(1):25-32.
Polizzi, et al., (2004). Ellipsometric approach for the real-time detection of label-free protein absroption by second harmonic generation. Journal of the American Chemical Society. 2004; 126:5001-5007.
Potyrailo, et al., Adapting selected nucleic acid ligands (aptamers) to biosensors. Anal Chem. Aug. 15, 1998; 70(16):3419-25.
Spurlino, et al., The 2.3—A resolution structure of the maltose-or maltodextrin-binding protein a primary receptor of bacterial active transport and chemotaxis, J. Biol. Chem. 1991. 266(8):5202-19.
Quiocho, et al., Atomic structure and specificity of bacterial periplasmic receptors for active transport and chemotaxis: variation of common themes, Mol. Microbiol, 1996, 20(1):17-25.
Rajagopalan, et al., Interaction of dihydrofolate reductase with methotrexate: ensemble and single-molecule kinetics. Proc Natl Acad Sci U S A. Oct. 15, 2002;99(21):13481-6. Epub Oct. 1, 2002.
Ramsay, DNA chips-states-of-the-art. Nature Biotechnology. 1998; 16(1):40-44.
Reider, et al., Second-order Nonlinear Optical Effects at Surfaces and Interfaces: recent advances. In Electromagnetic Waves: Recent Developments in Research, vol. 2, Photonic Probes of Surfaces. Halevia, P., editor. Elsevier Science, Amsterdam. Chapter 9. 1995. 415-478.
Ren, et al., Cloning of linear DNAs in vivo by overexpressed T4 DNA ligase: construction of a T4 phage hoc gene display vector. Gene. Aug. 22, 1997;195(2):303-11.
Ren, et al., Phage display of intact domains at high copy number: a system based on SOC, the small outer capsid protein of bacteriophage T4. Protein Sci. Sep. 1996;5(9):1833-43.
Ren, et al., Phage T4 SOC and HOC display of biologically active, full-length proteins on the viral capsid. Gene. Jul. 30, 1998; 215(2):439-44.
Rhee, et al., Molecular epidemiologic evaluation of transmissibility and virulence of Mycobacterium tuberculosis. J Clin Microbiol. Jun. 1999;37(6):1764-70.
Rinuy, et al., Second harmonic generation of glucose oxidase at the air/water interface. Biophysial Journal., 1999; 77:3350-3355.
Rodriguez, et al., In vivo incorporation of multiple unnatural amino acids through nonsense and frameshift suppression. Proc Natl Acad Sci U S A. Jun. 6, 2006;103(23):8650-5. Epub May 25, 2006.
Sackmann,Supported membranes: scientific and practical applications. Science. Jan. 5, 1996; 271(5245):43-8.
Saha, et al., Quantitation of HIV-1 by real-time PCR with a unique fluorogenic probe. J Virol Methods. Apr. 2001; 93(1-2):33-42.
Salafsky, Detection of protein conformational change by optical second-harmonic generation. J Chem Phys. Aug. 21, 2006;125(7):074701.
Salafsky, et al., A second-harmonic-active unnatural amino acid as a structural probe of biomolecules on surfaces. J. Phys. Chem. B, 2008, 112 (47), pp. 15103-15107.

(56) References Cited

OTHER PUBLICATIONS

Salafsky, et al., Architecture and function of membrane proteins in planar supported bilayers: A study with photosynthetic reaction centers' Biochemistry. 1996; 35(47):14773-14781.
Salafsky, et al., Protein absorption at interfaces detected by second-harmonic generation.J. Phys. Chem. B. 2004; 108(10):3376. Additions and Corrections.
Salafsky, et al., Protein absorption at interfaces detected by second-harmonic generation.Journal of Physical Chemistry B. 2000; 104:7752-7755.
Salafsky, et al., Second Harmonic Spectroscopy: Detection and Orientation of Molecules at a Biomembrane Interface. Chemical Physics Letters 2000; 319:435-439.
Salafsky, et al., SHG labels for detection of molecules by second harmonic generation. Chemical Physics Letters. 2001; 342:485-491.
Salafsky, J. (Apr. 2008). Second-Harmonic Generation (SHG) for Identification of Allosteric D & Conformation-Specific Compounds PowerPoint Presentation presented to SBS, 30 pages.
Salafsky, J. (Apr. 15, 2009). Detection Method for Conformational Change Second-Harmonic Generation Provides a Molecular-Level, Functional Readout in Real Time Gen Eng & Biotech News, 2 pages.
Salafsky, Second-harmonic generation as a probe of conformational change in molecules. Chemical Physics Letters. 2003; 381(5):705-709.
Salafsky, Second-harmonic generation for studying structural motion of biological molecules in real time and space. Phys Chem Chem Phys. Nov. 14, 2007;9(42):5704-11. Epub Sep. 7, 2007.
Samanta, et al., Excited state dipole moment of Prodan as determined from transient dieletric loss measurements. Journal of Physical Chemistry A. 2000; 104:8972-8975.
Sandberg, et al., New chemical descriptors relevant for the design of biologically active peptides. A multivariate characterization of 87 amino acids. J Med Chem. Jul. 2, 1998; 41(14):2481-91.
Sauer-Eriksson, et al., Crystal structure of the C2 fragment streptococcal protein G in complex with the Fc domain of the human IgG. Structure. 1995; 3(3):265-278.
Schena, et al., Quantitative monitoring of gene expression patterns with a complementary DNA microarray. Science. Oct. 20, 1995; 270(5235):467-70.
Schindler, et al., Structural mechanism for STI-571 inhibition of abelson tyrosine kinase. Science. Sep. 15, 2000; 289(5486):1938-42.
Schofield, et al., Molecular beacons: trial of a fluorescence-based solution hybridization technique for ecological studies with ruminal bacteria. Appl Environ Microbiol. Mar. 1997; 63(3):1143-7.
Schoofs, et al., Epitopes of an influenza viral peptide recognized by antibody at single amino acid resolution. J Immunol. Jan. 15, 1988;140(2):611-6.
Scott, et al., Searching for peptide ligands with an epitope library. Science. Jul. 27, 1990; 249(4967):386-90.
Sebti, et al., Candida dubliniensis at a cancer center. Clin Infect Dis. Apr. 1, 2001;32(7):1034-8. Epub Mar. 15, 2001.
Seeliger, et al., High yield bacterial expression of active c-Abl and c-Src tyrosine kinases. Protein Sci. Dec. 2005;14(12):3135-9. Epub Oct. 31, 2005.
Seok, et al., Topology of allosteric regulation of lactose permease. Proc Natl Acad Sci U S A. Dec. 9, 1997; 94(25):13515-9.
Shen, Optical Second Harmonic Generation at Interfaces. Annual Review of Physical Chemistry. 1989; 40(1):327-350.
Shen, Surface properties probed by second-harmonic and sum-frequency generation. Nature. 1989; 337: 20 519-525.
Shen, The Principles of Nonlinear Optics, John Wiley & Sons, New York. 1984.
Shih, et al., Evidence that genetic instability occurs at an early stage of colorectal tumorigenesis. Cancer Res. Feb. 1, 2001; 61(3):818-22.
Shnek, et al., Specific Protein Attachment to Artificial Membranes via Coordination to Lipid-Bound Copper (II). Langmuir. 1994; 10:2382-2388.

Sicheri, Crystal structure of the Src family tyrosine kinase Hck. Nature. 1997; 385:602-609.
Sicheri, et al., Structures of Src-family tyrosine kinases. Current Opinion in Structural Biology. 1997; 7:777-785.
Sigal, et al., A self-assembled monolayer for the binding and study of histidine-tagged proteins by surface plasmon resonance. Anal Chem. Feb. 1, 1996;68(3):490-7.
Singer, et al., Measurements of molecular second-order optical susceptibilities using dc-induced second harmonic generation. J. Chem. Phys. 1981; 75:3572-3580.
Singhvi, et al., Engineering cell shape and function. Science. Apr. 29, 1994;264(5159):696-8.
Sittampalam, et al., High-throughput screening: advances in assay technologies. Curr Opin Chem Biol. Oct. 1997;1(3):384-91.
Smit, et al., Semiautomated DNA mutation analysis using a robotic workstation and molecular beacons. Clin Chem. Apr. 2001;47(4):739-44.
Smith, et al., Libraries of peptides and proteins displayed on filamentous phage. Methods Enzymol. 1993; 217:228-57.
Smith. Surface presentation of protein epitopes using bacteriophage expression systems. Curr Opin Biotechnol. Oct. 1991; 2(5):668-73.
Sokol, et al., Real time detection of DNA.RNA hybridization in living cells. Proc Natl Acad Sci U S A. Sep. 29, 1998; 95(20):11538-43.
Sonnichsen, et al., Spectroscopy of single metallic nanoparticles using total internal reflection microscopy. Appl. Phys. Lett. 2000; 77(19):2949-2951.
Spargo, et al., Spatially controlled adhesion, spreading, and differentiation of endothelial cells on self-assembled molecular monolayers. Proc Natl Acad Sci U S A. Nov. 8, 1994;91(23):11070-4.
Sproat, et al., The synthesis of protected 5'-mercapto-2',5'-dideoxyribonucleoside-3'-O-phosphoramidites; uses of 5'-mercapto-oligodeoxyribonucleotides. Nucleic Acids Res. Jun. 25, 1987;15(12):4837-48.
Srivastava, et al., Kinetics of molecular transport across a liposome bilayer. Chem. Phys. Lett. 1998; 292 (3): 345-351.
Steemers, et al., Screening unlabeled DNA targets with randomly ordered fiber-optic gene arrays. Nat Biotechnol. Jan. 2000;18(1):91-4.
Steuerwald, et al., Analysis of gene expression in single oocytes and embryos by real-time rapid cycle fluorescence monitored RT-PCR. Mol Hum Reprod. Nov. 1999;5(11):1034-9.
Strouse, et al., Using molecular beacons to quantify low levels of type I endonuclease activity. Biopharm. 2000; 13:40-47.
Suh, et al., Morphology dependent contrast measurements of microscopically textured germanium films. Proc. SPIE. 1983; 382:199-201.
Summerer, et al., A genetically encoded fluorescent amino acid. Proc Natl Acad Sci U S A. Jun. 27, 2006;103(26):9785-9. Epub Jun. 19, 2006.
Szemes, et al., Development of a multiplex AmpliDet RNA assay for simultaneous detection and typing of potato virus Y isolates. J Virol Methods. Feb. 2002;100(1-2):83-96.
Szuhai, et al., a novel strategy for human papillomavirus detection and genotyping with SybrGreen and molecular beacon polymerase chain reaction. Am J Pathol. 2001 Nov;159(5):1651-60.
Szuhai, et al., Simultaneous A8344G heteroplasmy and mitochondrial DNA copy number quantification in myoclonus epilepsy and ragged-red fibers (MERRF) syndrome by a multiplex molecular beacon based real-time fluorescence PCR. Nucleic Acids Res. Feb. 1, 2001; 29(3):E13.
Staii, et al., Ligand-induced structural changes in maltose binding proteins measured by atomic force microscopy, Nano Lett. 2008, 8(8):2503-9.
Takagi, et al., Global conformational rearrangements in integrin extracellular domains in outside-in and inside-out signaling. Cell. Sep. 6, 2002;110(5):599-11.
Tan, et al., Molecular beacons: a novel DNA probe for nucleic acid and protein studies. Chemistry. Apr. 3, 2000;6(7):1107-11.
Tapp, et al., Homogeneous scoring of single-nucleotide polymorphisms: comparison of the 5'-nuclease TaqMan assay and Molecular Beacon probes. Biotechniques. Apr. 2000;28(4):732-8.

(56) References Cited

OTHER PUBLICATIONS

The energetic cost of domain reorientation in maltose-binding protein as studied by NMR and fluorescence spectroscopy, Proc. Natl. Acad. Sci. USA 2003. 100(22):12700-5.
Thelwell, et al., Mode of action and application of Scorpion primers to mutation detection. Nucleic Acids Res. Oct. 1, 2000; 28(19):3752-61.
Theodossiou, et al., Thermally Induced Irreversible Conformational Changes in Collagen Probed by Optical Second Harmonic Generation and Laser-induced Fluorescence, 2002; 17:34-41.
Thermo Scietific Matrix Microplate Data Sheet, Available at: www.Thermos.com/matrix 1 page.
Thomas, Raman spectroscopy of protein and nucleic acid assemblies. Annual Review of Biophysics and Biomolecular Structure. 1999; 28:1-27.
Tompa, et al., Intrinsically disordered proteins: a 10-year recap. Trends Biochem. Sci. 2012, 37(12):509-16.
Tung, et al., In vivo imaging of proteolytic enzyme activity using a novel molecular reporter. Cancer Res. Sep. 1, 2000; 60(17):4953-8.
Turcatti, et al., Probing the structure and function of the tachykinin neurokinin-2 receptor through biosynthetic incorporation of fluorescent amino acids at specific sites. J Biol Chem. Aug. 16, 1996; 271(33):19991-8.
Tyagi, et al., Molecular beacons: probes that fluoresce upon hybridization. Nat Biotechnol. Mar. 1996;14(3):303-8.
Tyagi, et al., Multicolor molecular beacons for allele discrimination. Nat Biotechnol. Jan. 1998;16(1):49-53.
Tyagi, et al., Wavelength-shifting molecular beacons. Nat Biotechnol. Nov. 2000;18(11):1191-6.
Uddin, et al., A fiber optic biosensor for fluorimetric detection of triple-helical DNA. Nucleic Acids Res. Oct. 15, 1997;25(20):4139-46.
Uhlmann, et al., PNA: Synthetic polyamide nucleic acids with unusual binding properties. Angewandte Chemie-International Edition. 1998; 37:2797-2823.
Uhlmann. Peptide nucleic acids (PNA) and PNA-DNA chimeras: from high binding affinity towards biological function. Biol Chem. 1998; 379:1045-52.
Valentin, et al., CXCR4 mediates entry and productive infection of syncytia-inducing (X4) HIV-1 strains in primary macrophages. Virology. Apr. 10, 2000;269(2):294-304.
Van Beuningen, et al., Development of a high-throughput detection system for HIV-1 using real-time NASBA based on molecular beacons. Proceedings—SPIE the International Society for Optical Engineering. 2001; 4264, 66-71.
Van Schie, et al., Semiautomated clone verification by real-time PCR using molecular beacons. Biotechniques. Dec. 2000;29(6):1296-300, 1302-4, 1306 passim.
Vance, et al., Enormous Hyper-Rayleigh Scattering from Nanocrystalline Gold Particle Suspensions. J. Phys. Chem. B. 1999; 102:10091-93.
Venkitakrishnan, et al., Conformational Changes in the Active Site Loops of Dihydrofolate Reductase during the Catalytic Cycle, Biochemistry 2004, 43:16046-55.
Vet, et al., Multiplex detection of four pathogenic retroviruses using molecular beacons. Proc Natl Acad Sci U S A. May 25, 1999;96(11):6394-9.
Villarroel, et al., The ever changing moods of calmodulin: how structural plasticity entails transductional adaptability, J. Mol. Biol. 2014, 426(15):2717-35.
Vogelstein, et al., Digital PCR. Proc Natl Acad Sci U S A. Aug. 3, 1999; 96(16):9236-41.
Walt, Techview: molecular biology. Bead-based fiber-optic arrays. Science. Jan. 21, 2000; 287(5452):451-2.
Wang, DNA biosensors based on peptide nucleic acid (PNA) recognition layers. A review. Biosens Bioelectron. 1998; 13:757-62.
Wang, et al., In situ, nonlinear optical probe of Surfactant Adsorption on the Surface of Microparticles in Colloids. Langmuir 2000, 16, 2475-2481.
Wang, et al., Polarity of liquid interfaces by second harmonic generation spectroscopy, 1997, J Phys Chem A, 101, 713-718.
Watson, et al., Technology for microarray analysis of gene expression. Curr Opin Biotechnol. Dec. 1998; 9(6):609-14.
Weber, et al., Synthesis and spectral properties of a hydrophobic fluorescent probe: 6-propionyl-2-(dimethylamino) naphthalene. Biochemistry. Jul. 10, 1979;18(14):3075-8.
Weisz, Polyamides as artificial regulators of gene expression. Angew. Chem. Int. Ed. Eng. 1997; 36:2592-2594.
Weljie, et al., Protein conformational changes studied by diffusion NMR spectroscopy: Application to helix-loop-helix calcium binding proteins. Protein Science. 2003; 12:228-235.
Wettstein, et al., Expression of a class II major histocompatibility complex (MHC) heterodimer in a lipid-linked form with enhanced peptide/soluble MHC complex formation at low pH. J Exp Med. Jul. 1, 1991;174(1):219-28.
Whitcombe, et al., Detection of PCR products using self-probing amplicons and fluorescence. Nat Biotechnol. Aug. 1997;17(8):804-7.
Wittung, et al., Recognition of double-stranded DNA by peptide nucleic acid. Nucleosid. Nucleotid. 1997; 16599-602.
Xiao, et al., A DNA damage signal is required for p53 to activate gadd45. Cancer Res. Mar. 15, 2000; 60(6):1711-9.
Xie, et al., Innovation: A chemical toolkit for proteins—an expanded genetic code. Nature Reviews Molecular Cell Biology. 2006; 7:775-782.
Xu, et al., Crystal structures of c-Src reveal features of its autoinhibitory mechanism. Molecular Cell 3, 629-638 (1999).
Xu, et al., Three-dimensional structure of the tyrosine kinase c-Src. Nature. 1997 385:595-602.
Yamamoto, et al., Molecular beacon aptamer fluoresces in the presence of Tat protein of HIV-1. Genes Cells. May 2000;5(5):389-96.
Yang, et al., Spectral broadening of ultrashort pulses in a nonlinear medium. Opt Lett. Nov. 1, 1984;9(11):510-2.
Yang, et al., Surface second harmonic generation (SSHG)—a new scheme for immunoassay. Proceedings of the SPIE. 1996; 2676:290-296. http://dx.doi.org/10.1117/12.238808.
Yates, et al., Quantitative detection of hepatitis B virus DNA by real-time nucleic acid sequence-based amplification with molecular beacon detection. J Clin Microbiol. Oct. 2001; 39(10):3656-65.
Yellen, The moving parts of voltage-gated ion channels. Q Rev Biophys. Aug. 1998; 31(3):239-95.
Ying, et al., Two-state model of conformational fluctuation in a DNA hairpin-loop. Chemical Physics Letters. 2001; 334:145-150.
Zhang, et al., A chemilluminescence fiber-optic biosensor for detection of DNA hybridization. Anal., Lett. 1999; 32:2725-2736.
Zhang, et al., Design of a Molecular Beacon Dna Probe with Two Fluorophores. Angew Chem Int Ed Engl. Jan. 19, 2001; 40(2):402-405.
Zhang, et al., Measuring recent thymic emigrants in blood of normal and HIV-1-infected individuals before and after effective therapy. J Exp Med. Sep. 6, 1999;190(5):725-32.
Zhu, et al., Inhibition of vascular endothelial growth factor-induced receptor activation with anti-kinase insert domain-containing receptor single-chain antibodies from a phage display library. Cancer Res. Aug. 1, 1998; 58(15):3209-14.
Zhuang, et al., Mapping molecular orientation and conformation at interfaces by surface nonlinear optics. Physical Review B. 1999; 59(19):12632-12640.
Zimdars, et al., Static and Dynamic Solvation at the Air/Water Interface. Journal of Physical Chemistry B. 2001; 105:3993-4002.
Zuckermann, et al., Efficient methods for attachment of thiol specific probes to the 3'-ends of synthetic oligodeoxyribonucleotides. Nucleic Acids Res. Jul. 10, 1987;15(13):5305-21.
EP 15874284.1 Extended Search Report and Written Opinion dated May 2, 2018.
Lauer et al. Development and Characterization of Ni-NTA-Bearing Microspheres, Cytometry, Jun. 27, 2002, 48(3):136-145.
U.S. Appl. No. 13/834,521 Office Action dated May 9, 2018.

(56) References Cited

OTHER PUBLICATIONS

Campagnola, et al. Second-harmonic imaging microscopy for visualizing biomolecular arrays in cells, tissues and organisms. Nat Biotechnol. Nov. 2003;21(11):1356-60. Published online Oct. 31, 2003; doi:10.1038/nbt894.
Castellana et al. Solid Supported Lipid Bilayers: From Biophysical Studies to Sensor Design. Surface Science Reports 61(10):429-444 (Nov. 15, 2006).
Co-pending U.S. Appl. No. 10/484,658, filed Jul. 17, 2002.
Co-pending U.S. Appl. No. 11/002,620, filed Dec. 2, 2004.
Co-pending U.S. Appl. No. No. 15/211,859, filed Jul. 15, 2016.
Co-pending U.S. Appl. No. 16/452,045, filed Jun. 25, 2019.
Co-pending U.S. Appl. No. 16/562,223, filed Sep. 5, 2019.
EP15874284.1 Office Action dated Feb. 5, 2019.
Han et al. Different Interfacial Behaviors of Peptides Chemically Immobilized on Surfaces with Different Linker Lengths and via Different Termini. J Phys Chem 118:2904-2912 (Feb. 20, 2014). DOI: dx.doi.org/10.1021/jp4122003.
Heinz. Second-Order Nonlinear Optical Effects at Surfaces and Interfaces. Chapter 5 of Nonlinear Surface Electromagnetic Phenomena. Edited by H. E. Ponath and G. I. Stegeman. 1991.
Kang, et al. Specific adsorption of histidine-tagged proteins on silica surfaces modified with Ni2+/NTA-derivatized poly(ethylene glycol). Langmuir. May 22, 2007;23(11):6281-8. Epub Apr. 20, 2007.
Matar, et al. Second Harmonic Generation, a new approach for analyzing the interfacial properties of a short tryptophan-rich peptide. Chemical Physics Letters. vol. 500, pp. 161-166, (2010).
Matysiak. Improved solid supports and spacer/linker systems for the synthesis of spatially addressable PNA-libraries. Nucleosides Nucleotides. 1999; 18(6-7):1289-1291.
McGuinness, et al. Direct, Real-time Detection of Protein Conformation: Revealing Therapeutic Opportunities Using Second Harmonic Generation (SHG) Detection. Biodesy, LLC. Poster M143. Mar. 18-21, 2011.
Millard, et al. Second harmonic imaging microscopy. Methods Enzymol. 2003;361:47-69.
MJFF. Development of modulators of alpha-synuclein conformation for PD therapeutics. MJFF grant abstract. 2008.
MJFF. Development of Potent Conformation-Specific Compounds Directed to Monomeric Alpha-Synuclein. MJFF grant abstract. 2009.
MJFF. Development of SHG to Discover Drugs to Selectively Block AlphaS toxicity. MJFF grant abstract. 2007.
MJFF. Partnering program. Organization and team overview. 2009.
NSF. SBIR Phase I: Development of a Conformational Screen for Rapidly Identifying Kinase Inhibitor Type Using SHG. NSF SBIR grant abstract. 2011.
NSF. SBIR Phase I: Development of a Conformational Screen for Rapidly Identifying Kinase Inhibitor Type Using SHG. NSF SBIR grant abstract. 2012.
NSF. SBIR Phase II: Development of an SHG Instrument, Artemis QuantTM, for measuring conformational change in real time. NSF SBIR grant abstract. 2013.
Oral Abstracts from the Society of Biomolecular Sciences 14th Annual Conference and Exhibition: St. Louis, Missouri Apr. 6-10, 2008. J. Biomol Screen 2008 13: 697. DOI: 10.1177/1087057108322219.
Pitchford, et al. Direct, Real-time Detection of Kinase Type II Inhibitors Using Second Harmonic Generation (SHG) Detection. Biodesy, LLC. Poster T380. Mar. 17, 2011.
Revision history of T380:Pitchford:SHGKinaseposter. Retrieved on Apr. 18, 2012. Retrieved from the internet: http://www.labautopedia.com/mw/index.php?title=T380:Pitchford:SHGKinasePoster&action=history.
Salafsky, et al. Real-time measurement of protein conformational change in key therapeutic targets: application to Abl kinase and mutant Ras. Biodesy, LLC. SLAS2012 talk abstract. Nov. 2011.
Salafsky. Real-time detection of GPCR conformational change. NIH grant abstract. 2005-2007.
Salafsky. Real-time measurement of protein conformational change in key therapeutic targets: applications to Abl-kinase and mutant Ras. Biodesy, LLC. SLAS Conference. PPT presentation. Feb. 7, 2012.
Salafsky. Second-Harmonic Generation (SHG) for Identification of Allosteric and Conformation-Specific Compounds. Journal of Biomolecular Screening. 2008; 13(7):697.
Salafsky. SHG for integrin receptor drug discoverye. NIH grant abstract. 2006-2007.
Vanzi, et al., Protein conformation and molecular order probed by second-harmonic-generation microscopy, Journal of Biomedical Optics, Jun. 18, 2012, 17(6):060901, 8 Pages.
Wartchow, et al. Assaying protein conformational change in real time—a novel approach for target-based drug discovery. Biodesy, LLC. SLAS2012 Roche poster. Feb. 6-8, 2012.
Wu, et al. Protein immobilization on Ni(II) ion patterns prepared by microcontact printing and dip-pen nanolithography. ACS Nano. Feb. 23, 2010;4(2):1083-91. Published online Jan. 27, 2010. doi: 10.1021/nn901270c.
You, et al. Affinity capturing for targeting proteins into micro and nanostructures. Anal Bioanal Chem. Mar. 2009;393(6-7):1563-70. doi: 10.1007/s00216-008-2595-6. Epub Jan. 20, 2009.

* cited by examiner

ATTACHMENT OF PROTEINS TO INTERFACES FOR USE IN NONLINEAR OPTICAL DETECTION

CROSS-REFERENCE

This application is a Continuation Application of International Patent Application Ser. No. PCT/US2015/067285, filed Dec. 22, 2015, which claims the benefit of U.S. Provisional Patent Application Ser. No. 62/096,334, filed Dec. 23, 2014, which applications are incorporated herein by reference in their entireties.

BACKGROUND

Second harmonic generation (SHG) is a nonlinear optical process which may be configured as a surface-selective detection technique that enables detection of conformational change in proteins and other biological targets (as described previously, for example, in U.S. Pat. Nos. 6,953,694 and 8,497,703). In order to deploy SHG-based detection of conformational change in a convenient and high throughput format, it will be advantageous to design novel methods for immobilizing proteins on substrate surfaces, and novel mechanisms for rapid, precise, and interchangeable positioning of substrates (comprising the tethered biological targets to be analyzed) with respect to the optical system used to deliver excitation light, which ensure that both a high degree of orientation of the protein molecules at the optical interface and efficient optical coupling between the excitation light and the substrate surface are maintained.

The methods and compositions disclosed herein provide means for tethering or immobilizing protein molecules on optical interfaces in a manner that ensures both uniform surface coverage of the optical interface and a high degree of orientation of the molecules, thereby providing for significant enhancements of SHG and other nonlinear optical signals and improved signal-to-noise ratios.

SUMMARY

Disclosed herein are methods for tethering a biological entity to a substrate comprising: (a) forming a supported lipid bilayer on a surface of a substrate, wherein the supported lipid bilayer
comprises an anchor molecule that comprises or bears a first affinity tag that is present in the lipid bilayer at a concentration greater than or equal to 5 mole percent; and (b) contacting the supported lipid bilayer with a biological entity, wherein the biological entity comprises a nonlinear-active label and a second affinity tag capable of binding to the first affinity tag, thereby tethering the biological entity to the supported lipid bilayer in an oriented fashion. In some aspects, the methods further comprise detecting a non-linear optical signal arising from the tethered biological entity.

In some aspects, the substrate is fabricated from a material selected from the group consisting of glass, fused-silica, a polymer, or any combination thereof. In some aspects, the first affinity and
second affinity tags are Ni-NTA and poly-histidine tags. In some aspects, the poly-histidine tag is attached to the N-terminus of a protein. In some aspects, the poly-histidine tag is attached to the C-terminus of a protein. In some aspects, the poly-histidine tag comprises between 4 and 24 histidine residues. In some aspects, the poly-histidine tag comprises 8 histidine residues. In some aspects, the poly-histidine tag comprises 6 histidine residues. In some aspects, the first affinity tag comprises Co-CMA and the second affinity tag comprises a poly-histidine tag. In some aspects, the first affinity tag comprises biotin and the second affinity tag comprises streptavidin. In some aspects, the first affinity tag comprises biotin and the second affinity tag comprises avidin. In some aspects, the first affinity tag comprises biotin and the second affinity tag comprises neutravidin. In some aspects, the non-linear optical signal is second harmonic light. In some aspects, the non-linear optical signal is sum frequency light. In some aspects, the non-linear optical signal is difference frequency light. In some aspects, the biological entity is selected from the group consisting of cells, proteins, peptides, receptors, enzymes, antibodies, DNA, RNA, biological molecules, oligonucleotides, small molecules, synthetic molecules, carbohydrates, or any combination thereof. In some aspects, the anchor molecule comprising the first affinity tag is adjusted to a value ranging from 5 mole percent to 100 mole percent of the lipid bilayer. In some aspects, the non-linear optical signal detected increases by at least 5× when the concentration of the anchor molecule comprising the first affinity tag is increased by a factor of 2×. In some aspects, the non-linear optical signal detected increases by at least 10× when the concentration of the anchor molecule comprising the first affinity tag is increased by a factor of 2×. In some aspects, the non-linear optical signal detected increases by at least 20× when the concentration of the anchor molecule comprising the first affinity tag is increased by a factor of 2×. In some aspects, the dependence of the non-linear optical signal on the concentration of the anchor molecule comprising the first affinity tag is described by a power law having an exponent greater than 2. In some aspects, the methods further comprise incubating the supported lipid bilayer with the biological entity for about 10 minutes to about 60 minutes. In some aspects, the biological entity is present at a concentration of about 0.1 uM to 10 uM. In some aspects, the supported lipid bilayer comprises 1,2-dioleoyl-sn-glycero-3-phosphocholine. In some aspects, the anchor molecule conjugated to the first affinity tag comprises 1,2-dioleoyl-sn-glycero-3-[(N-(5-amino-1-carboxypentyl)
iminodiacetic acid)succinyl] (nickel salt). In some aspects, the biological entity is a protein. In some aspects, the protein is present at a concentration of less than 2 uM. In some aspects, the amount of protein used is less than 500 ng.

Also disclosed herein are methods for detecting conformational change in a biological entity comprising: (a) illuminating a substrate with one or more light beams at one or more fundamental frequencies, wherein the substrate comprises a supported lipid bilayer, and wherein the supported lipid bilayer further comprises a Ni-NTA bearing lipid present at a concentration of greater than 5 mole percent, and wherein a biological entity comprising a non-linear active label and poly-histidine tag is tethered to the supported lipid bilayer; (b) measuring a non-linear optical signal arising from the tethered biological entity; (c) optionally contacting the tethered biological entity with one or more candidate binding partners; (d) optionally measuring a non-linear optical signal arising from the tethered biological entity in contact with the one or more candidate binding partners; and (e) optionally comparing the non-linear optical signals measured in steps (b) and (d) to detect a conformational change in the biological entity.

In some aspects, the substrate is fabricated from a material selected from the group consisting of glass, fused-silica, a polymer, or any combination thereof. In some aspects, the biological entity is a protein and the poly-histidine tag is attached to the N-terminus of the protein. In some aspects, the biological entity is a protein and the poly-histidine tag is attached to the C-terminus of the protein. In some aspects, the poly-histidine tag comprises between 4 and 24 histidine residues. In some aspects, the poly-histidine tag comprises 8 histidine residues. In some aspects, the polyhistidine tag comprises 6 histidine residues. In some aspects, the non-linear optical signal is second harmonic light. In some aspects, the non-linear optical signal is sum frequency light. In some aspects, the non-linear optical signal is difference frequency light. In some aspects, the supported lipid bilayer comprises 1,2-dioleoyl-sn-glycero-3-phosphocholine. In some aspects, the Ni-NTA bearing lipid comprises 1,2-dioleoyl-sn-glycero-3-[(N-(5-amino-1-carboxypentyl)iminodiacetic acid)succinyl] (nickel salt). In some aspects, the biological entity is selected from the group consisting of cells, proteins, peptides, receptors, enzymes. antibodies, DNA, RNA, biological molecules, oligonucleotides, small molecules, synthetic molecules, carbohydrates, or any combination thereof. In some aspects, the biological entity is a protein. In some aspects, the protein is present at a concentration of less than 2 uM. In some aspects, the amount of protein used is less than 500 ng.

Disclosed herein are devices comprising: (a) a substrate, wherein the substrate further comprises a supported lipid bilayer; and (b) a biological entity, wherein the biological entity comprises a non-linear active label and is tethered to the supported lipid bilayer using a pair of affinity tags, and wherein one of the affinity tags is attached to the supported lipid bilayer by means of an anchor molecule that is present in the bilayer at a concentration of greater than or equal to 5 mole percent, and the other affinity tag is attached to the biological entity; wherein the device is capable of producing a non-linear optical signal when exposed to excitation light.

In some aspects, the substrate is fabricated from a material selected from the group consisting of glass, fused-silica, a polymer, or any combination thereof. In some aspects, one of the affinity tags comprises Ni-NTA and the other affinity tag comprises a poly-histidine tag. In some aspects, the poly-histidine tag is attached to the N-terminus of a protein. In some aspects, the poly-histidine tag is attached to the C-terminus of a protein. In some aspects, the poly-histidine tag comprises between 4 and 24 histidine residues. In some aspects, the poly-histidine tag comprises 8 histidine residues. In some aspects, the poly histidine tag comprises 6 histidine residues. In some aspects, one of the affinity tags comprises Co-CMA and the other affinity tag comprises a poly-histidine tag. In some aspects, one of the affinity tags comprises biotin and the other affinity tag comprises streptavidin. In some aspects, one of the affinity tags comprises biotin and the other affinity tag comprises avidin. In some aspects, one of the affinity tags comprises biotin and the other affinity tag comprises neutravidin. In some aspects, the non-linear optical signal is second harmonic light. In some aspects, the non-linear optical signal is sum frequency light. In some aspects, the non-linear optical signal is difference frequency light. In some aspects, the biological entity is selected from the group consisting of cells, proteins, peptides, receptors, enzymes, antibodies, DNA, RNA, biological molecules, oligonucleotides, small molecules, synthetic molecules, carbohydrates, or any combination thereof. In some aspects, the supported lipid bilayer comprises 1,2-dioleoyl-sn-glycero-3-phosphocholine. In some aspects, the anchor molecule bearing the first affinity tag comprises 1,2-dioleoyl-sn-glycero-3-([N-(5-amino-1-carboxypentyl) iminodiacetic acid)succinyl] (nickel salt). In some aspects, the concentration of the anchor molecule bearing one of the affinity tag is adjusted to a value ranging from 5 mole percent to 100 mole percent.

Disclosed herein are kits comprising: (a) a device comprising a substrate; (h) a lipid suspension, wherein the lipid suspension is capable of forming a supported lipid bilayer on a surface of the substrate and further comprises a lipid hearing a first affinity tag at a concentration of greater than or equal to 5 mole percent of the components capable of forming a supported lipid bilayer; and (c) reagents for tethering biological entities to the supported lipid bilayer using a second affinity tag that is capable of binding to the first affinity tag.

In some aspects, the substrate is fabricated from a material selected from the group consisting of glass, fused-silica, a polymer, or any combination thereof. In some aspects, the first and second affinity tags comprise Ni-NTA and poly-histidine tags. In some aspects, the poly-histidine tag is attached to the N-terminus of a protein. In some aspects, the poly-histidine tag is attached to the C-terminus of a protein. In some aspects, the poly-histidine tag comprises between 4 and 24 histidine residues. In some aspects, the poly-histidine tag comprises 8 histidine residues. In some aspects, the poly-histidine tag comprises 6 histidine residues. In some aspects, the first and second affinity tags comprise biotin- and streptavidin-conjugated reagents. In some aspects, the first and second affinity tags comprise biotin- and avidin-conjugated reagents. In some aspects, the first and second affinity tags comprise biotin- and neutravidin-conjugated reagents. In some aspects, the biological entity is selected from the group consisting of cells, proteins, peptides, receptors, enzymes, antibodies, DNA, RNA, biological molecules, oligonucleotides, small molecules, synthetic molecules, carbohydrates, or any combination thereof. In some aspects, the lipid suspension comprises 1,2-dioleoyl-snglycero-3-phosphocholine. In some aspects, the lipid bearing the first affinity tag comprises 1,2-dioleoyl-sn-glycero-3-[(N-(5-amino-1-carboxypentyl)iminodiacetic acid) succinyl] (nickel salt).

Also disclosed herein are methods for tethering a biological entity to a substrate comprising: (a) forming a supported lipid bilayer on a surface of a substrate, wherein the supported lipid bilayer comprises an anchor molecule that comprises or bears a first affinity tag; and (b) contacting the supported lipid bilayer with a biological entity present at a concentration less than or equal to 2 uM, or in an amount of less than or equal to 500 ng, wherein the biological entity comprises a nonlinear-active label and a second affinity tag capable of binding to the first affinity tag, thereby tethering the biological entity to the supported lipid bilayer in an oriented fashion. In some aspects, the methods further comprise detecting a non-linear optical signal arising from the tethered biological entity.

In some aspects, the substrate is fabricated from a material selected from the group consisting of glass, fused-silica, a polymer, or any combination thereof. In some aspects, the first affinity and second affinity tags are Ni-NTA and poly-histidine tags. In some aspects, the poly-histidine tag is attached to the N-terminus of a protein. In some aspects, the poly-histidine tag is attached to the C-terminus of a protein. In some aspects, the poly-histidine tag comprises between 4 and 24 histidine residues. In some aspects, the poly-histidine tag comprises 8 histidine residues. In some aspects, the poly-histidine tag comprises 6 histidine residues. In some aspects, the first affinity tag comprises Co-CMA and the second affinity tag comprises a poly-histidine tag. In some aspects, the first affinity tag comprises biotin and the second affinity tag comprises streptavidin. In some aspects, the first affinity tag comprises biotin and the second affinity tag comprises avidin. In some aspects, the first affinity tag comprises biotin and the second affinity tag comprises neutravidin. In some aspects, the non-linear optical signal is second harmonic light. In some aspects, the non-linear optical signal is sum frequency light. In some aspects, the non-linear optical signal is difference frequency light. In some aspects, the biological entity is selected from the group consisting of cells, proteins, peptides, receptors, enzymes. antibodies, DNA, RNA, biological molecules, oligonucleotides, small molecules, synthetic molecules, carbohydrates, or any combination thereof. In some aspects, the anchor molecule comprising the first affinity tag is adjusted to a value ranging from 5 mole percent to 100 mole percent of the lipid bilayer. In some aspects, the non-linear optical signal detected increases by at least 5× when the concentration of the anchor molecule comprising the first affinity tag is increased by a factor of 2×. In some aspects, the non-linear optical signal detected increases by at least 10× when the concentration of the anchor molecule comprising the first affinity tag is increased by a factor of 2×. In some aspects, the non-linear optical signal detected increases by at least 20× when the concentration of the anchor molecule comprising the first affinity tag is increased by a factor of 2×. In some aspects, the dependence of the non-linear optical signal on the concentration of the anchor molecule comprising the first affinity tag is described by a power law having an exponent greater than 2. In some aspects, the methods further comprise incubating the supported lipid bilayer with the biological entity for about 10 minutes to about 60 minutes. In some aspects, the biological entity is present at a concentration of about 0.1 uM to 10 uM. In some aspects, the supported lipid bilayer comprises 1,2-dioleoyl-sn-glycero-3-phosphocholine. In some aspects, the anchor molecule conjugated to the first affinity tag comprises 1,2-dioleoyl-sn-glycero-3-[(N-(5-amino-1-carboxypentyl) iminodiacetic acid)succinyl] (nickel salt).

Disclosed herein are methods for detecting conformational change in a biological entity comprising: (a) illuminating a substrate with one or more light beams at one or more fundamental frequencies, wherein the substrate comprises a supported lipid bilayer, and wherein the supported lipid bilayer further comprises a Ni-NTA hearing lipid, and wherein a biological entity comprising a non-linear active label and poly-histidine tag is tethered to the supported lipid bilayer by contacting the lipid bilayer with the biological entity at a concentration less than or equal to 2 uM or in an amount less than or equal to 500 ng; (b) measuring a non-linear optical signal arising from the tethered biological entity; (c) optionally contacting the tethered biological entity with one or more candidate binding partners; (d) optionally measuring a non-linear optical signal arising from the tethered biological entity in contact with the one or more candidate binding partners; and (e) optionally comparing the non-linear optical signals measured in steps (b) and (d) to detect a conformational change in the biological entity.

In some aspects, the substrate is fabricated from a material selected from the group consisting of glass, fused-silica, a polymer, or any combination thereof. In some aspects, the biological entity is a protein and the poly-histidine tag is attached to the N-terminus of the protein. In some aspects, the biological entity is a protein and the poly-histidine tag is attached to the C-terminus of the protein. In some aspects, the poly-histidine tag comprises between 4 and 24 histidine residues. In some aspects, the poly-histidine tag comprises 8 histidine residues. In some aspects, the poly-histidine tag comprises 6 histidine residues. In some aspects, the non-linear optical signal is second harmonic light. In some aspects, the non-linear optical signal is sum frequency light. In some aspects, the non-linear optical signal is difference frequency light. In some aspects, the supported lipid bilayer comprises 1,2-dioleoyl-sn-glycero-3-phosphocholine. In some aspects, the Ni-NTA bearing lipid comprises 1,2-dioleoyl-sn-glycero-3-[(N-(5-amino-1-carboxypentyl)iminodiacetic acid)succinyl] (nickel salt). In some aspects, the biological entity is selected from the group consisting of cells, proteins, peptides, receptors, enzymes, antibodies, DNA, RNA, biological molecules, oligonucleotides, small molecules, synthetic molecules, carbohydrates, or any combination thereof.

INCORPORATION BY REFERENCE

All publications, patents, and patent applications mentioned in this specification are herein incorporated by reference in their entirety to the same extent as if each individual publication, patent, or patent application was specifically and individually indicated to be incorporated by reference in their entirety. In the event of a conflict between a term herein and a term in an incorporated reference, the term herein controls.

BRIEF DESCRIPTION OF THE DRAWINGS

The novel features of the disclosed methods and devices are set forth with particularity in the appended claims. A better understanding of the features and advantages of the presently disclosed methods and devices will be obtained by reference to the following detailed description that sets forth illustrative embodiments, in which the principles of the novel designs are utilized, and the accompanying drawings of which:

DETAILED DESCRIPTION

The methods and compositions disclosed herein provide means for tethering or immobilizing protein molecules on optical interfaces in a manner that ensures both uniform surface coverage of the optical interface and a high degree of orientation of the molecules, thereby providing for significant enhancements of SHG and/or other nonlinear optical signals arising from the tethered protein molecules, as well as improved signal-to-noise ratios.

In some aspects of the present disclosure, methods are described for determining orientation, conformation, or changes in orientation or conformation of biological entities in response to contacting the biological entities with one or more test entities. As used herein, determining orientation, conformation, or changes thereof may involve measurement of a nonlinear optical signal which is related to and/or proportional to the average orientation of a nonlinear-active label or tag. In general, the methods disclosed rely on the use of second harmonic generation (SHG) or related nonlinear optical techniques (e.g. sum frequency generation (SFG) or difference frequency generation (DFG)) for detection of orientation, conformation, or conformational change, as described previously, for example, in U.S. Pat. Nos. 6,953, 694, and 8,497,703.

Detection of Conformation Using Second Harmonic Generation

Figures 1A, 1B:
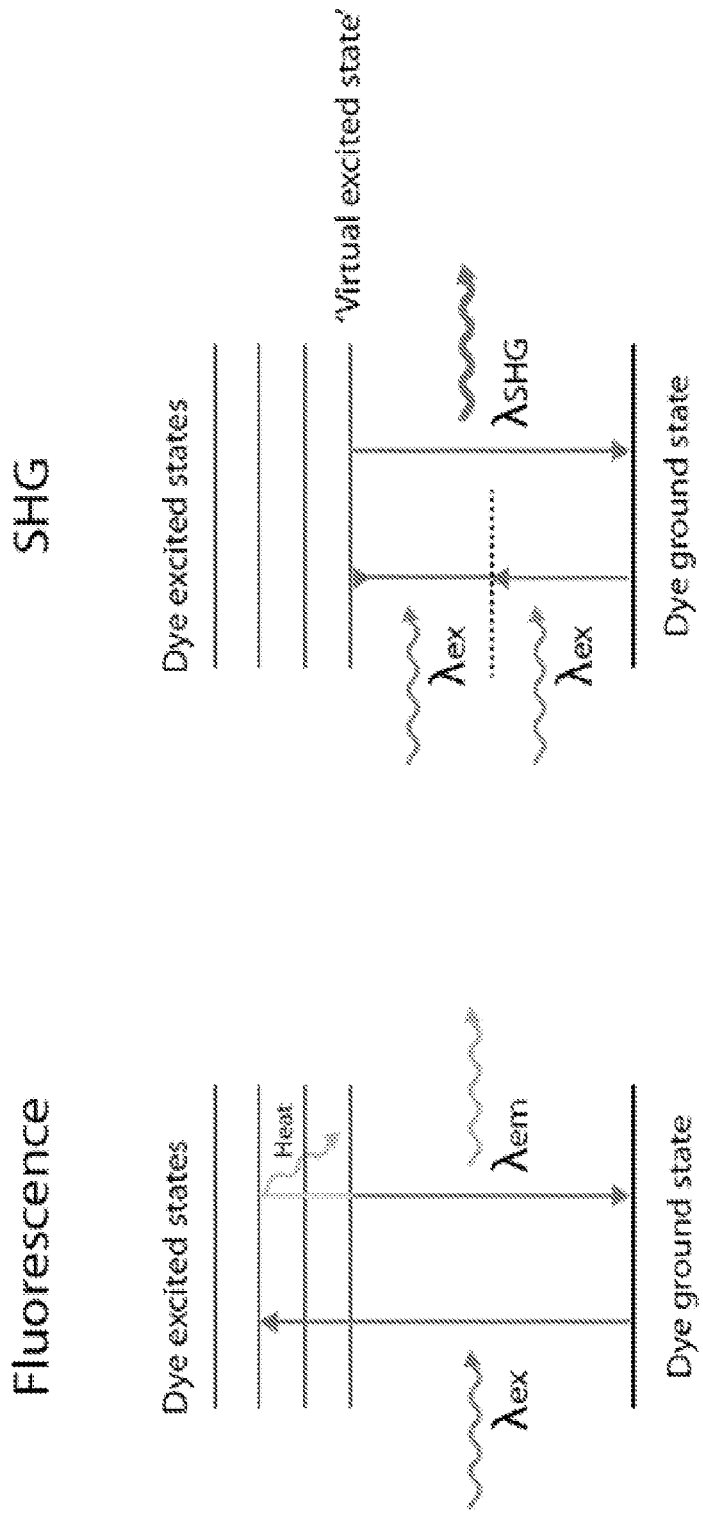
FIG. 1A provides a schematic illustration of the energy level diagram for fluorescence (an absorption process).
FIG. 1B provides a schematic illustration of the energy level diagram for second harmonic generation (a two photon scattering process).

Second harmonic generation, in contrast to more widely used fluorescence-based techniques (FIG. 1A), is a nonlinear optical process, in which two photons of the same excitation wavelength or frequency interact with a nonlinear material and are re-emitted as a single photon having twice the energy, i.e. twice the frequency and half the wavelength, of the excitation photons (FIG. 1B). Second harmonic generation only occurs in nonlinear materials lacking inversion symmetry (i.e. in non-centrosymmetric materials), and requires a high intensity excitation light source. It is a special case of sum frequency generation, and is related to other nonlinear optical phenomena such as difference frequency generation.

Second harmonic generation and other nonlinear optical techniques can be configured as surface-selective detection techniques because of their dependence on the orientation of the nonlinear-active species. Tethering of the nonlinear-active species to a planar surface. for example, can instill an overall degree of orientation that is absent when molecules are free to undergo rotational diffusion in solution. An equation commonly used to model the orientation-dependence of nonlinear-active species at an interface is:

$$\chi^{(2)} = N_s \langle \alpha^{(2)} \rangle \qquad (1)$$

where $\chi^{(2)}$ is the nonlinear susceptibility. $N_s$ is the total number of nonlinear-active molecules per unit area at the interface, and $\langle \alpha^{(2)} \rangle$ is the average orientation of the nonlinear hyperpolarizability ($\alpha^{(2)}$) of these molecules. The intensity of SHG is proportional to the square of the nonlinear susceptibility, and is thus dependent on both the number of oriented nonlinear-active species at the interface and on changes in their average orientation.

Second harmonic generation and other nonlinear optical techniques may be rendered additionally surface selective through the use of total internal reflection as the mode for delivery of the excitation light to the optical interface on which nonlinear-active species have been immobilized. Total internal reflection of the incident excitation light creates an "evanescent wave" at the interface, which may be used to selectively excite only nonlinear-active labels that are in close proximity to the surface, i.e. within the spatial decay distance of the evanescent wave, which is typically on the order of tens of nanometers. Total internal reflection may also be used to excite fluorescence in a surface-selective manner, for example to excite a fluorescence donor attached to the optical interface, which then transfers energy to a suitable acceptor molecule via a fluorescence resonance energy transfer (FRET) mechanism. In the present disclosure, the evanescent wave generated by means of total internal reflection of the excitation light is preferentially used to excite a nonlinear-active label or molecule. The efficiency of exciting nonlinear active species depends strongly on both their average orientation and on their proximity to the interface.

Figure 2:
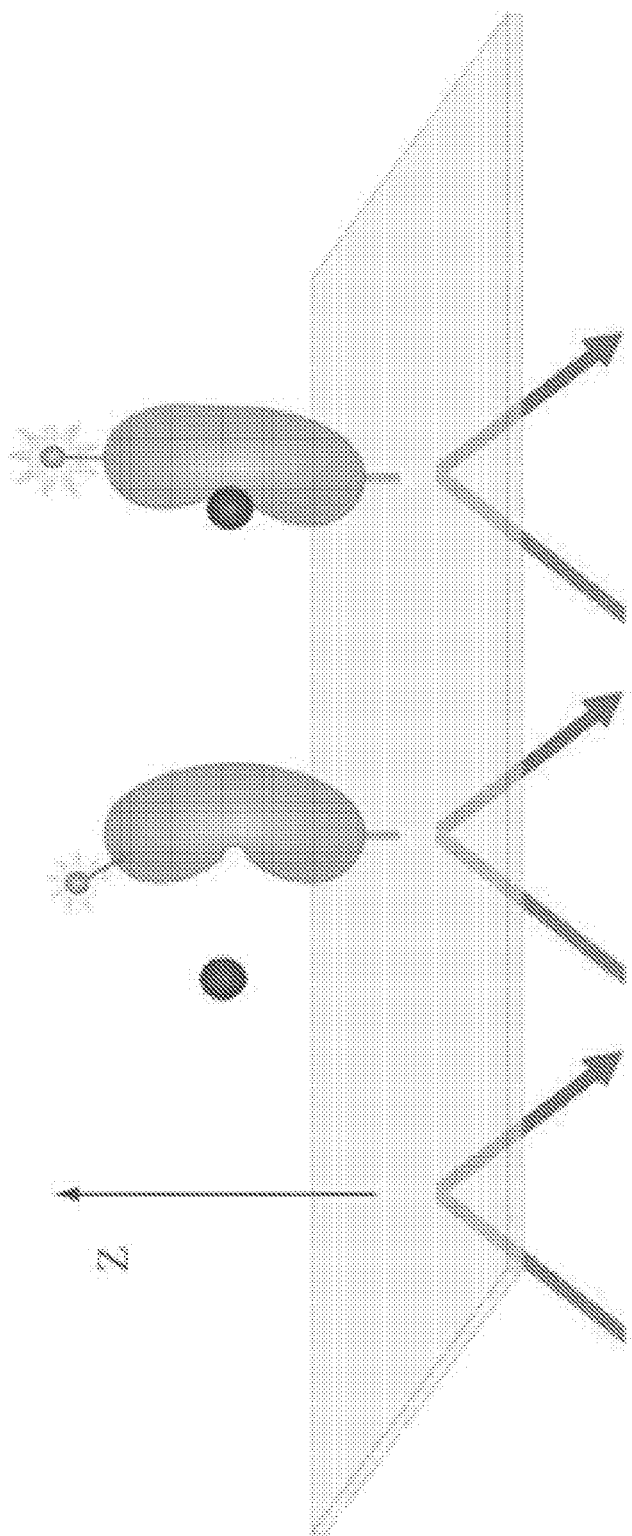
FIG. 2 provides a schematic illustration of a conformational change in a protein (labeled with a nonlinear-active tag) which is induced by binding of a ligand, and its impact on the distance and/or orientation of a nonlinear-active label relative to an optical interface to which the protein is attached. Incident laser light strikes the surface and through total internal reflection creates an evanescent wave. Labeled protein is bound to the surface and the measured SHG signal magnitude depends on the average, net orientation of the dye label relative to the surface normal (z-axis). A conformational change that re-orients the label results in signal changes.

This surface selective property of SHG and other nonlinear optical techniques can be exploited to detect conformational changes in biological molecules immobilized at interfaces. For example, a conformational change in a receptor molecule that results from binding of a ligand to the receptor might be detected using a nonlinear-active label or moiety, where the label is attached to or associated with the receptor in such a way that the conformational change leads to a change in the orientation or distance of the label with respect to the interface (FIG. 2), and thus to a change in a physical property of the nonlinear optical signal. In the past, the use of surface-selective nonlinear optical techniques has been confined mainly to applications in physics and chemistry, since relatively few biological samples are intrinsically non-linearly active. Recently, the use of second harmonic active labels ("SHG labels") has been introduced, allowing virtually any molecule or particle to be rendered highly non-linear active. The first example of this was demonstrated by labeling the protein cytochrome c with an oxazole dye and detecting the protein conjugate at an air-water interface with second harmonic generation (Salafsky (2006), Chem. Physics Letters 342(5-6):485-491). Surface-selective nonlinear optical techniques are also coherent techniques, meaning that the fundamental and nonlinear optical light beams have wave fronts that propagate through space with well-defined spatial and phase relationships. The use of surface-selective nonlinear optical detection techniques for analysis of conformation of biological molecules or other biological entities has a number of inherent advantages over other optical approaches, including: i) sensitive and direct dependence of the nonlinear signal on the orientation and/or dipole moment(s) of the nonlinear-active species, thereby conferring sensitivity to conformational change; (ii) higher signal-to-noise (lower background) than fluorescence-based detection since the nonlinear optical signal is generated only at surfaces that create a non-centrosymmetric system, i.e. the technique inherently has a very narrow "depth-of-field"; (iii) as a result of the narrow "depth of field", the technique is useful when measurements must be performed in the presence of a overlaying solution, e.g. where a binding process might be obviated or disturbed by a separation or rinse step. This aspect of the technique may be particularly useful for performing equilibrium binding measurements, which require the presence of bulk species, or kinetics measurements where the measurements are made over a defined period of time; (iv) the technique exhibits lower photobleaching and heating effects than those that occur in fluorescence, due to the facts that the two-photon absorption cross-section is typically much lower than the one-photon absorption cross-section for a given molecule, and that SHG (and sum frequency generation or difference frequency generation) involves scattering, not absorption; (v) minimal collection optics are required and higher signal to noise is expected since the fundamental and nonlinear optical beams (e.g., second harmonic light) have well-defined incoming and outgoing directions with respect to the interface. This is particularly advantageous compared to fluorescence-based detection, as fluorescence emission is isotropic and there may also be a large fluorescence background component to detected signals arising from out-of-focal plane fluorescent species.

Biological Entities and Test Entities

The methods and compositions disclosed herein are often applied to the tethering or immobilization of proteins. However, in some embodiments they may also be applied to tethering or immobilization of other biological entities. As used herein, the phrase "biological entities" comprises but is not limited to cells, proteins, peptides, receptors, enzymes, antibodies, DNA, RNA, biological molecules, oligonucleotides, small molecules, synthetic molecules, carbohydrates, or any combination thereof. Similarly, the phrase "test entities" also comprises but is not limited to cells, proteins, peptides, receptors, enzymes, antibodies, DNA, RNA, biological molecules, oligonucleotides, solvents, small molecules, synthetic molecules, carbohydrates, or any combination thereof. In some aspects, biological entities may comprise drug targets, or portions thereof, while test entities may comprise drug candidates, or portions thereof.

Nonlinear-Active Labels and Labeling Techniques

As noted above, most biological molecules are not intrinsically nonlinear-active. Exceptions include collagen, a structural protein that is found in most structural or load-bearing tissues. SHG microscopy has been used extensively in studies of collagen-containing structures, for example, the cornea. Other biological molecules or entities must be rendered nonlinear-active by means of introducing a nonlinear-active moiety such as a tag or label. A label for use in the presently disclosed methods refers to a nonlinear-active moiety, tag, molecule, or particle which can be hound, either covalently or non-covalently, to a molecule, particle, or phase (e.g., a lipid bilayer) in order to render the resulting system more nonlinear optical active. Labels can be employed in the case where the molecule, particle or phase (e.g., lipid bilayer) is not nonlinear active to render the system nonlinear-active, or with a system that is already nonlinear-active to add an extra characterization parameter to the system. Exogenous labels can be pre-attached to the molecules, particles, or other biological entities, and any unbound or unreacted labels separated from the labeled entities before use in the methods described herein. In a specific aspect of the methods disclosed herein, the nonlinear-active moiety is attached to the target molecule or biological entity in vitro prior to immobilizing the target molecules or biological entities in discrete regions of the substrate surface. The labeling of biological molecules or other biological entities with nonlinear-active labels allows a direct optical means of detecting interactions between the labeled biological molecule or entity and another molecule or entity (i.e. the test entity) in cases where the interaction results in a change in orientation or conformation of the biological molecule or entity using a surface-selective nonlinear optical technique.

In alternative aspects of the methods and systems described herein, at least two distinguishable nonlinear-active labels are used. The orientation of the attached two or more distinguishable labels would then be chosen to facilitate well defined directions of the emanating coherent nonlinear light beam. The two or more distinguishable labels can be used in assays where multiple fundamental light beams at one or more frequencies, incident with one or more polarization directions relative to the optical interface are used, with the resulting emanation of at least two nonlinear light beams.

Examples of nonlinear-active tags or labels include, but are not limited to, the compounds listed in Table 1, and their derivatives.

TABLE 1

Examples of Nonlinear-Active Tags

| 2-aryl-5-(4-pyridyl) oxazole | Hemicyanines | Polyimides |
| 2-(4-pyridyl)-cycloalkano[d] oxazoles | Indandione-1,3-pyidinium betaine | Polymethacrylates |

TABLE 1-continued

Examples of Nonlinear-Active Tags

| 5-aryl-2-(4-pyridyl) oxazole | Indodicarbocyanines | PyMPO (pyridyloxazole) |
| 7-Hydroxycoumarin-3-carboxylic acid, succinimidyl ester | Melamines | PyMPO, succinimidyl ester (1-(3-(succinimidyloxycarbonyl)benzyl)-4-(5-(4-PyMPO, maleimide |
| Azo dyes | Merocyanines | Stilbazims |
| Benzooxazoles | Methoxyphenyboxazol-2-yl)pyridinium bromide) | Stilbenes |
| Bithiophenes | Methylene blue | Stryryl-based dyes |
| Cyanines | Oxazole or oxadizole molecules | Sulphonyl-substituted azobenzenes |
| Dapoxyl carboxylic acid, succinimidyl ester | Oxonols | Thiophenes |
| Diaminobenzene compounds | Perylenes | Tricyanovinyl aniline |
| Diazostilbenes | Phenothiazine-stilbazole | Tricyanovinyl azo |
| Fluoresceins | Polyenes | |

In evaluating whether a species may be nonlinear-active, the following characteristics can indicate the potential for nonlinear activity: a large difference dipole moment (difference in dipole moment between the ground and excited states of the molecule), a large Stokes shift in fluorescence, or an aromatic or conjugated bonding character. In further evaluating such a species, an experimenter can use a simple technique known to those skilled in the art to confirm the nonlinear activity, for example, through detection of SHG from an air-water interface on which the nonlinear-active species has been distributed. Once a suitable nonlinear-active species bas been selected for the experiment at hand, the species can be conjugated, if desired, to a biological molecule or entity for use in the surface-selective nonlinear optical methods and systems disclosed herein.

The following reference and references therein describe techniques available for creating a labeled biological entity from a synthetic dye and many other molecules: Greg T. Hermanson, Bioconjugate Techniques, Academic Press. 1996.

In a specific aspect of the methods and systems disclosed, metal nanoparticles and assemblies thereof are modified to create biological nonlinear-active labels. The following references describe the modification of metal nanoparticles and assemblies: J. P. Novak and D. L. Feldheim, "Assembly of Phenylacetylene-Bridged Silver and Gold Nanoparticle Arrays". J. Am. Chem. Soc., 2000, 122, 3979-3980; J. P. Novak et al., "Nonlinear Optical Properties of Molecularly Bridged Gold Nanoparticle Arrays". J. Am. Chem. Soc. 2000, 122, 12029-12030; Vance, F W, Lemon B. I., Hupp, J. T., "Enormous Hyper-Rayleigh Scattering from Nanocrystalline Gold Particle Suspensions". J. Phys. Chem. B 102: 10091-93 (1999).

In yet another aspect of the methods and systems disclosed herein, the nonlinear activity of the system can also be manipulated through the introduction of nonlinear analogues to molecular beacons, that is, molecular beacon probes that have been modified to incorporate a nonlinear-active label (or modulator thereof) instead of fluorophores and quenchers. These nonlinear optical analogues of molecular beacons are referred to herein as molecular beacon analogues (MB analogues or MBA). The MB analogues to be used in the described methods and systems can be synthesized according to procedures known to one of ordinary skill in the art.

Types of Biological Interactions Detected

The methods and systems disclosed herein provide for detection of a variety of interactions between biological entities, or between biological entities and test entities, depending on the choice of biological entities, test entities, and non-linear active labeling technique employed. In one aspect, the present disclosure provides for the qualitative detection of binding events, e.g. the binding of a ligand to a receptor, as indicated by the resulting conformational change induced in the receptor. In another aspect, the present disclosure provides for quantitative analysis of binding events, e.g. the binding of a ligand to a receptor, by performing replicate measurements using different concentrations of the ligand molecule and generating a dose-response curve using the percent change in maximal conformational change observed. Similarly, other aspects of the present disclosure may provide methods for qualitative or quantitative measurements of enzyme-inhibitor interactions, antibody-antigen interactions, the formation of complexes of biological macromolecules, or interactions of receptors with allosteric modulators.

In other specific embodiments, MB analogues can be used according to the methods disclosed herein as hybridization probes that can detect the presence of complementary nucleic acid target without having to separate probe-target hybrids from excess probes as in solution-phase hybridization assays, and without the need to label the targets oligonucleotides. MB analogue probes can also be used for the detection of RNAs within living cells, for monitoring the synthesis of specific nucleic acids in sample aliquots drawn from bioreactors, and for the construction of self-reporting oligonucleotide arrays. They can be used to perform homogeneous one-well assays for the identification of single-nucleotide variations in DNA and for the detection of pathogens or cells immobilized to surfaces for interfacial detection.

Interactions between biological entities or biological and test entities (e.g. binding reactions, conformational changes, etc.) can be correlated through the methods presently disclosed to the following measurable nonlinear signal parameters: (i) the intensity of the nonlinear light, (ii) the wavelength or spectrum of the nonlinear light, (iii) the polarization of the nonlinear light, (iv) the time-course of (i), (ii), or (iii), and/or vi) one or more combinations of (i), (ii), (iii), and (iv).

Substrate Formats, Optical Interface, and Total Internal Reflection

As described above, the systems and methods of the present disclosure typically utilize a planar substrate for immobilization of one or more biological entities on a top surface of the substrate, wherein the top substrate surface further comprises the optical interface (or sample interface) used for exciting nonlinear optical signals. The substrate can be glass, silica, fused-silica, plastic, or any other solid material that is transparent to the fundamental and second harmonic light beams, and that supports total internal reflection at the substrate/sample interface when the excitation light is incident at an appropriate angle.

In some aspects of the disclosed immobilization chemistries, the substrate (or solid support) upon which biological entities are immobilized may be non-planar, for example, the substrate may comprise a convex, concave, or irregular surface, or may comprise glass beads, polymer beads, and the like. A bead or particle may comprise any type of solid, porous, or hollow bead or particle. A bead or particle may comprise a discrete shape that may be spherical (e.g., a microsphere) or have a non-spherical or irregular shape, such as cubic, cuboid, pyramidal, cylindrical, conical, oblong, or disc-shape, and the like. A bead or particle may refer to any three dimensional structure that provides an increased surface area for immobilization of biological entities. Beads or particles may comprise a variety of materials including, but not limited to, paramagnetic materials (e.g. magnesium, molybdenum, lithium, and tantalum), superparamagnetic materials (e.g. ferrite ($Fe_3O_4$); magnetite nanoparticles), ferromagnetic materials (e.g. iron, nickel, cobalt, some alloys thereof, and some rare earth metal compounds), ceramic, plastic, glass, polystyrene, silica, methylstyrene, acrylic polymers, titanium, latex, sepharose, agarose, hydrogel, polymer, cellulose, nylon, and any combination thereof.

In some aspects of the disclosed methods, the biological entities may be immobilized uniformly across a substrate surface. In other embodiments, the biological entities may be immobilized in one or more discrete regions of a substrate surface. In some embodiments, the discrete regions within which biological entities are contained are configured as one-dimensional or two-dimensional arrays, or are distributed randomly across the substrate surface, and are separated from one another by means of a hydrophobic coating or thin metal layer. In other aspects, the discrete regions may comprise indents in the substrate surface. In still other aspects, the discrete regions may be separated from each other by means of a well-forming component such that the substrate forms the bottom of a microwell plate (or microplate), and each individual discrete region forms the bottom of one well in the microwell plate. In one aspect of the present disclosure, the well-forming component separates the top surface of the substrate into 96 separate wells. In another aspect, the well-forming component separates the top surface of the substrate into 384 wells. In yet another aspect, the well-forming component separates the top surface of the substrate into 1,536 wells. In all of these aspects, the substrate, whether configured in a planar array, indented array, or microwell plate format, may comprise a disposable or consumable device or cartridge that interfaces with other optical and mechanical components of a high throughput analysis system.

The methods and systems disclosed herein further comprise specifying the number of discrete regions or wells into which the substrate surface is divided, irrespective of how separation is maintained between discrete regions or wells. Having larger numbers of discrete regions or wells on a substrate may be advantageous in terms of increasing the sample analysis throughput of the method or system. In one aspect of the present disclosure, the number of discrete regions or wells per substrate is between 10 and 1,600. In other aspects, the number of discrete regions or wells is at least 10, at least 20, at least 50, at least 100, at least 200, at least 300, at least 400, at least 500, at least 750, at least 1,000, at least 1,250, at least 1,500, or at least 1,600. In yet other aspects of the disclosed methods and systems, the number of discrete regions or wells is at most 1,600, at most 1,500, at most 1,000, at most 750, at most 500, at most 400, at most 300, at most 200, at most 100, at most 50, at most 20, or at most 10. In a preferred aspect, the number of discrete regions or wells is 96. In another preferred aspect, the number of discrete regions or wells is 384. In yet another preferred aspect, the number of discrete regions or wells is 1,536. Those of skill in the art will appreciate that the number of discrete regions or wells may fall within any range bounded by any of these values (e.g. from about 12 to about 1,400).

The methods and systems disclosed herein also comprise specifying the surface area of the discrete regions or wells into which the substrate surface is divided, irrespective of how separation is maintained between discrete regions or wells. Having discrete regions or wells of larger area may facilitate ease-of-access and manipulation of the associated biological entities in some cases, whereas having discrete regions or wells of smaller area may be advantageous in terms of reducing assay reagent volume requirements and increasing the sample analysis throughput of the method or system. In one aspect of the present disclosure, the surface area of the discrete regions or wells is between 1 mm$^2$ and 100 mm$^2$. In other aspects, the area of the discrete regions or wells is at least 1 mm$^2$, at least 2.5 mm$^2$, at least 5 mm$^2$, at least 10 mm$^2$, at least 20 mm$^2$, at least 30 mm$^2$ at least 40 mm$^2$, at least 50 mm$^2$, at least 75 mm$^2$, or at least 100 mm$^2$. In yet other aspects of the disclosed methods and systems, the area of the discrete regions or wells is at most 100 mm$^2$, at most 75 mm$^2$, at most 50 mm$^2$, at most 40 mm$^2$, at most 30 mm$^2$, at most 20 mm$^2$, at most 10 mm$^2$, at most 5 mm$^2$, at most 2.5 mm$^2$, or at most 1 mm$^2$. In a preferred aspect, the area of discrete regions or wells is about 35 mm$^2$. In another preferred aspect, the area of the discrete regions or wells is about 8.6 mm$^2$. Those of skill in the art will appreciate that the area of the discrete regions or wells may fall within any range bounded by any of these values (e.g. from about 2 mm$^2$ to about 95 mm$^2$).

In some embodiments, one or more discrete regions of the substrate surface are simultaneously exposed to (illuminated with) excitation light. In other embodiments, one or more discrete regions of the substrate surface are sequentially exposed to (illuminated with) excitation light by re-positioning the substrate relative to the excitation light source. Total internal reflection of the incident excitation light creates an "evanescent wave" at the sample interface, which excites the nonlinear-active labels immobilized thereon, and results in generation of second harmonic light (or in some aspects sum frequency or difference frequency light). Because the intensity of the evanescent wave, and hence the intensity of the nonlinear optical signals generated, is dependent on the incident angle of the excitation light beam, precise orientation of the substrate plane with respect to the optical axis of the excitation beam and efficient optical coupling of the beam to the substrate is critical for achieving optimal SHG signal across the array of discrete regions. In some aspects of the present disclosure, total internal reflection is achieved by means of a single reflection of the excitation light from the substrate surface. In other aspects, the substrate may be configured as a waveguide such that the excitation light undergoes multiple total internal reflections as it propagates along the waveguide. In yet other aspects, the substrate may be configured as a zero-mode waveguide, wherein an evanescent field is created by means of nanofabricated structures.

Efficient optical coupling between the excitation light beam and the substrate is often achieved by use of an index-matching fluid such as mineral oil, mixtures of mineral oil and hydrogenated terphenyls, perfluorocarbon fluids, glycerin, glycerol, or similar fluids having a refractive index near 1.5, wherein the index-matching fluid is wicked between a prism used to guide the light beam and the lower surface of the substrate. Alternative approaches for creating efficient optical coupling of the excitation beam to the substrate in high throughput systems are described in U.S. patent application Ser. No. 14/754,465.

Immobilization Chemistries

As disclosed herein, substrates in any of the formats described above are further configured for immobilization of biological entities across at least one surface of the substrate or within specified discrete regions of a substrate surface. Immobilization of biological molecules or cells may be accomplished by a variety of techniques known to those of skill in the art, for example, through the use of aminopropyl silane chemistries to functionalize glass or fused-silica surfaces with amine functional groups, followed by covalent coupling using amine-reactive conjugation chemistries, either directly with the biological molecule of interest, or via an intermediate spacer or linker molecule. Non-specific adsorption may also be used directly or indirectly, e.g. through the use of BSA-N-hydroxysuccinimide (BSA-NHS) by first attaching a molecular layer of BSA to the surface and then activating it with N,N'-disuccinimidyl carbonate. The activated lysine, aspartate or glutamate residues on the BSA react with surface amines on proteins.

In a preferred aspect of the present disclosure, biological molecules may be immobilized on the surface by means of tethering to or embedding in "supported lipid bilayers", the latter comprising small patches of lipid bilayer confined to a silicon or glass surface by means of hydrophobic and electrostatic interactions, where the bilayer is "floating" above the substrate surface on a thin layer of aqueous buffer. Supported phospholipid bilayers can also be prepared with or without membrane proteins or other membrane-associated components as described, for example, in Salafsky et al. "Architecture and Function of Membrane Proteins in Planar Supported Bilayers: A Study with Photosynthetic Reaction Centers", Biochemistry 35 (47): 14773-14781 (1996); Gennis, R., Biomembranes, Springer-Verlag, 1989; Kalb et al., "Formation of Supported Planar Lipid Bilayers by Fusion of Vesicles to Supported Phospholipid Monolayers", Biochimica Biophysica Acta 1103:307-316 (1992); and Brian et al., "Allogeneic Stimulation of Cyto-toxic T-cells by Supported Planar Membranes." PNAS-Biological Sciences 81(19): 6159-6163 (1984). Supported phospholipid bilayers are well known in the art and there are numerous techniques available for their fabrication. Potential advantages of using supported lipid bilayers for immobilization of proteins or other biological entities on substrate surfaces or optical interfaces include (i) preservation of membrane protein structure for those proteins that typically span the cell membrane or other membrane components of cells and require interaction with the hydrophobic core of the bilayer for stabilization of secondary and tertiary structure, (ii) preservation of two dimensional lateral and rotational diffusional mobility for studying interactions between protein components within the bilayer, and (iii) preservation of molecular orientation, depending on such factors as the type of protein under study (i.e. membrane or soluble protein), how the bilayer membrane is formed on the substrate surface, and how the protein is tethered to the bilayer (in the case of soluble proteins). Supported bilayers, with or without tethered or embedded protein, should typically be submerged in aqueous solution to prevent their destruction when exposed to air.

Soluble proteins and other biological entities may be tethered or attached to the supported lipid bilayer in an oriented fashion using a number of different anchor molecules, linkers, and/or attachment chemistries. As used herein, "anchor molecules" are molecules which are embedded in the lipid bilayer, and may comprise fatty acid, glycerolipid, glycerophospholipid, sphingolipid, or other lipid or non-lipid molecules to which attachment moieties are conjugated. The concentration of anchor molecules in the supported lipid bilayer may range from about 1 mole percent to as much as 100 mole percent. In some embodiments, the concentration of anchor molecules in the supported lipid bilayer may be at least 1 mole percent, at least 2.5 mole percent, at least 5 mole percent, at least 10 mole percent, at least 20 mole percent, at least 30 mole percent, at least 40 mole percent, at least 50 mole percent, at least 60 mole percent, at least 70 mole percent, at least 80 mole percent, at least 90 mole percent, or 100 mole percent. In some embodiments, the concentration of anchor molecules in the supported lipid bilayer may be at most 100 mole percent, at most 90 mole percent, at most 80 mole percent, at most 70 mole percent, at most 60 mole percent, at most 50 mole percent, at most 40 mole percent, at most 30 mole percent, at most 20 mole percent, at most 10 mole percent, at most 5 mole percent, at most 2.5 mole percent, or at most 1 mole percent. Those of skill in the art will recognize that the concentration of anchor molecules in the supported lipid bilayer may have any value within this range, for example, about 8.5 mole percent.

Linker molecules are molecules used to provide spatial ("vertical") separation between the attachment point of the protein or other biological entity being tethered and the attachment point on the anchor molecule embedded in the plane of the lipid bilayer. Examples of suitable linker molecules include, but are not limited to, omega-amino fatty acids, polyethylene glycols, and the like.

Attachment moieties (also referred to as "affinity tags") are specific chemical structures or binding partners that provide for covalent or non-covalent binding between two biological entities. Examples of attachment moieties or affinity tags that are suitable for use in the methods disclosed herein include biotin and avidin (or biotin and streptavidin), and His-tag/Ni-NTA binding partners.

The high affinity, non-covalent biotin-streptavidin interaction is widely used in biological assay techniques to conjugate or immobilize proteins or other biological entities. Biotinylation of proteins enables capture by multivalent avidin or streptavidin molecules that are themselves adhered to a surface (e.g. glass slides or beads) or conjugated to another molecule (e.g. through the use of a biotin-streptavidin-biotin bridge or linker). The biotin moiety is sufficiently small that biotinylation typically doesn't interfere with protein function. The high affinity ($K_d$ of $10^{-14}$ M to $10^{-15}$ M) and high specificity of the binding interaction between biotin and avidin or streptavidin enables capture of biotinylated proteins of interest even from complex samples. Due to the extremely strong binding interaction, harsh conditions are needed to elute biotinylated protein from streptavidin-coated surfaces (typically 6 M guanidine HCl at pH 1.5), which will often denature the protein of interest. The use of monomeric forms of avidin or streptavidin, which have a decreased biotin-binding affinity of ~$10^{-8}$ M, may allow biotinylated proteins to be eluted with excess free biotin if necessary. In the methods disclosed herein, lipid molecules comprising biotin moieties may be incorporated into supported lipid bilayers for the purpose of immobilizing or tethering biotinylated proteins and/or other biotinylated biological entities to the bilayer via a biotin-avidin-biotin (or biotin-streptavidin-biotin) bridge.

Biotinylation of proteins and other biological entities may be performed by direct coupling, e.g. through conjugation of primary amines on the surface of a protein using N-hydroxysuccinimidobiotin (NHS-biotin). Alternatively, recombinant proteins are conveniently biotinylated using the AviTag approach. wherein the AviTag peptide sequence (GLNDIFEAQKIEWHE) is incorporated into the protein through the use of genetic engineering and protein expression techniques. The presence of the AviTag sequence allows biotinylation of the protein by treatment with the BirA enzyme.

His tag chemistry is another widely used tool for purification of recombinant proteins and other biomolecules. In this approach, a DNA sequence specifying a string of six to nine histidine residues, for example, may be incorporated into vectors used for production of recombinant proteins comprising 6xHis or poly-His tags fused to their N- or C-termini. His-tagged proteins can then be purified and detected as a result of the fact that the string of histidine residues binds to several types of immobilized metal ions, including nickel, cobalt and copper, under specific buffer conditions. Supports such as agarose beads or magnetic particles can be derivatized with chelating groups to immobilize the desired metal ions, which then function as ligands for binding and purification of the His-tagged biomolecules of interest. In the methods disclosed herein, the number of histidine residues incorporated into recombinant proteins may range from 1 residue to 24 residues, or more. In some embodiments, the number of histidine residues incorporated may be at least 1 residue, at least 2 residues, at least 4 residues, at least 6 residues, at least 8 residues, at least 10 residues, at least 12 residues, at least 14 residues, at least 16 residues, at least 18 residues, at least 20 residues, at least 22 residues, or at least 24 residues. In some embodiments, the number of histidine residues incorporated may be at most 24 residues, at most 22 residues, at most 20 residues, at most 18 residues, at most 16 residues, at most 14 residues, at most 12 residues, at most 10 residues, at most 8 residues, at most 6 residues, at most 4 residues, at most 2 residues, or at most 1 residue. Those of skill in the art will recognize that the number of histidine residues incorporated may have any value within this range, for example, 7 residues.

The chelators most commonly used to create His-tag ligands are nitrilotriacetic acid (NTA) and iminodiacetic acid (IDA). Once NTA- or IDA-conjugated supports are prepared, they can be "loaded" with the desired divalent metal (e.g., Ni, Co, Cu, or Fe). When using nickel as the metal, for example, the resulting affinity support is usually called a Ni-chelate, Ni-IDA or Ni-NTA support. Affinity purification of His-tagged fusion proteins is the most common application for metal-chelate supports in protein biology research. Nickel or cobalt metals immobilized by NTA-chelation chemistry are the systems of choice for this application.

In the methods disclosed herein, lipid molecules comprising Ni-NTA groups (or other chelated metal ions) may be incorporated into supported lipid bilayers for the purpose of immobilizing or tethering His-tagged proteins and other His-tagged biological entities to the bilayer. In some embodiment, the supported lipid bilayer may comprise, for example, 1,2-dioleoyl-sn-glycero-3-phosphocholine, and may also contain, for example, 1,2-dioleoyl-sn-glycero-3-[(N-(5-amino-1-carboxypentyl)iminodiacetic acid)succinyl] (nickel salt) at various concentrations. The concentration of 1,2-dioleoyl-sn-glycero-3-[(N-(5-amino-1-carboxypentyl) iminodiacetic acid)succinyl] (nickel salt) in the supported lipid bilayer may range from as little as 1 mole percent to as much as 100 mole percent. In some embodiments, the concentration of 1,2-dioleoyl-sn-glycero-3-[(N-(5-amino-1-carboxypentyl)iminodiacetic acid)succinyl] (nickel salt) may be at least 1 mole percent, at least 2.5 mole percent, at least 5 mole percent, at least 10 mole percent, at least 20 mole percent, at least 30 mole percent, at least 40 mole percent, at least 50 mole percent, at least 60 mole percent, at least 70 mole percent, at least 80 mole percent, at least 90 mole percent, or 100 mole percent. In some embodiments, the concentration of 1,2-dioleoyl-sn-glycero-3-[(N-(5-amino-1-carboxypentyl)iminodiacetic acid)succinyl] (nickel salt) in the supported lipid bilayer may be at most 100 mole percent, at most 90 mole percent, at most 80 mole percent, at most 70 mole percent, at most 60 mole percent, at most 50 mole percent, at most 40 mole percent, at most 30 mole percent, at most 20 mole percent, at most 10 mole percent, at most 5 mole percent, at most 2.5 mole percent, or at most 1 mole percent. Those of skill in the art will recognize that the concentration of 1,2-dioleoyl-sn-glycero-3-[(N-(5-amino-1-carboxypentyl)iminodiacetic acid)succinyl] (nickel salt) in the supported lipid bilayer may have any value within this range, for example, about 5.5 mole percent.

Poly-His tags bind best to chelated metal ions in near-neutral buffer conditions (physiologic pH and ionic strength). A typical binding/wash buffer consists of Tris-buffer saline (TBS) pH 7.2, containing 10-25 mM imidazole. The low-concentration of imidazole helps to prevent non-specific binding of endogenous proteins that have histidine clusters. Elution and recovery of captured His-tagged protein from chelated metal ion supports, when desired, is typically accomplished using a high concentration of imidazole (at least 200 mM). low pH (e.g., 0.1 M glycinc-HCl, pH 2.5), or an excess of strong chelator (e.g., EDTA). Immunoglobulins are known to have multiple histidines in their Fc region and can bind to chelated metal ion supports, therefore stringent binding conditions (e.g. using an appropriate concentration of imidazole) are necessary to avoid high levels of background binding if immunoglobulins are present in a sample at high relative abundance compared to the His-tagged proteins of interest. Albumins, such as bovine serum albumin (BSA), also have multiple histidines and can yield high levels of background binding to chelated metal ion supports in the absence of more abundant His-tagged proteins or the use of imidazole in the binding/wash buffer.

Control of Surface Density of Immobilized Biological Entities

In some embodiments of the disclosed methods, it may sometimes be desirable to vary the surface density of proteins or other biological entities that are immobilized on or tethered to the substrate surface comprising the optical interface. This can be accomplished in a variety of ways, as is well known to those of skill in the art. For example, in embodiments where proteins (or other biological entities) are coupled to the surface through the use of aminopropyl silane chemistries to functionalize glass or fused-silica surfaces with amine functional groups, followed by covalent coupling using amine-reactive conjugation chemistries and linker molecules, the ratio of bi-functional (e.g. comprising both a primary amine and carboxyl functional group) to mono-functional (e.g. comprising only a carboxyl functional group) linkers in the reaction mixture may be varied to control the surface density of primary amine functional groups available for coupling with the protein.

As another example, in embodiments of the disclosed methods where biotin-streptavidin binding interactions are used to tether biotinylated proteins to biotinylated lipid molecules incorporated into a supported lipid bilayer (via a biotin-streptavidin-biotin bridge), the mole percent of the biotinylated lipid molecule used to form the bilayer may be varied in order to control the surface density of biotin groups available for binding. The concentration of biotinylated lipid molecules may range from as little as 1 mole percent to as much as 100 mole percent. In some embodiments, the concentration of biotinylated lipid molecule in the supported lipid bilayer may be at least 1 mole percent, at least 2.5 mole percent, at least 5 mole percent, at least 10 mole percent, at least 20 mole percent, at least 30 mole percent, at least 40 mole percent, at least 50 mole percent, at least 60 mole percent, at least 70 mole percent, at least 80 mole percent, at least 90 mole percent, or 100 mole percent. In some embodiments, the concentration of biotinylated lipid molecule in the supported lipid bilayer may be at most 100 mole percent, at most 90 mole percent, at most 80 mole percent, at most 70 mole percent, at most 60 mole percent, at most 50 mole percent, at most 40 mole percent, at most 30 mole percent, at most 20 mole percent, at most 10 mole percent, at most 5 mole percent, at most 2.5 mole percent, or at most 1 mole percent. Those of skill in the art will recognize that the concentration of biotinylated lipid molecule in the supported lipid bilayer may have any value within this range, for example, about 8 mole percent. Alternatively, the concentration and/or incubation time used for attaching streptavidin to the biotinylated lipid bilayer (or for attaching the biotinylated protein to the tethered streptavidin molecules) may be varied. The concentration of streptavidin or biotinylated protein used may range from about 0.1 µM to about 10 µM, or more. In some embodiments, the concentration of streptavidin or biotinylated protein used may be at least 0.1 µM, at least 0.5 µM, at least 1 µM, at least 2 µM, at least 3 µM, at least 4 µM, at least 5 µM, at least 6 µM, at least 7 µM, at least 8 µM, at least 9 µM, or at least 10 µm. In some embodiments, the concentration of streptavidin or biotinylated protein used may be at most 10 µM, at most 9 µM, at most 8 µM, at most 7 µM, at most 6 µM, at most 5 µM, at most 4 µM, at most 3 µM, at most 2 µM, at most 1 µM, at most 0.5 µM, or at most 0.1 µM. Those of skill in the art will recognize that the concentration of streptavidin or biotinylated protein used may have any value within this range, for example, about 4.4 µM. Expressed in terms of the amount of streptavidin or biotinylated protein used for attachment, the amount may range from about 1 nanogram to about 1,000 nanograms, or more. In some embodiment, the amount of streptavidin or biotinylated protein used for attachment may be at least 1 nanogram, at least 10 nanograms, at least 25 nanograms, at least 75 nanograms, at least 100 nanograms, at least 200 nanograms, at least 300 nanograms, at least 400 nanograms, at least 500 nanograms, at least 600 nanograms, at least 700 nanograms, at least 800 nanograms, at least 900 nanograms, or at least 1,000 nanograms. In some embodiments, the amount of streptavidin or biotinylated protein used for attachment may be at most 1,000 nanograms, at most 900 nanograms, at most 800 nanograms, at most 700 nanograms, at most 600 nanograms, at most 500 nanograms, at most 400 nanograms, at most 300 nanograms, at most 200 nanograms, at most 100 nanograms, at most 75 nanograms, at most 50 nanograms, at most 25 nanograms, at most 10 nanograms, or at most 1 nanogram. Those of skill in the art will recognize that the amount of streptavidin or biotinylated protein used for attachment may have any value within this range, for example, about 275 nanograms. The incubation time used for attaching streptavidin or biotinylated protein may range from about 10 minutes to about 60 minutes, or longer. In some embodiments, the incubation time used for attaching streptavidin or biotinylated protein may be at least 10 minutes, at least 20 minutes, at least 30 minutes, at least 40 minutes, at least 50 minutes, or at least 60 minutes. In some embodiments, the incubation time used for attaching streptavidin or biotinylated protein may be at most 60 minutes, at most 50 minutes, at most 40 minutes, at most 30 minutes, at most 20 minutes, or at most 10 minutes. Those of skill in the art will recognize that the incubation time used for attaching streptavidin or biotinylated protein may have any value within this range, for example, about 34 minutes.

As yet another example, in embodiments of the disclosed methods where His-tagged proteins are immobilized to supported lipid bilayers using anchor lipid molecules comprising Ni-NTA (or other chelated metal ion) ligands, the mole percent of Ni-NTA-containing lipid molecule used to form the bilayer may be varied in order to control the surface density of Ni-NTA ligands available for binding. The concentration of Ni-NTA-containing lipid molecules may range from as little as 1 mole percent to as much as 90 mole percent, or more. In some embodiments, the concentration of Ni-NTA-containing lipid molecules in the supported lipid bilayer may be at least 1 mole percent, at least 2.5 mole percent, at least 5 mole percent, at least 10 mole percent, at least 20 mole percent, at least 30 mole percent, at least 40 mole percent, at least 50 mole percent, at least 60 mole percent, at least 70 mole percent, at least 80 mole percent, or at least 90 mole percent. In some embodiments, the concentration of Ni-NTA-containing lipid molecules in the supported lipid bilayer may be at most 90 mole percent, at most 80 mole percent, at most 70 mole percent, at most 60 mole percent, at most 50 mole percent, at most 40 mole percent, at most 30 mole percent, at most 20 mole percent, at most 10 mole percent, at most 5 mole percent, at most 2.5 mole percent, or at most 1 mole percent. Those of skill in the art will recognize that the concentration of Ni-NTA-containing lipid molecules in the supported lipid bilayer may have any value within this range, for example, about 4.5 mole percent. Alternatively, the concentration and/or incubation time used for attaching His-tagged proteins (or other His-tagged biological entities) to the Ni-NTA groups in the lipid bilayer may be varied. The concentration of His-tagged protein (or other His-tagged biological entities) used for attachment may range from about 0.1 µM to about 10 µM, or more. In some embodiments, the concentration of His-tagged proteins (or other His-tagged biological entities) used may be at least 0.1 µM, at least 0.5 µM, at least 1 µM, at least 2 µM, at least 3 µM, at least 4 µM, at least 5 µM, at least 6 µM, at least 7 µM, at least 8 µM, at least 9 µM, or at least 10 µm. In some embodiments, the concentration of His-tagged proteins (or other His-tagged biological entities) used may be at most 10 µM, at most 9 µM, at most 8 µM, at most 7 µM, at most 6 µM, at most 5 µM, at most 4 µM, at most 3 µM, at most 2 µM, at most 1 µM, at most 0.5 µM, or at most 0.1 µM. Those of skill in the art will recognize that the concentration of u His-tagged proteins (or other His-tagged biological entities) used may have any value within this range, for example, about 7.5 µM. Expressed in terms of the amount of His-tagged proteins (or other His-tagged biological entities) used for attachment, the amount may range from about 1 nanogram to about 1,000 nanograms, or more. In some embodiment, the amount of His-tagged proteins (or other His-tagged biological entities) used for attachment may be at least 1 nanogram, at least 10 nanograms, at least 25 nanograms, at least 75 nanograms, at least 100 nanograms, at least 200 nanograms, at least 300 nanograms, at least 400 nanograms, at least 500 nanograms, at least 600 nanograms, at least 700 nanograms, at least 800 nanograms, at least 900 nanograms, or at least 1,000 nanograms. In some embodiments, the amount of His-tagged proteins (or other His-tagged biological entities) used for attachment may be at most 1,000 nanograms, at most 900 nanograms, at most 800 nanograms, at most 700 nanograms, at most 600 nanograms, at most 500 nanograms, at most 400 nanograms, at most 300 nanograms, at most 200 nanograms, at most 100 nanograms, at most 75 nanograms, at most 50 nanograms, at most 25 nanograms, at most 10 nanograms, or at most 1 nanogram. Those of skill in the art will recognize that the amount of His-tagged proteins (or other His-tagged biological entities) used for attachment may have any value within this range, for example, about 425 nanograms. The incubation time used for attaching His-tagged proteins (or other His-tagged biological entities) may range from about 10 minutes to about 60 minutes, or longer. In some embodiments, the incubation time used for attaching His-tagged proteins (or other His-tagged biological entities) may be at least 10 minutes, at least 20 minutes, at least 30 minutes, at least 40 minutes, at least 50 minutes, or at least 60 minutes. In some embodiments, the incubation time used for attaching His-tagged proteins (or other His-tagged biological entities) may be at most 60 minutes, at most 50 minutes, at most 40 minutes, at most 30 minutes, at most 20 minutes, or at most 10 minutes. Those of skill in the art will recognize that the incubation time used for attaching His-tagged proteins (or other His-tagged biological entities) may have any value within this range, for example, about 48 minutes.

Variation of SHG Signal with Surface Density of Immobilized Biological Entities

Surprisingly, the increase in SHG signal observed for increasing surface densities of immobilized, labeled biological molecules on the optical interface exceeded expectations based on equation (1) under some conditions. As illustrated in Example 1 below, an approximately 3.3-fold increase in the number of immobilized protein molecules (assuming saturation of the available binding sites on the surface by the labeled protein molecules) resulted in a dramatic increase in SHG signal intensity, i.e. a much larger increase than expected from the squared power law dependence of SHG signal on the number or surface density of immobilized proteins alone. This result is borne out by the data presented in Example 2 as well.

Further refinement of the protocols used for immobilization of labeled proteins or other biological entities may yield further increases in the SHG signal intensity (or other nonlinear optical signal) observed for increased surface density of the immobilized component. In some embodiments, a 2-fold increase of the concentration of anchor molecule used for immobilization (or the number or surface density of the immobilized biological entity) may yield at least a 5× increase, at least a 10× increase, at least a 15× increase, or at least a 20× increase in the nonlinear optical signal detected. In some embodiments, a 2-fold increase of the concentration of anchor molecule used for immobilization (or the number or surface density of the immobilized biological entity) may yield at most a 20× increase, at most a 15× increase, at most a 10× increase, or at most a 5× increase in the nonlinear optical signal detected.

Devices and Kits

It will be apparent to those skilled in the art that the methods for immobilizing biological entities disclosed herein may be used in producing devices and kits for enabling non-linear optical measurements of conformation, orientation, or changes in conformation or orientation in biological molecules and other biological entities.

As one non-limiting example of devices disclosed herein, consider a device comprising: (a) a substrate, wherein the substrate further comprises a supported lipid bilayer; and (b) a biological entity, wherein the biological entity comprises an non-linear active label and is tethered to the supported lipid bilayer using a pair of affinity tags, and wherein one of the affinity tags is attached to the supported lipid bilayer and the other affinity tag is attached to the biological entity; and wherein the device is capable of producing a non-linear optical signal when exposed to excitation light.

A device of this type may be configured in a variety of different ways, for example, the substrate may be fabricated from a material selected from the group including, but not limited to, glass, fused-silica, a polymer, or any combination thereof. A variety of affinity tags may be used, including Ni-NTA (or other chelated metal ions) and poly-histidine tags, or biotin and streptavidin (or avidin, or neutravidin). In devices comprising the use of poly-histidine tags, the poly-histidine tag may be attached to the N-terminus of a protein or to the C-terminus of a protein, or at any other position in the protein's sequence that maintains protein function and also provides suitable exposure on the protein surface so that the poly-histidine tag is able to interact with Ni-NTA or other chelated metal ion ligands. As will be apparent to those skilled in the art, poly-histidine tags may comprise any suitable number of histidine residues, for example, something between 4 and 12 histidine residues, or about 9 histidine residues, or about 6 histidine residues. Another example of a chelated metal ion that may be used as a suitable ligand for binding poly-histidine tags is Co-CMA. Examples of non-linear optical signals that may be produced by the device when exposed to excitation light include second harmonic light, sum frequency light, and difference frequency light. A variety of different biological entities may be utilized in such devices including, but not limited to, cells, proteins, peptides, receptors, enzymes, antibodies, DNA, RNA, biological molecules, oligonucleotides, small molecules, synthetic molecules, carbohydrates, or any combination thereof.

As one non-limiting example of kits disclosed herein, consider a kit comprising (a) a substrate; (b) a lipid suspension, wherein the lipid suspension is capable of forming a supported lipid bilayer on a surface of the substrate; and (c) affinity tagged reagents for tethering biological entities to the supported lipid bilayer.

Kits may be configured in a variety of different ways, for example, the device substrate may be fabricated from a material selected from the group including, but not limited to, glass, fused-silica, a polymer, or any combination thereof. A variety of affinity tagged reagents could be used in the kit, including Ni-NTA (or other chelated metal ion ligand) and poly-histidine tagged reagents, or biotinylated reagents along with streptavidin (or avidin, or neutravidin). The lipid suspension used for formation of supported lipid bilayers may include a variety of different phospholipids or other suitable lipids, for example, in some embodiments, the kits may include 1,2-dioleoyl-sn-glycero-3-phosphocholine and/or 1,2-dioleoyl-sn-glycero-3-([N-(5-amino-1-carboxy-pentyl)iminodiacetic acid)succinyl] (nickel salt). It will be apparent to those of skill in the art that many other lipids and affinity tagged reagents may be used in kits of the present disclosure.

Example 1—Ni-NTA Immobilization

The objective of this study was to demonstrate the use of His-tag chemistry for immobilizing labeled proteins (i.e. labeled with an SHG-active label) to substrate surfaces comprising the optical interface used in SHG measurements.

Figure 3:
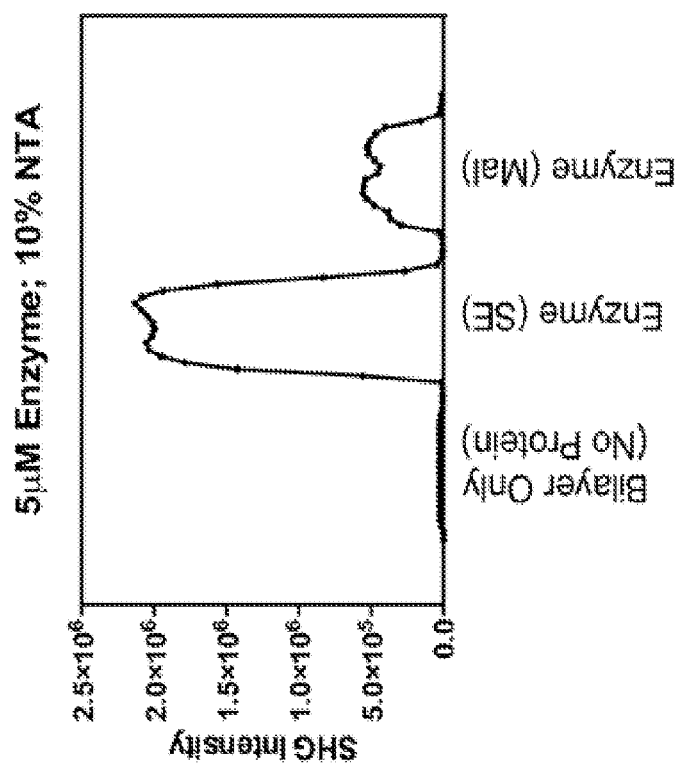
FIG. 3 shows a plot of SHG signal intensity for a supported lipid bilayer only, and a supported lipid bilayer having tethered dihydrofolate reductase (DHFR) enzyme labeled with PyMPO-succinimidyl ester (SE) or tethered DHFR enzyme labeled with PyMPO-maleimide (Mal). 5 µM enzyme labeled with either PyMPO-maleimide or PyMPO-succinimidyl ester was incubated with a bilayer surface containing 10% Ni-NTA. Each protein was incubated for 60 minutes at room temperature in assay buffer containing 50 mM NaPO4 pH 7.0.

For the data shown in FIG. 3, 5 µM DHFR enzyme labeled with either PyMPO-maleimide (Mal) or PyMPO-succinimidyl ester (SE) was incubated on a bilayer surface containing 10% Ni-NTA. Each protein was incubated for 60 minutes at room temperature in assay buffer containing 50mM NaPO4 pH 7.0. Unbound protein was removed by washing with assay buffer. The slide was then placed on an SHG instrument and each sample was scanned for SHG intensity. A well with no protein added was used as a control to establish the baseline SHG signal intensity for each well containing labeled protein.

Figure 4:
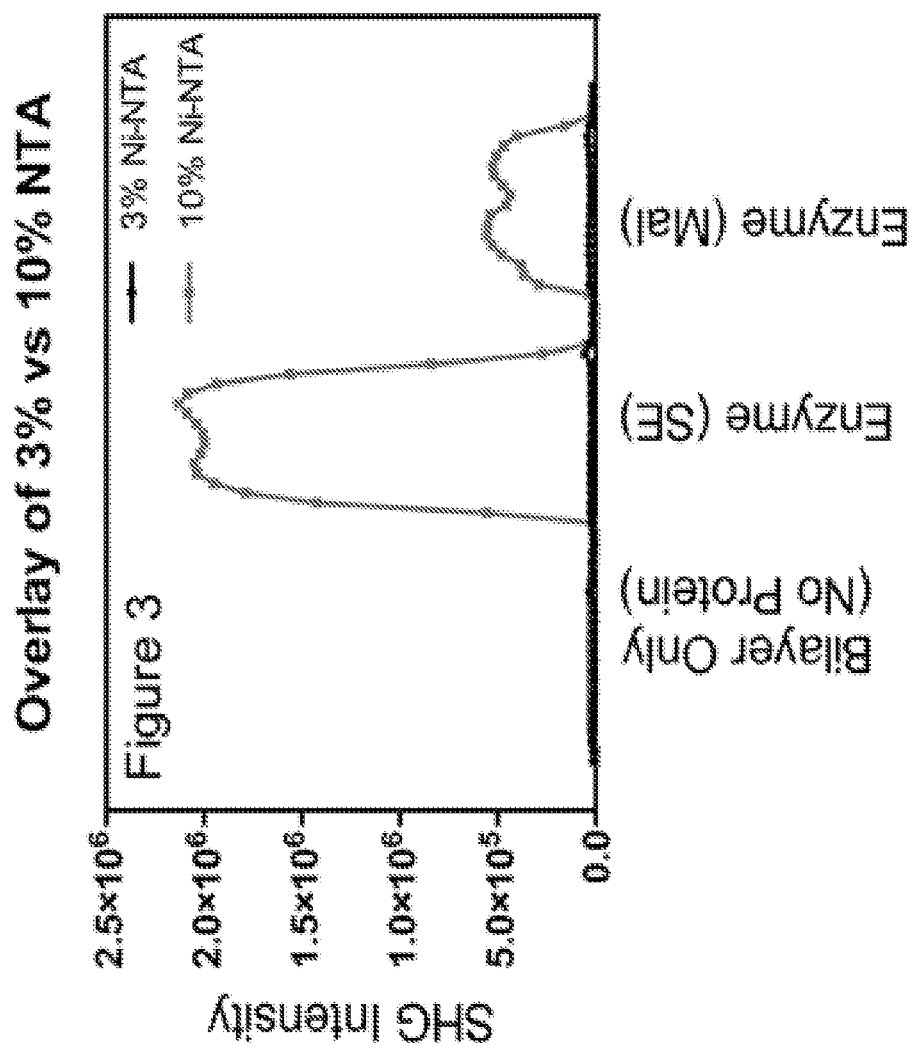
FIG. 4 shows an overlay of 3% and 10% Ni-NTA data to show the relative SHG intensity produced by each protein on the respective surface. The combination of slightly altered incubation conditions and/or increased Ni-NTA percentage provides at least an order of magnitude improvement in the SHG signal for the labeled DHFR enzyme tested here.

FIG. 4 is an overlay of SHG data acquired using labeled protein bound to a lipid bilayer comprising 3% Ni-NTA (under slightly different incubation conditions) and that for the 10% Ni-NTA data to show the relative SHG intensity produced by each labeled protein on their respective surfaces. The 10% NTA surfaces provided more than an order of magnitude improvement in the SHG signal for the labeled enzyme tested here.

Example 2—Ni-NTA Immobilization

Protein labeling protocol: Stock His-tagged maltose binding protein (MBP) (1 mL at nominal 0.5 mg/mL) was buffer exchanged from 20 mM Tris-HCL pH 8.0, 0.1 M NaCl, 10% Glycerol into 0.1 M Na phosphate, pH 7.5 by passing over two of the 2 mL Zeba™ Spin Desalting Columns (Thermo Scientific) equilibrated per the manufacturer's instructions. Concentration and volume of the buffer exchanged material were determined by measuring absorbance on a NanoDrop Spectrophotometer (Thermo Scientific). PyMPO-NHS was weighed out and dissolved to 2 mM in dry DMSO. PyMPO-NHS was added to the buffer exchanged MBP at 3.5:1 mole equivalents. The conjugation reaction was allowed to proceed in the dark at room temp, stirring gently, for 15 minutes. The reaction was terminated by buffer exchange back into the MBP storage buffer (20 mM Tris-HCL pH 8.0, 0.1 M NaCl, 10% Glycerol) over a fresh pair of Zeba™ Spin Desalting Columns. The resultant conjugate was centrifuged at 16K×g for 20 minutes at 4° C., and volume, concentration and degree of labeling was determined for the supernatant by measuring absorbance at 280 nm and 410 nm on the NanoDrop. Aliquots of the conjugate were snap frozen in liquid $N_2$ and stored at −80° C. The resulting conjugate concentration was 9.74×10−6 M with a degree of labeling (DoL) of 2.4.

Slide preparation: A glass slide was cleaned by Piranha treatment (heating at 100° C. in 30% H2O2/70% con H2SO4 for 30 minutes). The slide was washed extensively in $diH_2O$, dried with $N_2$ gas, and a well-forming gasket was affixed.

Bilayer preparation: Small unilamellar lipid vesicle (SUV) solutions consisting of 3% DGS-NTA, Ni salt, or 10% DGS-NTA, Ni salt, at a stock concentration of 0.5 mg/mL were diluted to 0.1 mg/mL in 25 mM Tris-HCl, ph 7.2, 150 mM NaCl. 10 uL aliquots were then added to wells, and incubated at room temperature for 60 minutes to allow bilayer formation. Excess SUV were washed out with 10×20 uL of either DHFR Assay buffer (50mM Na phosphate pH 7.0, 100 uM NADPH) or MBP Assay buffer (20 mM Tris-HCl, pH 8.0, 150 mM NaCl, 0.05% Tween-20, 1 mM DTT), leaving 10 uL behind at the end of the wash step.

Tethering of proteins: MBP and DHFR conjugates were diluted to 5 uM in their respective assay buffers, and 10 uL was added to the appropriate wells, thereby resulting in a concentration of 2.5 uM in the wells. 10 uL of assay buffer was added to the bilayer-only controls. Protein tethering was allowed to proceed for 1 hour at room temperature. During the tethering incubation, solutions of 2 mM lactose and 2 mM maltose were made up in MBP assay buffer. At the end of the tethering incubation, excess protein was washed out with 10×20 uL each of the appropriate assay buffer, leaving a volume of 10 uL in the wells, and the slide was mounted on the Artemis SHG System for scanning.

Scanning: The entire slide was line scanned to gather SHG data for determining the relative tethering efficiency of 3% vs 10% Ni-NTA surfaces. Well positions for 10% Ni-NTA tethered MBP were recorded and used to set up the MBP kinetic reads (3 wells total).

The chopper was placed 'in line' and operated at 120 Hz. The first objective was to show maltose-induced conformational change, using 10 uL buffer and 10 uL lactose injections as negative controls. For each injection, a volume of 10 uL was injected to give a total of 20 uL/well, and the volume was mixed by repetitively drawing up 10 uL volumes (4-5 times), then withdrawing 10 uL of liquid to leave 10 uL in the well. This same routine was followed for the maltose injection, but at the end, 10 uL was not removed, leaving 20 uL in the well. The assay was successful in showing that MBP only responded to maltose, not to lactose or buffer negative controls, but SHG signal appeared to be dropping with exposure time.

To differentiate dissociation of protein from photobleaching, the second MBP well was exposed for a few seconds (chopper in), then the beam was blocked, and the cycle was repeated to yield 7 short exposures over approximately 320 seconds. The signal appeared to drop even when the beam was blocked, indicating that some protein may be dissociating from the surface.

The conformation change evaluation was repeated, and again the MBP only responded to addition of maltose, not to the lactose or buffer negative controls. It also appeared that the slope of the line for the post-maltose injection was steeper than the pre-injection part of the trace.

The conformational change evaluation was again repeated using the last well. A few seconds after adding maltose, the beam was blocked for ~60 seconds before unblocking again to see if the signal continued to drop, which it appeared to do. The observed signal drop is most likely a combination of dissociation and photobleaching. It is not clear if the rate increased after conformational change was induced by maltose.

Figure 5:
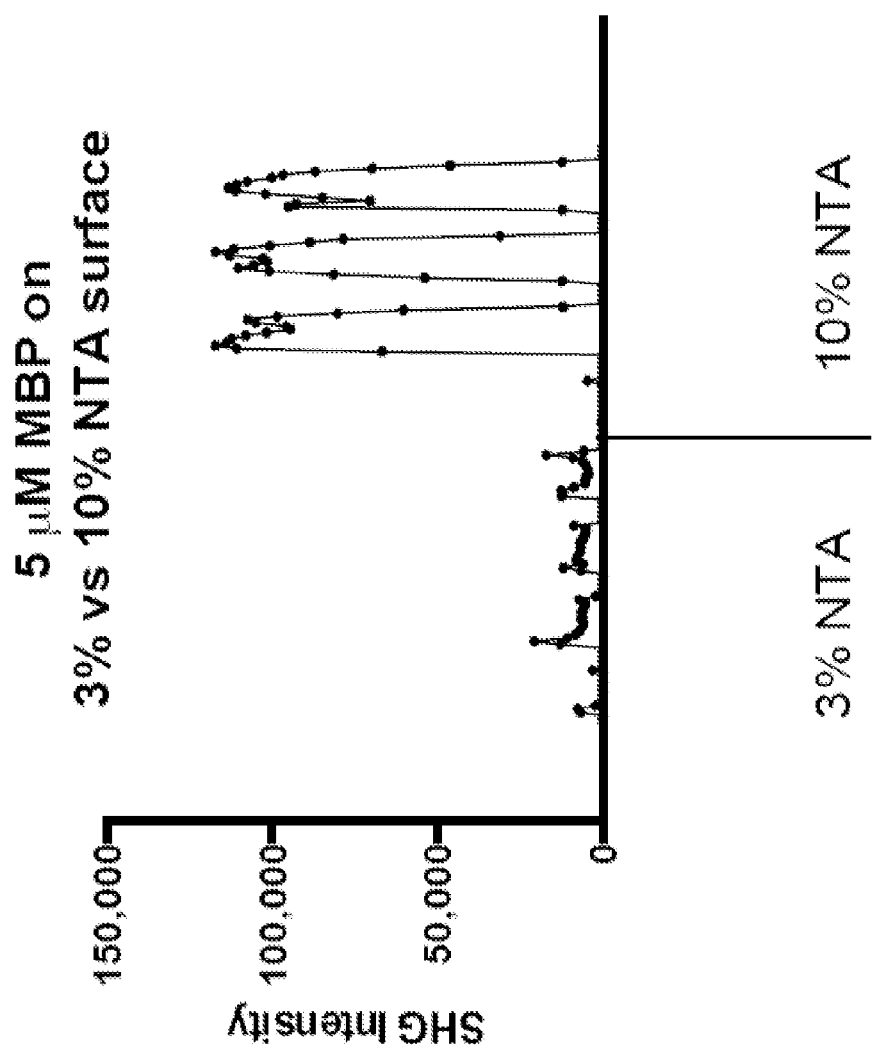
FIG. 5 shows a plot of SHG signal intensity data for PyMPO-labeled, His-tagged maltose binding protein (MBP) tethered to supported lipid bilayers doped with either 3% Ni-NTA-DGS or 10% Ni-NTA-DGS. Dramatic improvement in SHG signal intensity was observed for supported lipid bilayer prepared using a higher Ni-NTA concentration.

FIG. 5 shows a plot of SHG signal intensity data for PyMPO-labeled, His-tagged maltose binding protein (MBP) tethered to supported lipid bilayers doped with either 3% Ni-NTA-DGS or 10% Ni-NTA-DGS as described above. Despite some evidence for time-dependent changes in signal that may be due to photobleaching and/or protein dissociation over time, dramatic improvement in SHG signal intensity was observed for His-tagged, PyMPO-labeled protein tethered to supported lipid bilayers prepared using the higher Ni-NTA concentration.

Example 3—Protein Conformational Changes Detected & Resolved Site-Specifically

Background: In order to validate SHG as a broadly applicable biophysical technique to investigate protein structural motion, three model proteins were examined for studying ligand-induced conformational change: calmodulin (CaM), maltose binding protein (MBP), and *Escherichia coli* (*E. coli*) dihydrofolate reductase (DHFR).

MBP is a soluble, well-behaved protein in which the relationship between ligand binding, function, and conformational change has been extensively investigated by X-ray crystallography, NMR, and other biophysical techniques [8-15]. MBP belongs to a class known as periplasmic-binding proteins which are responsible for efficient uptake and catabolism of maltodextrins. Periplasmic-binding proteins share a two-domain structure linked by a flexible β-strand and are known to undergo large-scale motion from an open to a closed form upon binding maltose [16]. The transition from the open to closed form of MBP has also been exploited as a platform for developing biosensors for specific target compounds [17, 18].

CaM is a messenger protein that transduces calcium-generated signals by binding calcium ions [19]. CaM is implicated in numerous biological processes. The structural transition of CaM upon calcium ion binding has been extensively characterized by biochemical and biophysical techniques [20-24]. Calcium-free CaM adopts an extended, dumbbell structure with two similar lobes, each containing two calcium ion-binding sites. Binding of calcium ions changes the relative orientation of the helices flanking the calcium-binding loops, exposing a hydrophobic surface region that serves as a binding site for target proteins. Upon binding of a target protein, the two lobes of CaM collapse at the central helix to fold around the target peptide.

DHFR is a popular enzyme model for studying the relationship between conformational change and catalysis [25-27]. In cells, DHFR catalyzes the reduction of dihydrofolic acid to tetrahydrofolic acid with NADPH as an electron donor [28]. Tetrahydrofolate serves as cofactor in many reactions and is essential for purine and thymidylate biosynthesis, and thus cell growth, making DHFR a target for anticancer and antibacterial drugs [29]. During the catalytic cycle, DHFR converts between the closed and occluded forms of the protein which involves large conformational changes in the Met20 loop [30, 31]. In the closed form, the Met20 loop protects the active site from the solvent by packing against the nicotinamide ring of NADPH, bringing it into close proximity to dihydrofolic acid. In the occluded form, the Met20 loop projects into the active site and sterically blocks the nicotinamide ring. The transition from the occluded to closed state is associated with the rate-determining step in the catalytic cycle [27].

In the work presented here, we demonstrate a broadly applicable method based on second-harmonic generation (SHG) to study protein conformational changes upon ligand binding, in real time and under physiological conditions. We demonstrate that tethering of proteins to a biomimetic lipid membrane using immobilized metal affinity chemistry allows for facile capture of labeled protein molecules that also retain their function as shown by an ability to undergo well-characterized conformational changes. We demonstrate that different conformational changes induced by binding different ligands to the same labeled protein produce different responses by SHG. We also validate our SHG findings by identifying the labeled sites using mass spectrometry (MS) and correlating the changes we observe with the motion at these sites upon ligand binding as seen in the x-ray crystal structures. The advantages of SHG technique on lipid bilayer are discussed within. This work was recently published in Moree, et al. (2015), "Protein Conformational Changes Are Detected and Resolved Site Specifically by Second-Harmonic Generation", Biophys. J. 109:806-815.

Results: Characterization of protein attachment to the supported lipid bilayer. Both CaM and MBP have previously been examined for structural transitions upon ligand binding using SHG [32, 33]. However, in those experiments protein immobilization on the surface was accomplished using aldehyde-derivatized glass slides to covalently couple the protein via amine-containing residues to the surface. While tethering the protein directly to the slide achieves the noncentrosymmetric distribution required for SHG, this method of attachment is far from ideal as proteins immobilized in this manner have been shown to unfold or lose secondary structure [34, 35]. Because the direct attachment of protein to derivatized glass surfaces very often does not result in tethered and functional protein, we developed a supported lipid bilayer (SLB) interface as an attachment platform for SHG. SLBs are biomimetic and they have been used extensively in many biochemical and cell biology experiments with minimal impact on protein structure and function [36, 37].

Figure 6A:
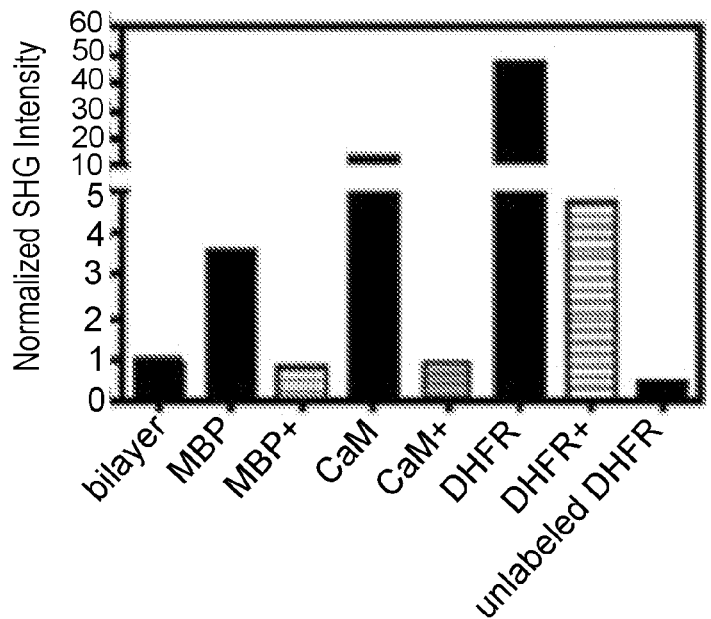
FIG. 6A illustrates characterization of protein immobilization on the bilayer surface. The bar graph shows the intensity of the SHG signal for the model proteins, with and without imidazole, and for unlabeled protein compared to bilayer. The + denotes the presence of 350 mM imidazole.

We began by characterizing the attachment of the proteins to our SLB surface. The SLB surface we employed has integrated immobilized metal affinity (Ni-NTA) chemistry to specifically tether the proteins to the bilayer in an oriented manner via a poly-histidine tag at the N- or C-terminus. To test the specificity of this interaction, each protein was incubated on the bilayer in the presence or absence of imidazole, a competitive inhibitor of His-tagged protein binding. As can be seen in FIG. 6A, incubation of the SH-functionalized proteins in the absence of imidazole results in a large increase in the SHG signal compared to the controls (addition of the unlabeled proteins or just the bilayer alone). When labeled protein is incubated in the presence of imidazole, SHG signal levels are reduced to less than 10% of the original signal or to background levels, i.e. to those of bilayer alone. Taken together, these results show that the SHG signal observed arises specifically from the dye-labeled protein bound via the His-tag-Ni-NTA linkage.

Figure 6B:
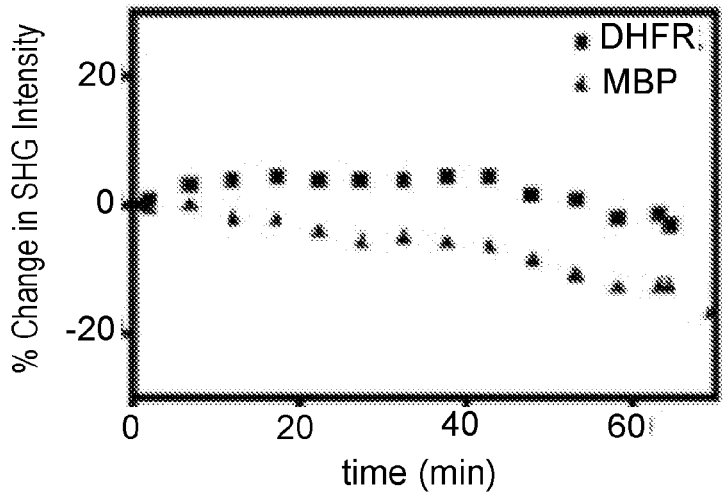
FIG. 6B shows a plot of SHG signal monitored as a function of time after wash-out of excess protein from the bilayer surface.

Next, we investigated the stability of the protein tethered to the SLB surface. Although the poly-histidine tag allows the protein to be captured and oriented in a specific manner on the SLB surface, the affinity of the 6x-His tag for Ni-NTA is only in the high nanomolar to low micromolar range (0.1-1 µM) [38]. Given this range of affinities, we wanted to characterize the kinetics of protein loss from the SLB surface to the bulk solution after washout of the unbound protein fraction, as loss of protein due to unbinding from the surface could impact the measured change in SHG intensity over the time-course of our experiments. Protein was incubated overnight at 4° C., as it has been reported that the stability of poly-histidine tagged proteins on bilayers is greatly increased by longer incubation period [39]. Following washout of unbound protein, the SHG signal for each protein was monitored over the course of ~1 hour. FIG. 6B shows that after washout the SHG signal is nearly constant over one hour, with losses of 3% observed for DHFR and 16% for MBP, demonstrating minimal dissociation of protein from the surface over this time frame. The stability of the protein attachment to the bilayer provides confidence that signal changes observed during an experiment, which typically occur over seconds to a few minutes, are the result of conformational change and not protein dissociation from the surface. The stability of our system also enables the monitoring of relatively slow processes on the order of tens of minutes.

Figure 6C:
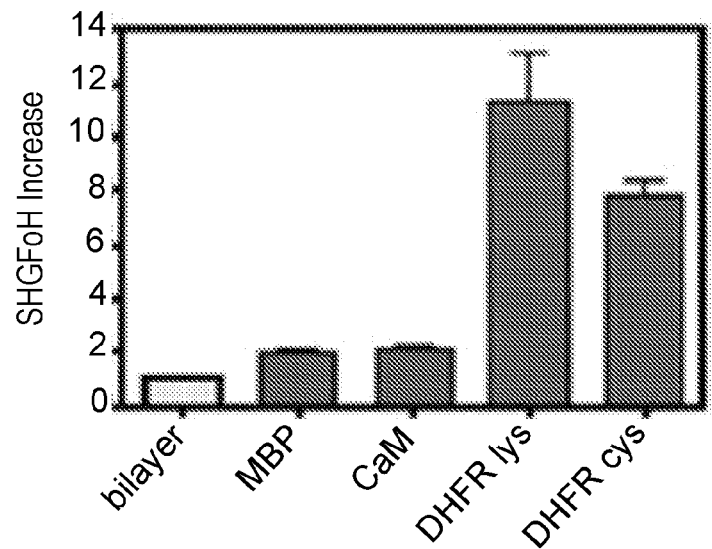
FIG. 6C shows a bar graph of the intensity of the SHG signal for incubation of 100 ng of each of the model proteins on the bilayer (N=3).

To further characterize our system, we explored the amount of protein required for producing reliable SHG signals on the bilayer surface. In these experiments, 100 ng of each of the model proteins was incubated on the bilayer for 1 hour, followed by buffer washout of excess protein. For each protein, signal of at least two-fold over background is observed (FIG. 6C). Finally, we measured the amount of the lysine-labeled MBP and DHFR proteins tethered to the membrane after washout with buffer. In order to do so, we tethered the proteins to the SLB, washed out the unbound protein with buffer, and then solubilized both the protein and the bilayer with detergent (Supplementary section). The SHG label is also fluorescent and its signal intensity was measured by fluorimetry and compared to a standard curve of the same labeled proteins. At the incubation concentrations in the experiments described here, lysine-labeled MBP (pH 8.3 conjugation) and DHFR are tethered to the bilayer surface at densities of $4.9\pm0.7\times10^{12}$ molecules/cm$^2$ and $2.8\pm0.1\times10^{12}$ molecules/cm$^2$, respectively. Taken together, the data characterizing our SLB surface demonstrate that SHG-labeled, poly-histidine tagged proteins are specifically and stably attached to the bilayer surface via metal chelation, that an SHG signal over background can be generated from bulk incubation of as little as 100 ng of labeled protein, and that the measured SHG signals are generated by a monolayer or less of molecules given the dimensions of the proteins and their theoretical close-packed densities.

Figure 7A:
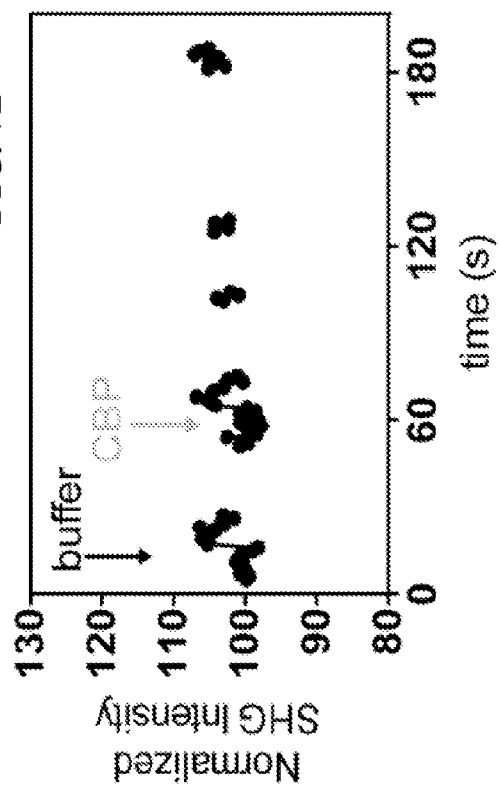
FIG. 7A shows a representative SHG time course for addition of calcium binding peptide (CBP) to calmodulin immobilized on an optical interface in the presence of calcium ions. The arrows indicate the time of addition of the indicated compounds.
Figure 7B:
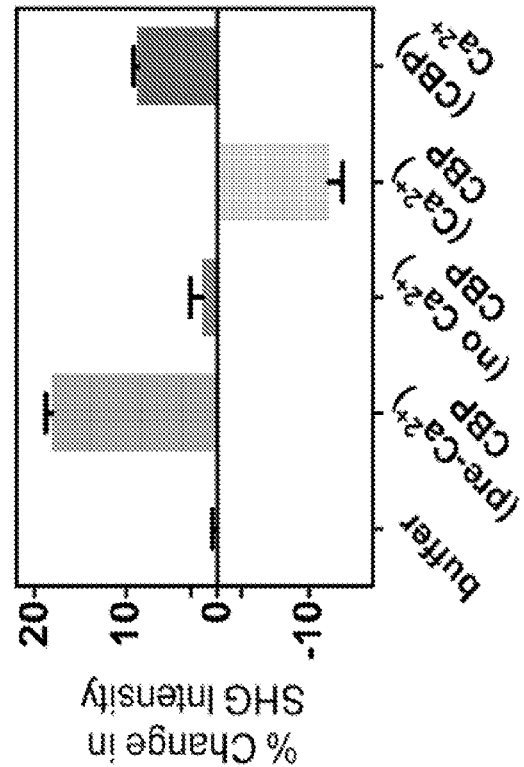
FIG. 7B shows a representative SHG time course for addition of calcium binding peptide to immobilized calmodulin in the absence of calcium ions.
Figure 7C:
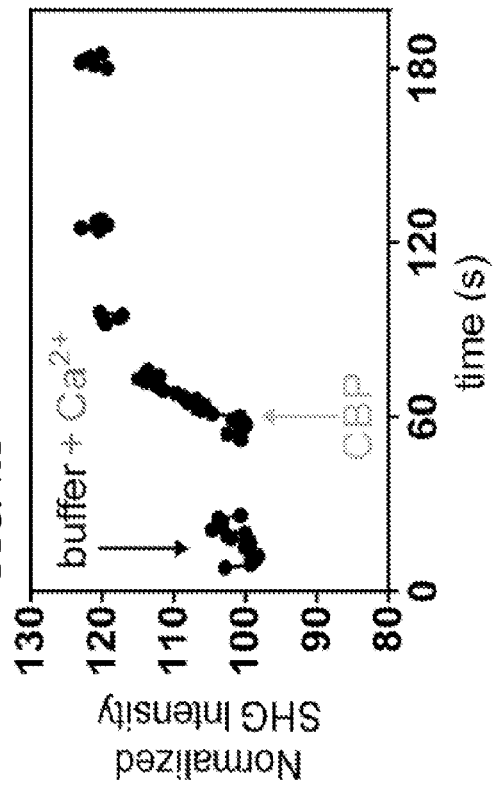
FIG. 7C shows a representative SHG time course for addition of calcium ions followed by addition of calcium binding peptide to immobilized calmodulin.
Figure 7D:
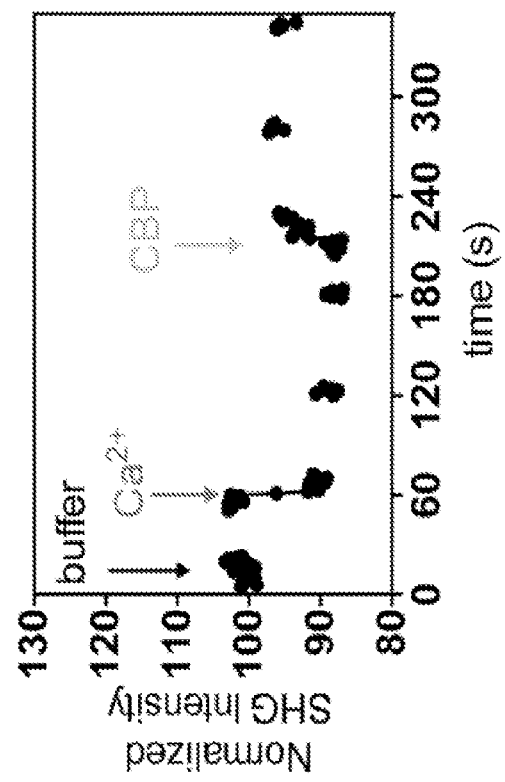
FIG. 7D shows a plot of percent changes in SHG signal observed for addition of calcium and CBP; dotted lines represent ±3σ from the mean of the buffer shifts.

MBP and CaM Proteins: To explore the ability of our SHG bilayer system to detect and measure conformational changes of a protein, we began by testing the system on CaM and MBP, two proteins previously studied by SHG [32, 33]. First, we tethered labeled CaM to the SLB surface and monitored the change in SHG intensity upon addition of the calmodulin binding peptide (CBP) in the presence or absence of calcium-containing buffers. As seen in FIG. 7A, the addition of 2 µM CBP in the presence of a calcium-containing buffer resulted in a positive change in SHG signal of M=18.1%, (N=3, SEM±0.6) whereas buffer injection resulted in a signal change of M=0.1% (N=9, SEM±0.4). When calcium is omitted from the buffer, addition of the peptide alone results in M=3.1%, (N=3, SEM±1.6) change in SHG intensity, essentially no change (FIG. 7B). As calcium-free calmodulin does not adopt a conformation capable of binding to peptide, these results confirm that the change observed upon peptide addition in the presence of calcium is due to the conformational change induced by peptide binding. Next, we evaluated the effect of adding calcium ions. When buffer containing 1 mM CaCl$_2$ is injected into the system, a decrease in signal of M=−12.6% (N=3, SEM±1.4) resulted (FIG. 7C). Peptide was then added directly to these samples two minutes after calcium addition, producing a positive signal change of M=8.7% (N=3, SEM±0.4). The magnitude of signal changes for each of these experiments is shown in FIG. 7D. As the magnitude of the SHG signal is proportional to the net, average orientation of the dye label relative to the surface normal, the different magnitudes of SHG signal change upon binding CBP and calcium to unbound CaM confirm that these ligands bind to specific and different conformations of the protein. SHG signal changes can occur in either the positive or negative direction relative to baseline depending on whether the net, average orientation of the probe moves closer to or further away from the surface normal, respectively.

Figure 7E:
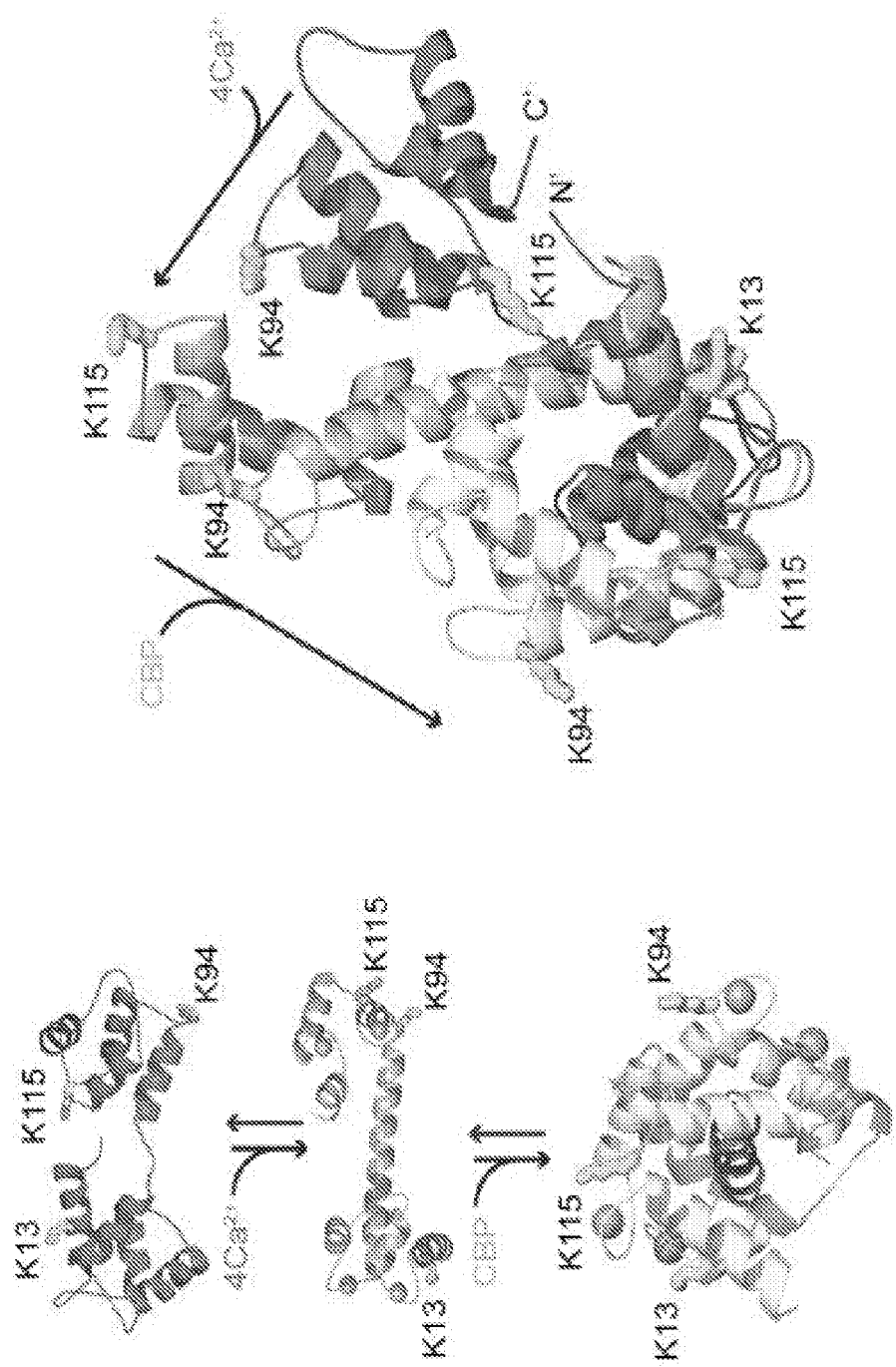
FIG. 7E shows the crystal structures of free calmodulin (red; pdb 1CFD), Ca-bound calmodulin (orange; pdb 1CLL), and Ca/CBP-bound calmodulin (yellow; pdb 1CDL) shown with the labeled lysine residues identified by mass spectrometry in green. Calcium ions are shown in blue and CBP is shown in purple.

We next sought to determine which residues were modified with our amine reactive dye. Mass spectrometry of labeled CaM revealed complete labeling at K115 and less than complete modification at K13 and K94. As the degree of labeling for CaM is 1.0 (dye:protein ratio), determined by measuring the UV-Vis spectrum, most of the signal is likely due to labeling at K115. As can be seen from the overlay of the crystal structures of the apo, $Ca^{2+}$-bound, and CBP-bound CaM in FIG. 7E, all three residues undergo large structural changes upon binding both calcium and CBP. Taken together, the data demonstrate the detection of conformational changes associated with both calcium and CBP binding to calmodulin using SHG. Moreover, the peptide- and $Ca^{2+}$-induced conformational changes are clearly different in both magnitude and directionality, illustrating SHG's ability to discriminate the different conformations the protein adopts upon binding different ligands.

Figure 8A:
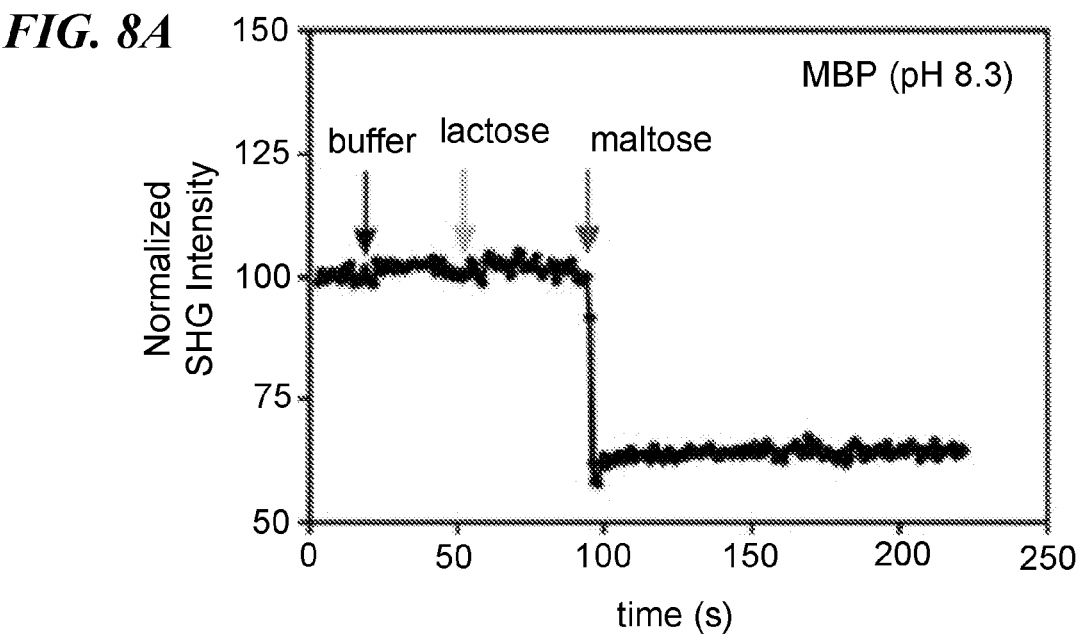
FIG. 8A shows a representative time course of SHG signal during compound addition to maltose binding protein (MBP) labeled at pH 8.3. The arrows denote the time of injection of buffer, lactose, and maltose.

We also performed a similar set of experiments with MBP. First, we monitored the SHG intensity of MBP labeled at pH 8.3 upon addition of buffer, lactose, or maltose. As can be seen in the real-time trace of the SHG signal, the addition of 2 mM maltose resulted in an instantaneous decrease of $M=-33.8\%$ ($N=4$, SEM±1.0), whereas the addition of either buffer or 2 mM lactose resulted in a negligible change of $M=0.12\%$ ($N=4$, SEM±0.61) or $M=0.44\%$ ($N=4$, SEM±0.79) respectively (FIG. 8A). The MBP system offers an excellent control in lactose, a stereoisomer of maltose that does not bind to MBP. Because the addition of both 2 mM lactose and buffer alone result in negligible changes in SHG intensity, the change in SHG intensity upon maltose addition is specific to ligand-induced conformational change upon binding.

Figure 8B:
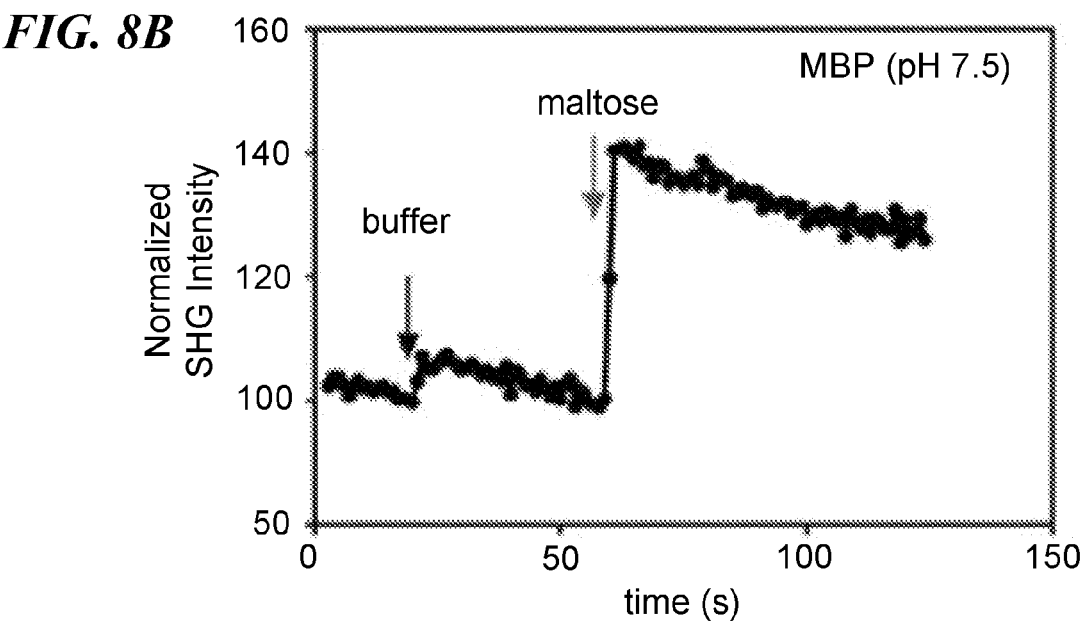
FIG. 8B shows a representative time course of SHG signal during compound addition to MBP labeled at pH 7.5. The arrows denote the time of injection of buffer and maltose.
Figure 8D:
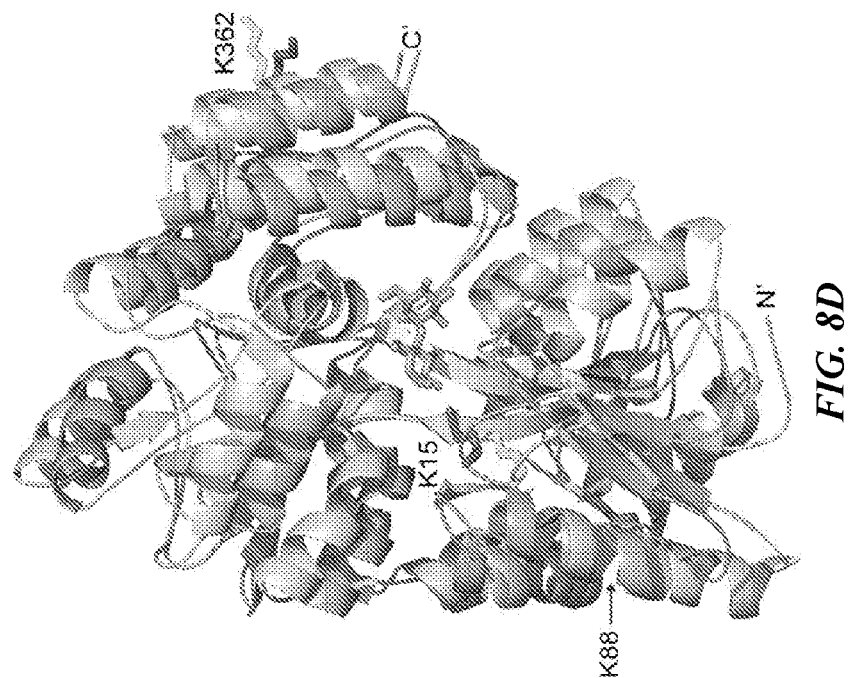
FIG. 8D shows an overlay of the crystal structures of MBP with maltose (blue; pdb 1ANF) and without maltose (orange; pdb 1JW4) bound. Maltose is shown in blue. Modified lysine residues identified by mass spectrometry are shown as sticks in purple on the unbound structure and in green on the bound structure. Many of the labeled lysines are in different conformations in the two crystal structures. For this comparison, the structures were aligned at their N-terminal domains. The His-tag and thus the site of immobilization of the protein is at the N-terminus.
Figure 8C:
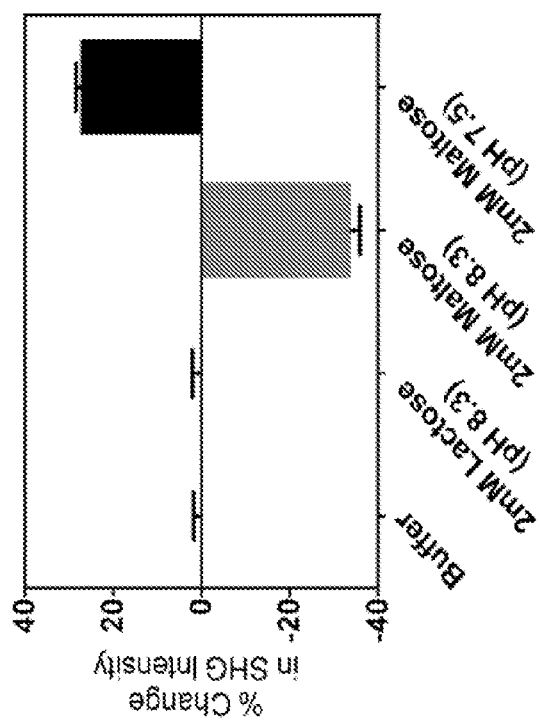
FIG. 8C shows a plot of the percentage change in SHG signal observed for addition of buffer, lactose, and maltose to MBP. The dotted lines represent ±3σ standard deviations from the average of the buffer shifts.

Mass spectrometry analysis of MBP revealed that it is heterogeneously labeled at nine lysine residues present in the sequence, although residues K15, K88, and K362 represent approximately 90% of the total population of modified peptides. The degree of labeling for MBP is 1.3, confirming that more than one residue is labeled. We aligned the crystal structures of the apo and maltose-bound MBP and compared the positions of the labeled residues in these two structures. As can be seen in FIG. 8D, the side chains of the labeled residues show significant orientational differences, providing further validation that the observed change in SHG intensity is the result of ligand-induced binding of maltose to MBP.

As MBP demonstrated a high degree of lysine modifications, we modified our labeling conditions to explore whether we could target specific lysines for labeling. Labeling MBP at pH 7.5 rather than pH 8.3 significantly increased the overall abundance of the K15 modification with a corresponding decrease in the modification at K88; 70% of the peptides detected by MS show labeling at K15 rather than K88. The converse trend, preference at K88 over K15, was observed when the experimental conditions changed to pH 8.3. The degree of labeling of the conjugate labeled at pH 7.5 is 1.3, which also suggests that the protein is primarily labeled at K15. This example shows that by varying the conditions of the conjugation reaction, one can bias the distribution of labeled lysines to favor one among multiple ones, by exploiting the differences in the residue's microenvironment and pKa, for example. Based on inspection of the crystal structures, we hypothesized that when MBP is primarily labeled at K15 rather than K88, this could alter the directionality of SHG signal change upon ligand addition relative to the reverse case, since K15 and K88 appear to rotate towards and away from the surface normal, respectively, assuming the protein is oriented with its N-terminus facing the bilayer. As can be seen in FIG. 8B, addition of 2 mM maltose to pH 7.5 labeled MBP results in an increase in the SHG intensity of $M=27.4\%$ ($N=3$, SEM±0.61). Consistent with previous results, the addition of lactose and buffer alone had no effect.

Figures 9A, 9B:
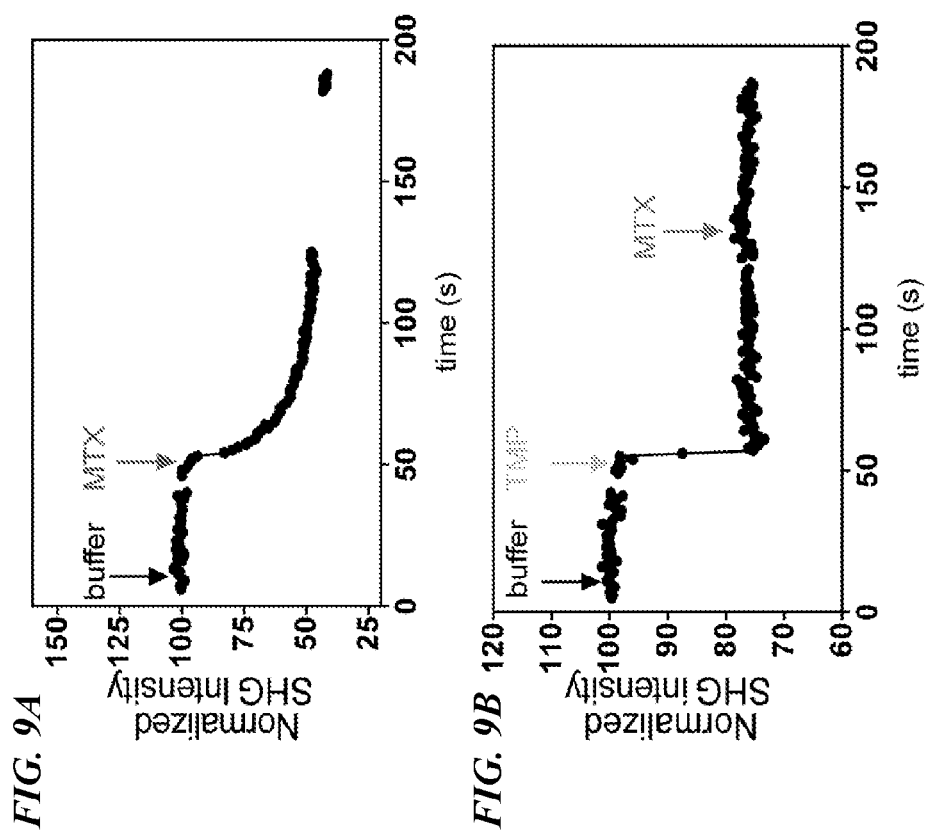
FIG. 9A shows a representative kinetic trace for methotrexate (MTX) addition to lysine-labeled dihydrofolate reducatase (DHFR). Arrows denote time of addition of buffer and MTX.
FIG. 9B shows a representative kinetic trace for a TMP-MTX competition experiment for lysine-labeled DHFR. Arrows denote time of addition of buffer, TMP, and MTX.
Figure 9D:
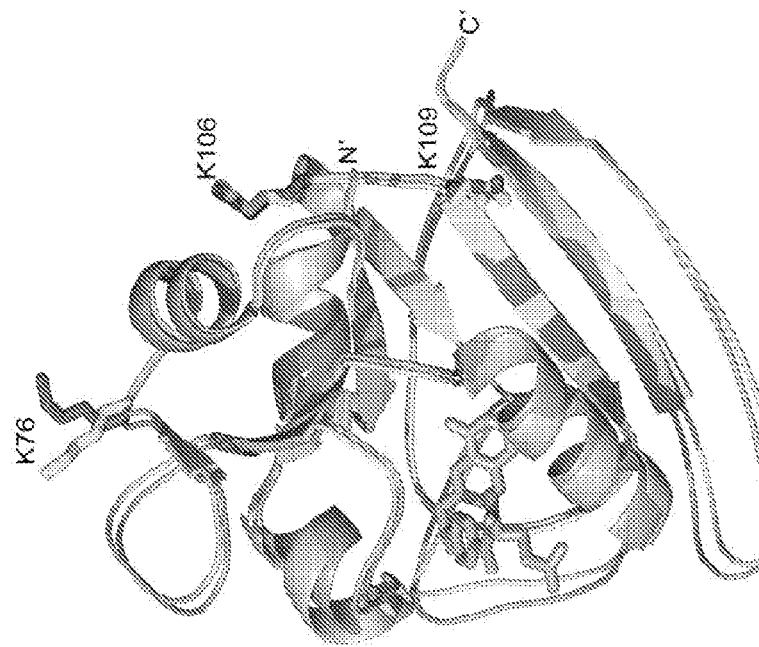
FIG. 9D shows the crystal structures of the DHFR holoenzyme with (blue; pdb 1RB3) and without (orange; pdb 1RX1) MTX bound. Labeled residues identified by mass spectrometry are shown as sticks in green for DHFR without MTX and in purple for DHFR bound to MTX. MTX is represented in blue.
Figure 9C:
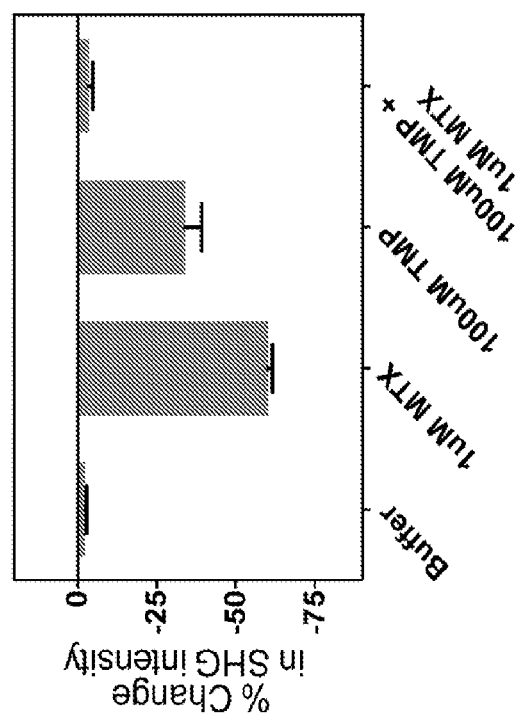
FIG. 9C shows a plot of the percent changes in SHG signal observed for buffer, MTX, and TMP addition to lysine-labeled DHFR.

Dihydrofolate reductase: As a final demonstration of the technique, we studied *E. coli* DHFR, a protein previously uncharacterized by SHG. In particular, we focused on the protein's response to two important pharmaceutical inhibitors: methotrexate (MTX) and trimethoprim (TMP)[29]. For these studies, we chose two approaches to label the protein: native lysine residues and an engineered, unique cysteine at residue 20. As seen in FIG. 9A, the addition of 1 μM MTX to the amine labeled DHFR resulted in a rapid decrease in SHG signal of $M=-60.2\%$ ($N=4$, SEM±1.26) compared to $M=-2.27\%$ ($N=8$, SEM±0.48) for the buffer control. As a control to show that the SHG signal change arises from the change in conformation upon the binding of MTX and not loss of protein from the surface, a competition experiment was carried out with the antibiotic TMP. Both MTX and TMP bind to the folate pocket on DHFR with high affinity, so addition of excess TMP should inhibit the change in SHG intensity upon MTX addition. We began by exploring whether TMP addition by itself would result in a conformational change in DHFR. As can be seen in FIG. 9B, the addition of 100 μM TMP resulted in a decrease in SHG intensity of $M=-33.9\%$ ($N=4$, SEM±5.31). Subsequent addition of 1 μM MTX resulted in a decrease of $M=-3.48\%$ ($N=4$, SEM±1.31) in SHG signal. This small change in SHG intensity is not significantly different than the buffer control, and the absence of signal change in this competition experiment is expected as both MTX and TMP compete for the same binding site. These results are summarized in FIG. 9C. MS analysis revealed that three residues, K76, K106, and K109, are modified by the amine-reactive SHG dye, with the modification at K76 being nearly complete. The degree of labeling of the amine-labeled DHFR conjugate is 1.1, suggesting that labeled K76 is the primary contributor to the observed signal. As seen in FIG. 9D in an overlay of the x-ray structures of the apo and MTX-bound DHFR holoenzyme there is relatively little motion at sites K106 and K109 but significant reorientation at site K76, corroborating our SHG measurements and the MS analysis.

Figures 10A, 10B:
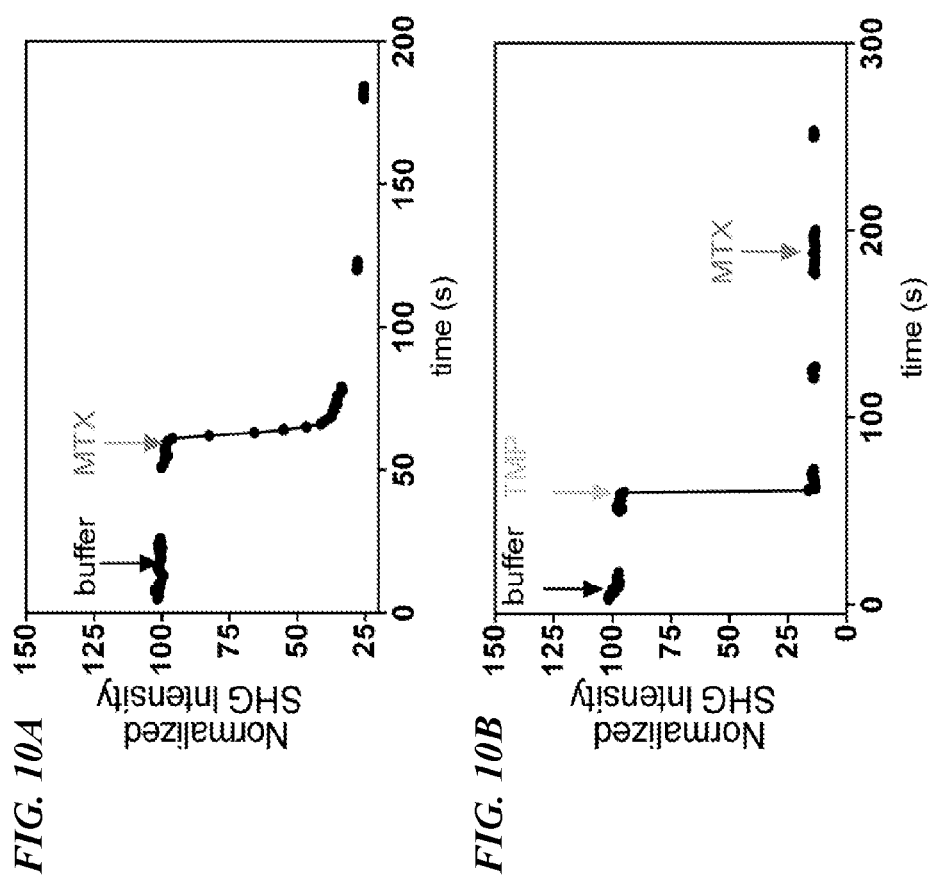
FIG. 10A shows a representative time course for MTX addition to cysteine-labeled DHFR.
FIG. 10B shows a representative kinetic trace for a TMP-MTX competition experiment for cysteine-labeled DHFR. Arrows denote time of addition of buffer, TMP, and MTX.
Figure 10D:
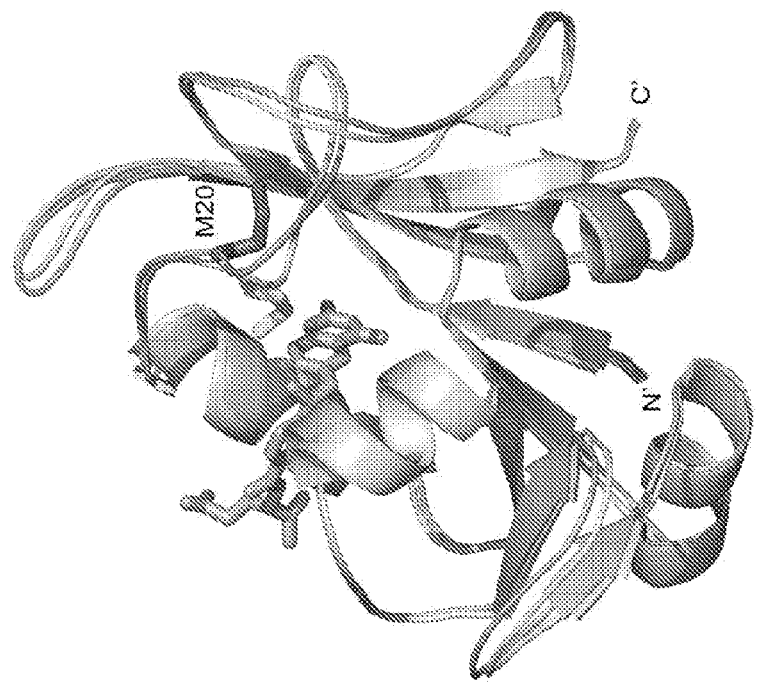
FIG. 10D shows the crystal structures of the DHFR holoenzyme with (blue; pdb 1RB3) and without (orange; pdb 1RX1) MTX bound with residue M20 shown in sticks in purple and green for the bound and unbound forms, respectively.
Figure 10C:
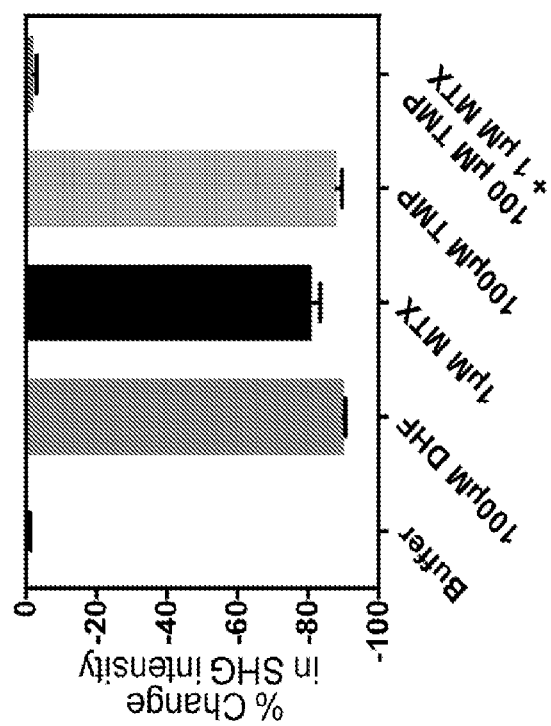
FIG. 10C shows a plot of the percentage change in SHG signal observed for buffer. MTX, and TMP addition to cysteine-labeled DHFR.

We also performed the same series of experiments on DHFR labeled specifically at a single-site engineered cysteine (M20C). Complete labeling of the cysteine residue was confirmed by mass spectrometry and the degree of labeling was 1.0 indicating that the labeling was site-specific. The ΔCys M20C construct maintained the wild-type enzymatic activity. As seen in FIG. 10A, the trends are similar to those seen with amine-labeled DHFR, although the magnitude of the observed change is different. Addition of MTX to cysteine-labeled DHFR on the bilayer resulted in a large change in the SHG intensity of $M=-75.6\%$ ($N=3$, SEM±1.18) compared to $M=-1.3\%$ ($N=4$, SEM±0.36) for buffer alone. Surprisingly, addition of TMP alone produces an even larger decrease in SHG intensity of $M=-84.7\%$ ($N=3$, SEM±0.57) and, as with amine-labeled DHFR, addition of 1 μM MTX in the presence of TMP resulted in an insignificant change in SHG intensity of $M=-1.9\%$ ($N=3$, SEM±1.02) (FIG. 10B), which can be rationalized by a relatively long residence time for TMP bound to DHFR {Carroll, 2012 #731}. These results are summarized in FIG. 10C.

Discussion: In the work described here, we demonstrate a broadly applicable and sensitive approach using SHG for detecting and resolving ligand-induced protein conformational changes using three different examples (CaM, MBP, and *E. coli* DHFR) proteins. This approach is based on using labeled proteins tethered to a supported lipid bilayer membrane. While most proteins are not intrinsically SH-active, proteins can be easily made so by standard amine- and thiol-reactive chemistries. We identified the labeled sites by mass spectrometry which, when combined with the available x-ray crystal structures, allowed us to inspect and confirm the structural motions that we observe by SHG to the motion observed at the modified residues in both the apo and bound structures for all three proteins.

In addition to providing direct evidence that the changes in SHG signal upon ligand binding result from motion at specific labeled residues, the MS analysis also provided indirect support for the orientation of the protein on the bilayer. Because the intensity of the SHG signal is directly dependent on the net, average orientation, the motion at the predominantly labeled residues can be inferred using the direction of the SHG signal change. For example, because the signal change in DHFR upon MTX addition decreased, we would expect that the K76 side chain would likely move away from the surface normal. The protein is tethered to the surface through the N-terminal poly-histidine tag and a large rotation of the K76 side chain away from the normal upon MTX addition is easily seen by inspection of the crystal structures. Only small motions are observed for the other modified residues. K106 and K109, suggesting that 1(76 contributes the majority of the motion we observe in amine-labeled DHFR samples.

We also probed the ability to target specific label sites by changing the pH of the conjugation reaction. At lower pH, the reduction of the K88 modification and subsequent enrichment of the K15 modification under these conditions resulted in the SHG response of MBP binding to maltose switching directionality, from a decrease in intensity relative to baseline for protein labeled at pH 8.3, to an increase in intensity for protein labeled at pH 7.5. As there are no other differences in the MS analysis between the conjugates labeled at these two pH's, this change in signal directionality is most likely due to the difference in the direction of movement between residues K15 and K88. The motion of the K88 residue upon MBP binding should cause a decrease in the SHG intensity with the protein tethered to the surface through the N-terminal poly-histidine tag, consistent with our observations (FIG. 8A). In contrast, with labeling predominantly at K15, we would expect an increase in SHG signal intensity, which is also consistent with the SHG results (FIG. 8B).

In addition to SHG's sensitivity, the technique offers a number of advantages over traditional methods for probing conformational change, one of which is the relative ease of performing experiments, as no a priori structural knowledge or engineering of the protein is required. The only requirements for sample preparation are the incorporation of a poly-histidine tag and the labeling of the target protein to make it SH-active. Multiple approaches can be taken to label proteins as we have demonstrated here, including labeling of lysines through amine-reactive chemistry, site specific labeling of native or engineered cysteines through thiol-reactive chemistry, and preferentially favoring specific residues by changing the conjugation conditions. Moreover, relatively small amounts of protein are required for each experiment (100's of ng).

A highly sensitive and generally applicable structural technique, like the SHG-based approach described here, can offer great utility in many facets of research, such as probing the functional and implications of structural rearrangement in a specific region of a protein due to ligand/drug/protein-protein interactions, assessing protein viability and stability, protein identification, optimization of formulation or effect of conditions, and mutational screening.

Using our approach, conformational changes that occur with binding or activity can readily be probed under a variety of experimental conditions such as different buffers, the presence of diverse ligands (e.g., peptides, cofactors), and across a wide range of protein or ligand concentrations. Furthermore, the approach offers the opportunity to draw correlations between the SHG structural measurements and data obtained from in vivo and pharmacological experiments. Here we show that *E. coli* DHFR generated different SHG signals when the enzyme was bound to two different pharmaceutical inhibitors. The SHG signals are very reproducible, and the difference between the two signals—and thus conformations—are easily distinguished. Thus the compounds produce distinct conformational changes upon binding to the protein. Knowing that the inhibition constant (Ki) between MTX and TMP is ~100 times (in favor of MTX), one might be able to establish a structure-activity relationship by evaluating the Ki value against the magnitude of the SHG signal change (e.g., from apo to bound forms). Once such an SAR is established, the SHG platform could offer a more convenient and efficient way to screen for potential drug candidate over the current activity and kinetic-based assays.

Another advantage of SHG is that there are no restrictions on the size or type of protein for study by SHG; large molecular weight proteins, protein complexes, and intrinsically disordered proteins can all be studied. Likewise, the technique is amenable to all types of ligands, from chemical fragments to small molecules to larger proteins for probing small molecule and protein-protein interactions since the technique does not depend on mass accumulation to produce a signal. The modest protein requirement for SHG measurements should allow large-scale structure-based screens not currently possible using other biophysical methods, which generally require much higher amounts of protein. In addition, the relatively low protein concentration requirement indicates that the technique lends itself well to study proteins that are not soluble or prone to aggregation at the higher concentrations required for techniques such as NMR and X-ray crystallography. Unlike both X-ray crystallography and NMR studies, which are time and resource-intensive, SHG requires as little as 100 ng of labeled protein per sample, making the technique amenable to high-throughput structural screening of compound libraries with relatively little protein consumption. The technique's attributes suggests a number of other applications as well, such as serial additions of different ligands in permuted order to determine mutual binding dependencies.

In summary, our data demonstrate that the SHG-based method presented here sensitively detects ligand-induced conformational changes that range in magnitude from the relatively small rotation of an amino acid side chain to the global motion of protein domains. The SHG measurements are strengthened by MS analysis to identify the labeled residues and corroborated by inspection of the crystal structures between the unbound and bound forms of the protein to confirm that motion occurs at the labeled sites. Enabled by the biomimetic SLBs as a two-dimensional platform for tethering and orienting proteins, SHG offers a straightforward means to provide new information about structure, function and activity on a broad range of proteins and under diverse conditions.

Methods—Lipids and SUV Preparation: 1,2-Dioleoyl-sn-glycero-3-phosphocholine (DOPC) and 1,2-dioleoyl-sn-glycero-3-([N-(5-amino-1-carboxypentyl)iminodiacetic acid]succinyl) (DOGS-NTA) were obtained from Avanti Polar Lipids (Alabaster, Ala.). Texas Red® 1,2-dihexadecanoyl-sn-glycero-3-phosphoethanolamine (Texas Red® DHPE) was obtained from Life Technologies (Grand Island, N.Y.).

Methods—Stock Solutions: Stock solutions of DOPC, DOGS-NTA, and DHPE Texas Red lipids were made up in chloroform and mixed to give the appropriate molar ratio. The mixture was placed in a Roto-Vap (Buchi Rotovapor R-210) and chloroform was removed by evaporation under vacuum for 2 h. Any residual chloroform was removed by blowing dry nitrogen gas over the cake for 5 min. The dried lipids were resuspended in diH2O at a total lipid concentration of 0.5 mg/mL. SUV were prepared using a Sonic Dismembator Ultrasonic Processor (Fisher Scientific) at 25% amplitude for 90 seconds. The SUV prep was then centrifuged for 30 min at 16,873×g and the supernatants stored at 4° C. until use.

Methods—Proteins and Labeling: N-terminal poly-histidine tagged MBP was purchased from AtGen Co, Ltd (Seongnam-si, Gyeonggi-do, South Korea). N-terminal poly-histidine tagged human calmodulin was obtained from EMD Millipore (Billerica, Mass.). The N-terminus His-tag (8 His) ecDHFR variants were constructed using the Stratagene QuikChange site-directed mutagenesis kit and the wild-type ecDHFR template as described.(ref: Cameron C E, Benkovic S J (1997) Evidence for a Functional Role of the Dynamics of Glycine-121 of *Escherichia coli* Dihydrofolate Reductase Obtained from Kinetic Analysis of a Site-Directed Mutant. Biochemistry 36(50):15792-15800) For the His-tagged M20C variant, the two native cysteines (C85 and C152) in the wild-type enzyme were mutated to Ala and Ser, respectively, to generate a $\Delta$Cys ecDHFR as described elsewhere (ref: Liu C T, et al. (2014) Probing the Electrostatics of Active Site Microenvironments along the Catalytic Cycle for *Escherichia coli* Dihydrofolate Reductase. J Am Chem Soc 136(29):10349-10360). The choice of amino acid substitution (C85A/C152S) was shown to have no impact on the enzymatic activity. Selective incorporation of cysteine was achieved through subsequent mutations using the primer: 5'-GGC ATG GAA AAC GCC TGT CCA TGG AAC CTG -3'. Plasmid construction, protein expression, and purification of mutant DHFRs were performed according to the published protocol (cite: the Cameron & Benkovic 1997 paper above). The purified His-tag *E. coli* DHFR and its single-cysteine M20C derivative were found to have enzyme activity comparable to that of the WT enzyme. The His-tag WT enzyme, His-tag M20C, and non-His-tag WT *E. coli* DHFR yielded hydride transfer rates of 205±20 s-1, 180±10 s-1, and 220 s-1 at pH 7 and 25° C. (under standard kinetic condition described in ref [28].

The SH-active dyes PyMPO-SE and PyMPO-maleimide were synthesized by ChemShuttle (Wuxi City, China). The dye was conjugated to each protein using standard coupling techniques for either amine or thiol reactive dyes. Unless otherwise indicated, labeling reactions for the amine reactive dye were carried out at pH 8.3. Thiol-reactive dye reactions were carried out at pH 7.0. The labeled protein was separated from the free dye with Zeba Spin Desalting columns with a 7K MWCO (Thermo Fisher, Rockford, Ill.). The UV-Vis spectra of each conjugated was measured and the degree of labeling (dye:protein stoichiometry) was determined using the known extinction coefficients of the proteins and the dye. The identification and analysis of the dye-modified residues by Liquid Chromatography/Mass spectrometry were performed by Martin-Protein (Princeton, N.J.).

Methods—Sample Preparation: Glass slides (Fisher) were cleaned in Piranha (30% H2O2, 70% H2SO4) at 100°C for 20 minutes. After cooling, the slides were washed five times with deionized water and dried with nitrogen gas. A custom 2mm thick silicone gasket template with adhesive backing (Arrowleaf Research, Bend, Oreg., USA) was applied to cleaned slides. Each silicone gasket template defined 16 wells, each with a total volume of ~14 µL. The spacing and diameter of the wells is based on the standard 384-well plate format. SUV's were incubated with 1 mM NiCl2 (Sigma, St. Louis, Mo.) for 30 minutes, diluted five-fold in buffer, and added to each well. After bilayer formation, wells were washed with buffer to remove unbound SUVs and imaged by fluorescence microscopy to determine that the bilayer was uniform across the surface[40]. Protein was then added to the wells at the desired concentration and allowed to incubate for a minimum of an hour. Excess protein was removed by additional washes after incubation.

Each protein was screened to determine an optimized binding buffer for bilayer attachment and SHG signal production. For MBP, the optimized buffer is 20 mM Tris pH 8.0, 150 mM NaCl, 0.05% Tween-20, and 1 mM DTT. For CaM, the optimized buffer is 25 mM MOPS pH 7, 150 mM KCl, 2 mM $MgCl_2$ (with or without 2 mM $CaCl_2$). For DHFR, the optimized buffer is 50 mM sodium phosphate, pH 7.0 with 100 µM NADPH (Sigma). For conformational change experiments, 9 µM MBP, 2 µM CaM, or 4µM DHFR was incubated in each well for a minimum of 1 hour. The stability experiments were carried out after overnight incubation in the wells at 4° C. For the specificity experiments, each protein was incubated in 25 mM Tris pH 7.2 and 150 mM NaCl, with or without 300 mM imidazole. Excess protein and imidazole was removed with by washing with 25 mM Tris pH 7.2, 150 mM NaCl prior to SHG data acquisition.

Methods—SHG Instrumentation and Experiments: Our instrument comprises a mode-locked Ti:Sapphire oscillator which provides the fundamental beam necessary to generate the second-harmonic signal (high peak power). For these experiments, we used a Mira 900 Ti:Sapphire ultrafast oscillator (Coherent Inc., Santa Clara, Calif., USA) pumped by a Millenia V DPSS laser (Spectra-Physics Corp., Santa Clara, Calif., USA). The fundamental was passed through a half-wave plate to select p-polarization (used for all the experiments described here), and focused into a Dove prism for total internal reflection (TIR) to a spot size of ~50 um. The second harmonic light was collected by a lens, separated from the fundamental using a dichroic mirror and wavelength filters, and directed into a PMT module with a built-in pre-amplifier for photon counting (Hamamatsu, Bridgewater, N.J., USA). A custom electronics board was used to digitize the signal and the data was sent to a computer running customized control and data collection software (Labview, National Instruments Corp. Austin, Tex., USA).

For these experiments, the microscope slide with protein was coupled to a prism using BK7 index matching fluid (Cargille, Cedar Grove, N.J., USA) and the prism itself secured onto a 1-D translation stage capable of 10 µm randomly-addressable precision (Renishaw, Parker-Hannifin Corp, Rohnert Park, Calif., USA).

Ligand addition was carried out while SHG signal was monitored in real time. Once baseline signal was established, buffer was injected into the well as a control. After 5-10 seconds to to assess how the buffer injection changed the signal, the compound of interest was injected into the well to the desired final concentration. SHG signal was monitored over several minutes after injection.

Methods—SHG Quantification: To calculate the percent change, the SHG intensity measured just prior to ligand injection ($T_0$) was subtracted from the SHG intensity at equilibrium ($T_{eq}$) and then normalized by $T_0$ according to the following equation: SHG %=($I_{SHG}$@$T_{eq}$-$I_{SHG}$@$T_0$)/

$I_{SHG}@T_0$. The $T_{eq}$ for each ligand was experimentally determined but in most cases equilibrium was achieved in less than one minute. In addition, all experiments included a control buffer injection that was used to determine the threshold for SHG intensity change and was calculated in a similar manner.

Changes in SHG signal separated from the average buffer shift by more than three times the standard deviation of the buffer shift are considered to indicate a change in the angle of the dye and therefore the conformation of the protein at the labeled residue(s).

Figure 11A:
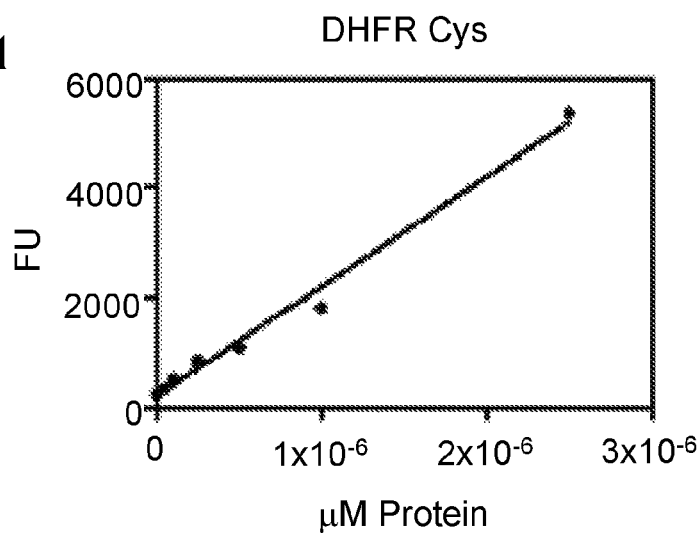
FIG. 11A shows a standard curve for the fluorescence from cysteine-labeled DHFR.
Figure 11B:
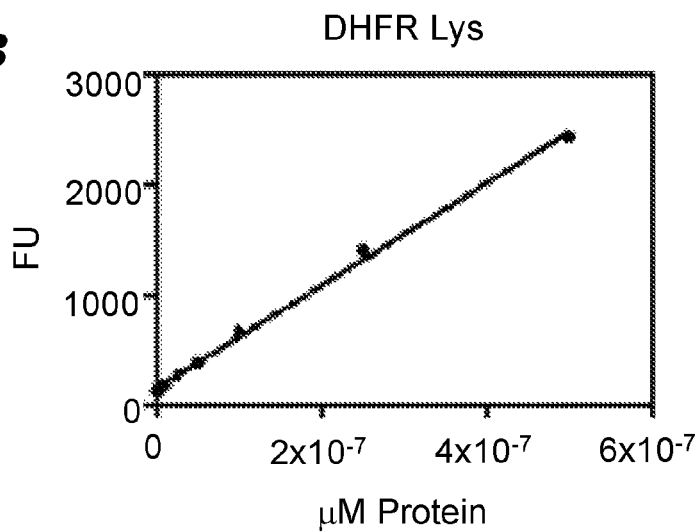
FIG. 11B shows a standard curve for the fluorescence from lysine-labeled DHFR.
Figure 11C:
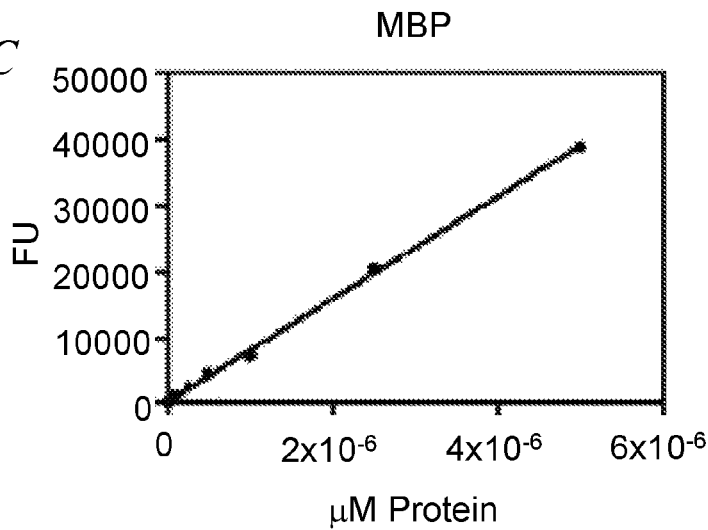
FIG. 11C shows a standard curve for the fluorescence from labeled MBP. Tethered and labeled protein attached to the Ni-NTA bilayer was removed from the glass surfaces by serial detergent washes. Cysteine-labeled DHFR, lysine-labeled DHFR, and MBP were all determined to be tethered at surface densities on the order of $1 \times 10^{12}$ molecules per $cm^2$.

Supplemental Methods—Quantification of the Surface Density of Protein Molecules: Four wells each of MBP and DHFR were incubated in wells containing supported lipid bilayer at 4 uM in their respective buffers. After 1 hour, wells were washed 5×20µL with the appropriate buffer, and SHG signal was measured to confirm binding. A 10 µl aliquot of PBS/LDAO was used to wash the first well and this was carried forward into three other wells so that protein was collected from a total of 4 replicate wells. Five more 10 µl aliquots of PBS/LDAO were used to wash out the wells in the same manner, so that in total 6×10 µl aliquots were used to wash out the 4 wells. Four wells were used to increase the fluorescence signal-to-noise and to average over separate wells. The wash was collected and monitored for PyMPO fluorescence on a Horiba Jobin Yvon Fluorolog F-1000 fluorimeter in a 384-well plate. PyMPO was excited at 415 nm and emission was collected from 520 to 620 nm. Standard curves for each labeled protein were generated (FIGS. 11A-C) to calculate the concentration of protein in the samples from the slides and therefore to determine the number of molecules tethered to the surface in one well.

References

1. Goodey, N. M. and S. J. Benkovic, Allosteric regulation and catalysis emerge via a common route. Nat. Chem. Biol., 2008. 4(8): p. 474-82.

2. Goh, C. S., D. Milburn, and M. Gerstein, Conformational changes associated with protein-protein interactions. Curr. Opin. Struct. Biol., 2004. 14(1): p. 104-9.

3. Kull, F. J. and S. A. Endow, Force generation by kinesin and myosin cytoskeletal motor proteins. J Cell Sci., 2013. 126(Pt 1): p. 9-19.

4. Tompa, P., Intrinsically disordered proteins: a 10-year recap. Trends Biochem. Sci., 2012. 37(12): p. 509-16.

5. Heinz, T. F., H. W. K. Tom, and Y. R. Shen, Determination of molecular orientation of monolayer adsorbates by optical second-harmonic generation. Physical Review A, 1983. 28(3): p. 1883-1885.

6. Zhuang, X., et al., Mapping molecular orientation and conformation at interfaces by surface nonlinear optics. Physical Review B, 1999. 59(19): p. 12632-12640.

7. Salafsky, J. S., 'SHG-labels' for detection of molecules by second harmonic generation. Chemical Physics Letters, 2001. 342(5-6): p. 485-491.

8. Bucher, D., B. J. Grant, and J. A. McCammon, Induced fit or conformational selection? The role of the semi-closed state in the maltose binding protein. Biochemistry, 2011. 50(48): p. 10530-9.

9. Evenas, J., et al., Ligand-induced structural changes to maltodextrin-binding protein as studied by solution NMR spectroscopy. J Mol. Biol., 2001. 309(4): p. 961-74.

10. Kondo, H. X., et al., Free-energy landscapes of protein domain movements upon ligand binding. J Phys. Chem. B, 2011. 115(23): p. 7629-36.

11. Seo, M. H., et al., Protein conformational dynamics dictate the binding affinity for a ligand. Nat. Commun., 2014. 5: p. 3724.

12. Staii, C., D. W. Wood, and G. Scoles, Ligand-induced structural changes in maltose binding proteins measured by atomic force microscopy. Nano Lett., 2008. 8(8): p. 2503-9.

13. Millet, O., R. P. Hudson, and L. E. Kay, The energetic cost of domain reorientation in maltose-binding protein as studied by NMR and fluorescence spectroscopy. Proc. Natl. Acad. Sci. USA, 2003. 100(22): p. 12700-5.

14. Duan, X., et al., Crystal structures of the maltodextrin/maltose-binding protein complexed with reduced oligosaccharides: flexibility of tertiary structure and ligand binding. J Mol. Biol., 2001. 306(5): p. 1115-26.

15. Spurlino, J. C., G. Y. Lu, and F. A. Quiocho, The 2.3-A resolution structure of the maltose- or maltodextrin-binding protein, a primary receptor of bacterial active transport and chemotaxis. J Biol. Chem., 1991. 266(8): p. 5202-19.

16. Quiocho, F. A. and P. S. Ledvina, Atomic structure and specificity of bacterial periplasmic receptors for active transport and chemotaxis: variation of common themes. Mol. Microbiol., 1996. 20(1): p. 17-25.

17. Medintz, I. L. and J. R. Deschamps, Maltose-binding protein: a versatile platform for prototyping biosensing. Curr. Opin. Biotechnol., 2006. 17(1): p. 17-27.

18. Dwyer, M. A. and H. W. Hellinga, Periplasmic binding proteins: a versatile superfamily for protein engineering. Curr. Opin. Struct. Biol., 2004. 14(4): p. 495-504.

19. Chin, D. and A. R. Means, Calmodulin: a prototypical calcium sensor. Trends Cell Biol., 2000. 10(8): p. 322-8.

20. Kursula, P., Crystallographic snapshots of initial steps in the collapse of the calmodulin central helix. Acta Crystallogr. D Biol. Crystallogr., 2014. 70(Pt 1): p. 24-30.

21. Grabarek, Z., Structure of a trapped intermediate of calmodulin: calcium regulation of EF-hand proteins from a new perspective. J Mol. Biol., 2005. 346(5): p. 1351-66.

22. Marlow, M. S., et al., The role of conformational entropy in molecular recognition by calmodulin. Nat. Chem. Biol., 2010. 6(5): p. 352-8.

23. O'Donnell, S. E., et al., Thermodynamics and conformational change governing domain-domain interactions of calmodulin. Methods Enzymol., 2009. 466: p. 503-26.

24. Villarroel, A., et al., The ever changing moods of calmodulin: how structural plasticity entails transductional adaptability. J Mol. Biol., 2014. 426(15): p. 2717-35.

25. Arora, K. and C. L. Brooks, 3rd, Multiple intermediates, diverse conformations, and cooperative conformational changes underlie the catalytic hydride transfer reaction of dihydrofolate reductase. Top. Curr. Chem., 2013. 337: p. 165-87.

26. Hammes-Schiffer, S. and S. J. Benkovic, Relating protein motion to catalysis. Annu. Rev. Biochem., 2006. 75: p. 519-41.

27. Schnell, J. R., H. J. Dyson, and P. E. Wright, Structure, dynamics, and catalytic function of dihydrofolate reductase. Annu. Rev. Biophys. Biomol. Struct., 2004. 33: p. 119-40.

28. Fierke, C. A., K. A. Johnson, and S. J. Benkovic, Construction and evaluation of the kinetic scheme associated with dihydrofolate reductase from *Escherichia coli*. Biochemistry, 1987. 26(13): p. 4085-92.

29. Schweitzer, B. I., A. P. Dicker, and J. R. Bertino, Dihydrofolate reductase as a therapeutic target. FASEB J, 1990. 4(8): p. 2441-52.

30. Sawaya, M. R. and J. Kraut, Loop and subdomain movements in the mechanism of *Eschcrichia coli* dihydrofolate reductase: crystallographic evidence. Biochemistry, 1997. 36(3): p. 586-603.

31. Venkitakrishnan, R. P., et al., Conformational changes in the active site loops of dihydrofolate reductase during the catalytic cycle. Biochemistry, 2004. 43(51): p. 16046-55.

32. Salafsky, J. S., Detection of protein conformational change by optical second-harmonic generation. J Chem. Phys., 2006. 125(7): p. 074701.

33. Salafsky, J. S., Second-harmonic generation as a probe of conformational change in molecules. Chemical Physics Letters, 2003. 381(5-6): p. 705-709.

34. Mcnaa, B., et al., Favourable influence of hydrophobic surfaces on protein structure in porous organically-modified silica glasses. Biomaterials, 2008. 29(18): p. 2710-8.

35. Menaa, B., et al., Protein adsorption onto organically modified silica glass leads to a different structure than sol-gel encapsulation. Biophys. J. 2008. 95(8): p. L51-3.

36. Manz, B. N., et al., T-cell triggering thresholds are modulated by the number of antigen within individual T-cell receptor clusters. Proceedings of the National Academy of Sciences, 2011. 108(22): p. 9089-9094.

37. Dustin, M. L. and J. T. Groves, Receptor Signaling Clusters in the Immune Synapse. Annual Review of Biophysics, 2012. 41(1): p. 543-556.

38. Block, H., et al., Immobilized-metal affinity chromatography (IMAC): a review. Methods Enzymol., 2009. 463: p. 439-73.

39. Nye, J. A. and J. T. Groves, Kinetic control of histidine-tagged protein surface density on supported lipid bilayers. Langmuir, 2008. 24(8): p. 4145-9.

40. Nye, J. A. and J. T. Groves, Kinetic Control of Histidine-Tagged Protein Surface Density on Supported Lipid Bilayers. Langmuir, 2008. 24(8): p. 4145-4149.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosed methods and devices. It should be understood that various alternatives to the embodiments of the methods and devices described herein may be employed in practicing the novel approaches disclosed herein. It is intended that the following claims define the scope of the disclosed methods and devices, and that methods and structures within the scope of these claims and their equivalents be covered thereby.

What is claimed is:

1. A method comprising:
   a) forming a supported lipid bilayer on a surface of a substrate, wherein the supported lipid bilayer comprises an anchor molecule that comprises or bears a first affinity tag that is present in the lipid bilayer at a concentration greater than or equal to 10 mole percent;
   b) contacting the supported lipid bilayer with a protein at a concentration of less than 2 µM, wherein the protein comprises a second harmonic-active label, a second affinity tag capable of binding to the first affinity tag, and optionally a linker molecule positioned between the protein and the second affinity tag, thereby tethering the protein to the supported lipid bilayer in an oriented fashion while using less than 500 ng of the protein, wherein the tethered protein is tethered at a surface density of about $1 \times 10^{12}$ molecules per $cm^2$; and
   c) detecting an optical signal arising from the tethered protein before and after contacting the tethered protein with a ligand, wherein the optical signal is second harmonic light, and wherein a change in the optical signal detected before and after contacting the tethered protein with the ligand indicates that the protein has undergone a conformational change.

2. The method of claim 1, wherein the first affinity and the second affinity tags are Ni-NTA and poly-histidine tags.

3. The method of claim 2, wherein the poly-histidine tag is attached to the N-terminus of the protein.

4. The method of claim 2, wherein the poly-histidine tag is attached to the C-terminus of the protein.

5. The method of claim 2, wherein the poly-histidine tag comprises between 4 and 24 histidine residues.

6. The method of claim 2, wherein the poly-histidine tag comprises 8 histidine residues.

7. The method of claim 2, wherein the poly-histidine tag comprises 6 histidine residues.

8. The method of claim 1, wherein the first affinity tag comprises $cobalt^{2+}$-carboxylmethylaspartate (Co-CMA) and the second affinity tag comprises a poly-histidine tag.

9. The method of claim 1, wherein the first affinity tag comprises biotin and the second affinity tag comprises streptavidin.

10. The method of claim 1, wherein the first affinity tag comprises biotin and the second affinity tag comprises avidin.

11. The method of claim 1, wherein the first affinity tag comprises biotin and the second affinity tag comprises neutravidin.

12. The method of claim 1, wherein the concentration of the anchor molecule comprising the first affinity tag is adjusted to a value ranging from 10 mole percent to 100 mole percent of the lipid bilayer.

13. The method of claim 1, further comprising incubating the supported lipid bilayer with the protein for about 10 minutes to about 60 minutes.

14. The method of claim 1, wherein the supported lipid bilayer comprises 1,2-dioleoyl-sn-glycero-3-phosphocholine.

15. The method of claim 1, wherein the anchor molecule conjugated to the first affinity tag comprises 1,2-dioleoyl-sn-glycero-3-[(N-(5-amino-1-carboxypentyl)iminodiacetic acid)succinyl] (nickel salt).

16. The method of claim 1, wherein the linker molecule comprises an omega-amino fatty acid or polyethylene glycol molecule.

* * * * *